United States Patent [19]

Hwang et al.

[11] Patent Number: 5,441,983
[45] Date of Patent: Aug. 15, 1995

[54] TREATMENT OF INFECTION BY ENVELOPED VIRUS WITH CALIX(N)ARENE COMPOUNDS

[75] Inventors: Kou M. Hwang, Danville; You M. Qi, Sunnyvale; Su-Ying Liu, Belmont; William Choy; Jen Chen, both of Sunnyvale, all of Calif.

[73] Assignee: Genelabs Incorporated, Redwood City, Calif.

[21] Appl. No.: 928,108

[22] Filed: Aug. 6, 1992

Related U.S. Application Data

[63] Continuation-in-part of Ser. No. 791,920, Nov. 13, 1991, Pat. No. 5,312,837, which is a continuation-in-part of Ser. No. 647,720, Jan. 29, 1991, Pat. No. 5,196,452, which is a continuation-in-part of Ser. No. 647,469, Jan. 29, 1991, Pat. No. 5,166,173.

[51] Int. Cl.⁶ ............................................. A61K 31/195
[52] U.S. Cl. ................................... 514/562; 514/130; 514/143; 514/510; 514/569; 514/572; 514/602; 514/709; 514/732
[58] Field of Search ............... 514/130, 143, 510, 562, 514/569, 577, 602, 709, 732

[56] References Cited

U.S. PATENT DOCUMENTS 4,604,404  8/1986  Munson, Jr. et al. .

FOREIGN PATENT DOCUMENTS

0467185A2  1/1992  European Pat. Off. .
2229198  9/1990  Japan .
721103  1/1978  U.S.S.R. .
WO90/00596  1/1990  WIPO .

OTHER PUBLICATIONS

Merck Index 10th Ed #140 & 8097, 1983.
Merck Index 10th Ed #10023, 1983.
Akerfeldt, S. et al., "Aromatic Sulfonic Acids as Viral Inhibitors. Structure–Activity Study using Rhino, Adeno 3, Herpes Simplex, and Influenza Viruses", J. Med. Chem. 14(7):596–600 (1971).
Makabe, O., and Shinkai, S., "Calexarene derivatives", Chem. Abst. 105:568 (1986).
Poh, B.-L., and Lim, C. S., "Complexations of Amines with Water–Soluble Cyclotetrachromotropylene", Tetrahedron 46(10):3651–3658 (1990).
Poh, B.-L., et al., "A Water–Soluble Cyclic Tetramer From Reacting Chromotropic Acid With Formaldehyde", Tetra. Letters 30(8):1005–1008 (1989).
Poh, B.-L., et al., "Complexations of Metal Cations With Cyclotetrachromotropylene in Water and Methanol", Tetrahedron 46(12):4379–4386 (1990).
Shinkai, S., et al., "Selective absorption of uranyl ion ($UO_2^{2+}$) to a polymer resin immobilizing calixarene-based uranophiles", Chem. Abst. 109:35 (1988).
Alam, I., and C. D. Gutsche, "Calixarenes. 24. Complexation by Water–Soluble Calixarenes", J. Org. Chem. 55:4487–4489 (1990).
Almi, M., et al., "Chloromethylation of Calixarenes and Synthesis of New Water Soluble Macrocyclic Hosts", Tetrahedron 45(7):2177–2182 (1989).
Kawasaki, M., "Spot prevention in silver halide photographic material", Chemical Abstracts 117(16): abstract No. 160793y (1992).

(List continued on next page.)

Primary Examiner—Marianne M. Cintins
Assistant Examiner—Russell Travers
Attorney, Agent, or Firm—Peter J. Dehlinger; Vincent M. Powers

[57]  ABSTRACT

A method for inhibiting cell infection by an enveloped virus, by administering to an infection site, a therapeutically effective amount of a calix(n)arene compound derivatized, at its ring positions meta to the bridge attachments to the ring, with polar substitutent having a terminal carboxylate, phosphate, or sulfonate groups, including esters and amides which are cleavable in vivo. The compound may be administered orally, or topically, e.g., for treatment of herpes virus.

16 Claims, 25 Drawing Sheets

OTHER PUBLICATIONS

Patrick, T. B., and P. A. Egan, "An Improved Preparation of Phenolic [1.1.1.1]Metacyclophanes", *J. Org. Chem.* 42(2):382–383 (1977).

Yilmaz, M., and U. S. Vural, "Synthesis of New Substituted Calix[4]Arenes and Their Complexes with Iron-(III)", *Synth. React. Inorg. Met.-Org. Chem.* 21(8):1231–1241 (1991).

Shinaki, S., et al., "Synthesis and inclusion properties of neutral water-soluble calixarenes", Chem. Abst. 113:666 (1990).

Shinkai, S., et al., "New Syntheses of Calixarene-$p$-sulphonates and $p$-Nitrocalixarenes", J. Chem. Soc. Perkin Trans. I:2297–2299 (1987).

Shinkai, S., et al., "Hexasulfonated Calix[6]arene Derivatives: A New Class of Catalysts, Surfactants, and Host Molecules", J. Am. Chem. Soc. 108:2409–2416 (1986).

Shinkai, S., et al., "New Water-Soluble Host Molecules Derived From Calix[6]arene", Tetra. Letters 25(46):5315–5318 (1984).

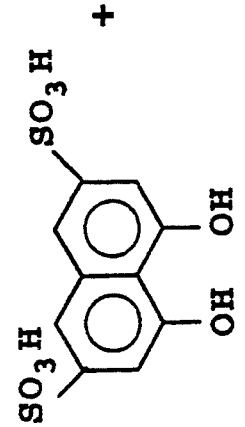 + R'-CHO ⟶ 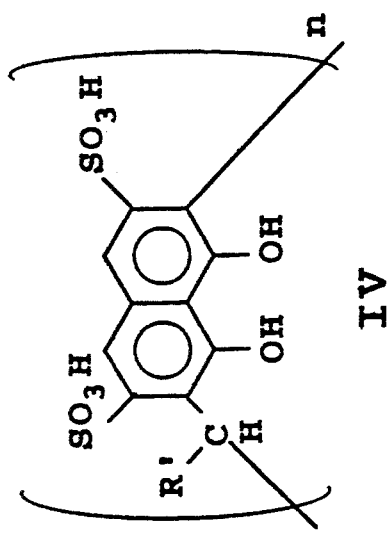
Fig. 3A
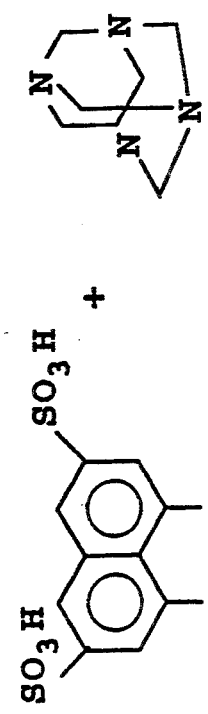 + 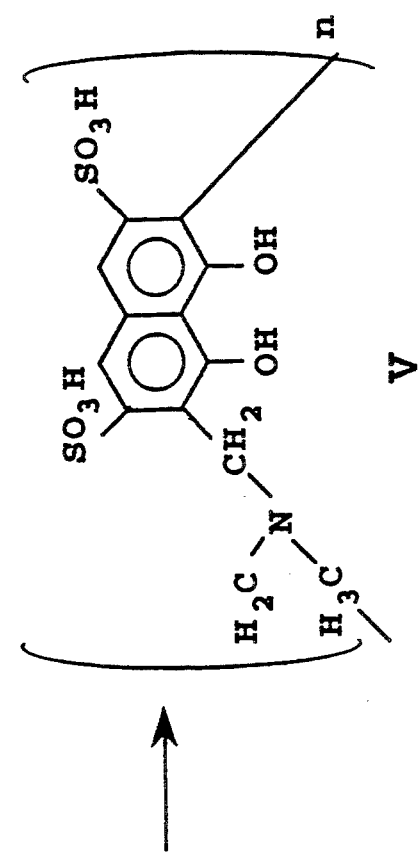
Fig. 3B

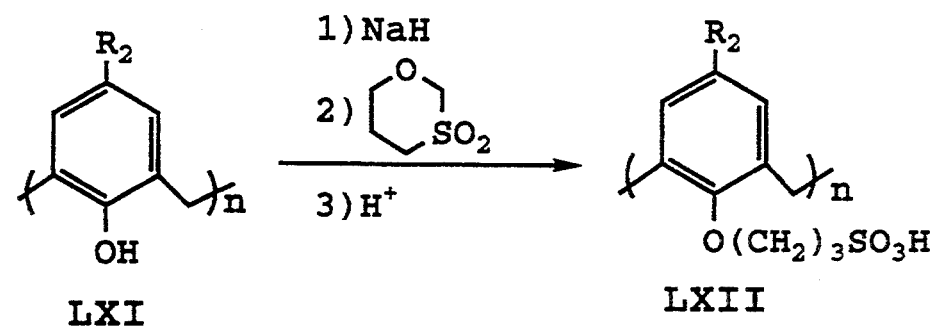
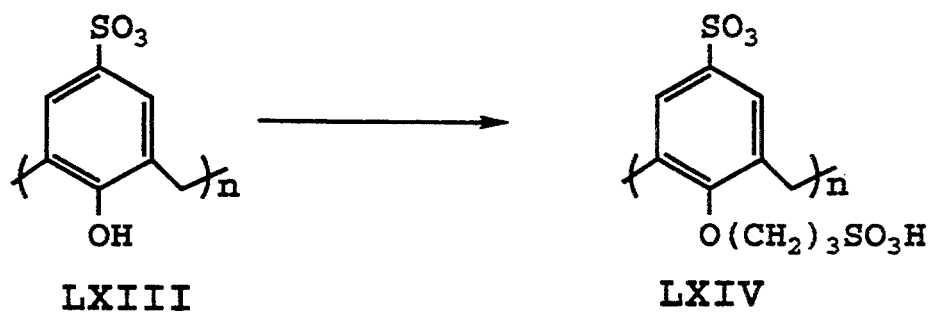
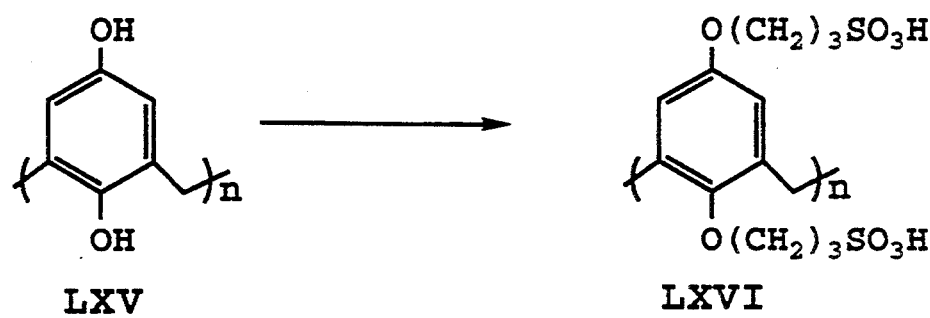
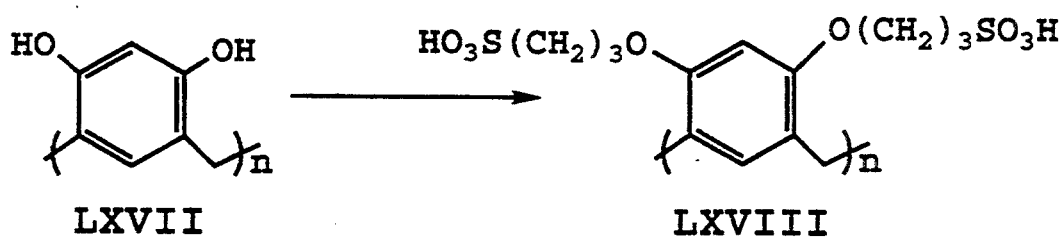
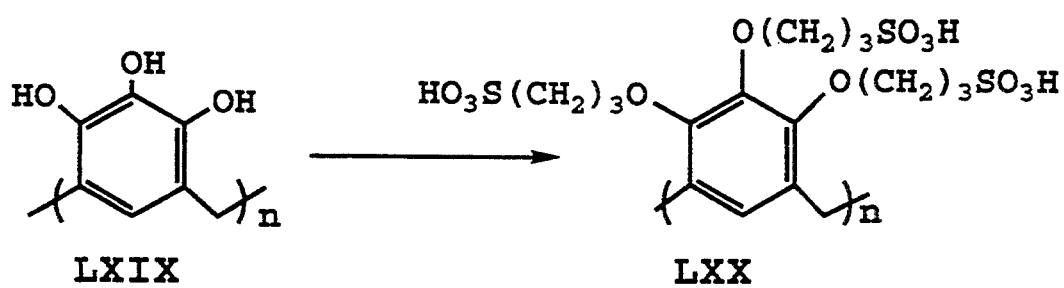
Fig. 27

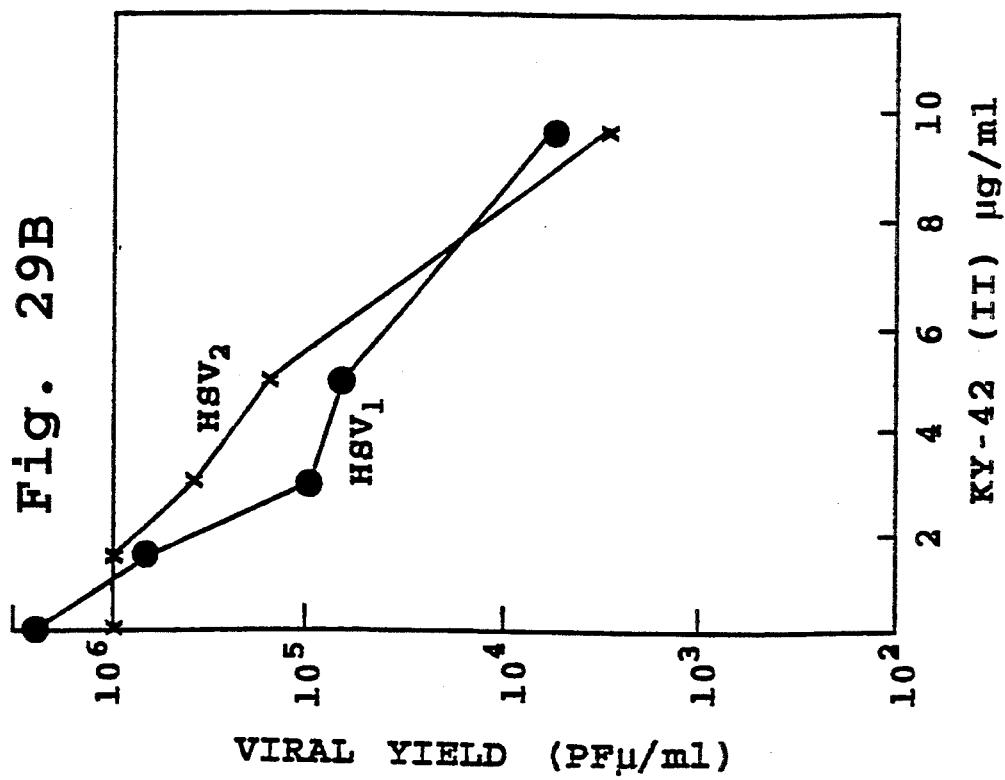
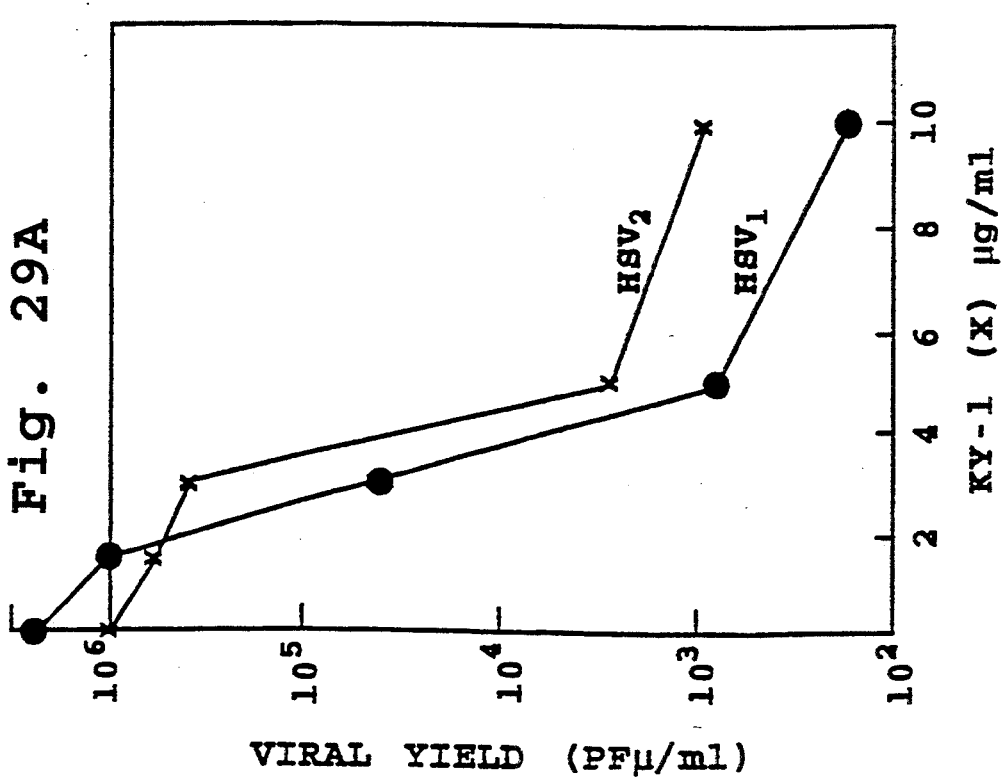

TREATMENT OF INFECTION BY ENVELOPED VIRUS WITH CALIX(N)ARENE COMPOUNDS

The present invention is a continuation-in-part of U.S. patent application for "Method of Treating Viral Infections with Aryl Macrocyclic Compounds", Ser. No. 07/791,920, filed Nov. 13, 1991, now U.S. Pat. No. 5,312,837 which is a continuation-in-part of U.S. patent application for "Macrocyclic Anti-Viral Compound and Method". Ser. No. 07/647,720, filed Jan. 29,1991, now U.S. Pat. No. 5,196,452, which is a continuation-in-part of U.S. patent application for and Method of Treating Herpes Simplex Virus Infection", Ser. No. 647,469, both filed Jan. 29, 1992, now U.S. Pat. No. 5,166,173.

FIELD OF THE INVENTION

The present invention relates to a method for inhibiting cell infection by enveloped viruses, and more particularly, to a method which employs a defined class of calix (n) arene compounds.

REFERENCES

Allen, R. M., Clin Neuropharmacol, 6:S64 (1983).
Almi, M., Arduini, A., Casnati, A., Pochini, A., and Arduini A., Pochini, A., Rizzi, A., Sicuri, A. R., and Barre-Simoussi, F., et al., Science 220:868-871 (1983).
Blackburn, G. M., et al., Chemica Scripta, 26:21 (1986).
Bundgaard, H , ed "Design of Prodrugs", Elsivier, Amsterdam (1985).
Chanock, R. M., et al., Am.J.Hyg. 66:29-300 (1957).
Collins, P., J Antimicrob Chemoth, 5:431 (1979).
de Mendoza, J., Nieto, P. M., Prados, P., and Sanchez, C. (1990) Tetrahedron 46, 671-682.
Dick, E. C., Proc. Soc. Exp.Biol.Med. 27:1079-1081 (1968).
Erlich, K. S., et al., N.Eng. J.Med. 320:293-296 (1989).
Elion, G. B., et al., Proc. Natl.Acad. Sci USA 74:5617-5620 (1977).
Galbraith, A. W., Lancet, 1026 (1969).
Gibrack, C. D., et al., J.Inf.Dis. 146:673-682 (1982).
Gottlieb, M. S., et al., N.Eng.J.Med. 305:425-3 (1981).
Gormer, B., et al. (1990) Makromol. Chem. 191, 81-87.
Gutsche, C. D. (1991) "Single Step Synthesis and Properties of Calixarenes" in Calixaranes—a Versatile Class of Macrocyclic Compounds, Vicens, J., and Bohmer, V. Editors, Kluwer Academic Publishers, Dordrecht, The Netherlands, pp. 1-37.
Gutsche, C. D., and Nam, K. C. (1988) J. Am. Chem. Soc. 10, 6153-6162.
Gutsche, C. D., Dhawan, B., Levine, J. A., No, K. H., and Bauer, L. J. (1983) Tetrahedron 39, 409-426.
Gutsche, C. D., and Lin, L. G. (1986) Tetrahedron 42, 633-1640.
Gutsche, C. D., Levine, J. A., and Sujeeth, P. K. (1985) J. Org. Chem. 50, 5802-5806.
Hansch, C., Leo, A., Structure-Activity Correlation, Wiley, (1979).
Hansch, C. in Drug Design (E. J. Ariens, ed.), Vol. II, p. 271, Academic Press, (1971).
Hilleman, M. R., Proc. Soc. Exp. Biol.Med. 85:183-188 (1954).
Hirao, T., Masunaga, T., Yamada, N., Ohshiro, Y., and Agawa, T. (1982) Bull. Chem. Soc. Jpn. 55, 909-913.
Huttunen, p., et al, Pharmacol Biochem & Behav 4:1733-38 (1986).
Jaffe, Chem. Rev., 53, 191 (1953).
Kern, E. R., Amer.J.Med. 73:100-108 (1982).
Klatzmann, D., et al., Science 225:59-63 (1984).
Lifson, J. D., et al., Science 241:712-716 (1988).
March, J., Advanced Organic Chemistry $3^{rd}$ ed., Chapter 9, Wiley (1985).
Martin, J. C., ed. Nucleoside Analogues as Antiviral Agents, ACS, Washington D.C. (1989).
Mertz, G. J., et al., JAMA 260:201-206 (1988).
Mitsuya, M., et al., Proc. Natl.Acad.Sci.: 82:7096-7100, USA (1985).
Morita et al. (1989) Chem. Lett., p. 1349-.
No et al. (1986) Bull. Kor. Chem. Soc. 7, 442.
Po, B-L, et al., Tetrahedron Letters, 30(8):1005 (1989) .
Po, B-L, et al., Tetrahedron, 46(10):3651 (1990).
Po, B-L, et al., Tetrahedron, 46(12):4379 (1990).
Popovic, M., et al. Science 224:497-500 (1984).
Roizman, B., et al, Inter. Virol. 16:201-217 (1981).
Roizman, B., et al, J. Virol. 15:75-79 (1961).
Rowe, W. P., et al., Proc. Soc. Exp. Biol.Med. 84:570-573 (953).
Schaefer, J. P., Higgins, J. G., and Shenoy P. K. (1973) Org. Synth., Coll. Vol. V, 249.
Shinkai, S, et al. (1987) J. Chem. Coc. Perkin Trans. I, 2297-2299.
Shinkai, S., et al. (1989) J. Chem. Soc. Perkin Trans. I, 2039-2045.
Sidwell, R. W., App Microbiol, 22:797 (1971).
Smith, K. O., et al., Antimicrob Agts Chemother 22:55 (1982) .
Smith, R. A., et al., "Ribavirin: A broad spectrum antiviral agent: In: Stapleton, T., Editor, Studies With a Broad Spectrum Antiviral Agent. International Congress and Symposium Service (London), Royal Society of Medicine, 3-23 (1986).
Spear, P. G. [Roizman, B., Editor], The Herpes Simplex Viruses, Vol. 3, Plenum Press, New York, pp. 315-356 (1989) .
Stannard, L. M., et al., J. Gen. Virol., 68:715-725 (1987).
Stella, V. J., et al., "Trends in Prodrug Research", Vol 5(11) :276 (1984).
Svensson, L. A., et al., Drug Metab Rev, 19:165 (1988).
Svensson, L. A., et al., Drug News and Perspecti, (9) :544 (1991).
Ungaro, R. (1989) Tetrahedron 45, 2177-2182.
Ungaro, R. (1990) Tet. Lett. 31, 4653-4656.
Weinelt, F., and Schneider, H-J. (1991) J. Org. Chem. 6, 5527-5535.
Yilmaz, M., and Vural, U. S. (1991) Synth. React. Inorg. Met. Org. Chem. 21, 1231-1241.

BACKGROUND OF THE INVENTION

The challenge in developing an effective therapy and prophylaxis for viral disease is to achieve inhibition of viral processes without producing extreme side effects and preferably without inducing viral resistance. Since viral replication requires use of the cellular apparatus of the host, treating virus infection by inhibiting viral replication can be lethal to the infected host cells as well. Ideally, the virus should be destroyed or inactivated in the host prior to its invasion of host cells. This is normally accomplished, with varying degrees of success, the host's immune system, but this mechanism requires an earlier immune response, either by a prior infection or by vaccination. Further, many viruses, such as Herpes Simplex viruses (HSV) are able to effectively elude a host's immune systems, and at least one virus, the human immunodeficiency virus (HIV) is known to cripple the host's immune system (Gottlieb).

Currently, the most widely used anti-viral agents are nucleoside analogs. This class of drugs acts by disrupting viral replication, either by inhibiting enzymes required for nucleic acid processing, or by producing defective viral genomes, such as by premature termination of replication. As an example, acyclovir, a purine analog used in treating a variety of viral diseases, including herpes simplex virus-1 (HSV-1) and herpes simplex virus-2 (HSV-2) inhibits viral replication at several key points, including inhibition of viral thymidine kinase and DNA polymerase, and DNA strand elongation (Elion). Ribavirin, another purine analog, is the drug of choice in treating respiratory syncytial viruses (RSV) infection. This compound appears to act by reducing cellular GTP levels, blocking the action of several GTP-dependent viral processes (Smith). To date, the most common drug treatment of HIV infection is with zidovudine (Azidothymidine; AZT), a thymidine analog which is particularly effective against human retroviruses. AZT acts with high affinity to block viral RNA-dependent DNA polymerase (reverse transcriptase), but does also block human DNA- polymerase and causes chain termination (Mitsuya).

Other nucleic acid analogs include ganciclovir, vidarabine, idoxuridine, trifluridine and foscarnet (an inorganic phosphate analog). As indicated above, all of these drugs, by blocking viral replication, also have the capacity to disrupt and normal host replication and/or DNA transcription processes as well (see, e.g., Martin).

Understanding of the mechanisms of infection and replication of viruses has lead to alternate drug therapies, including attempts to block viral entry into cells, alter protein synthesis at the host ribosomes, complexation of viral DNA/RNA, and immunomodulation. Interferons are glycoproteins which have complex actions including enhancement of certain immune responses as well as direct antiviral action. They are more competent in preventing infection, rather than treating established viral infection, and their use leads to undesirable problems including acute, serious discomfort, bone marrow suppression, viral resistance, and development of host immune response to the interferon.

Treatment with "anti-sense" polymers of nucleic acids is a method in which the particular viral genome is the select target. The treatment provides a highly discriminating approach which would be expected to have minimal side-effects; its use as a therapeutic is hampered by problems of targeting, introduction into cells, and the quantity of material that would be required to block each strand produced. Agents which bind to and interfere with host ribosomal protein synthesis will block viral replication. These include the toxin ricin, various plant proteins such as pokeweed anti-viral protein, alpha sarcin, and other low molecular weight compounds. The weakness with the use of these materials is their lack of selectivity. In the treatment of HIV, additional therapy has been developed by specifically targeting the unique retroviral enzyme, reverse transcriptase. Non-retroviral systems do not produce or use this enzyme, but the virus cannot replicate without it.

In some instances, understanding of structural aspects of the mechanisms of replication of viruses has provided additional drug therapies. Certain viruses, including orthomyxoviruses and paramyxovirus, herpes viruses, togaviruses and retroviruses, contain a viral envelope which surrounds the viral capsid and nucleic acid. During cell infection by an enveloped virus, the plasma membrane of the host cell is altered to include some viral-coded proteins and, as the viral nucleoprotein core exits the host cell in which it was assembled, it becomes enveloped with the modified membrane, thus forming the viral envelope. Because this structure is unique to host cells when they are virally infectious and distinct from normal cells, it can serve as an additional target for therapeutic assault.

SUMMARY OF THE INVENTION

The present invention includes a method for treating infection by an enveloped virus. The method includes administering to the site of infection a therapeutically effective dose of a calix(n)arene compound which is derivatized, at its ring positions meta to the bridge attachments to the ring, with polar substitutents having terminal carboxylate, phosphonate, or sulfonate groups.

In one general embodiment, the calix(n)arene has the general structure:

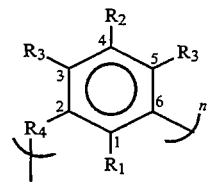

wherein (a) n=4, 6, or 8, (b) $R_2$ is a polar substitutent with a terminal carboxylate, phosphonate, or sulfonate group, including cleavable esters and amides thereof. $R_1$ is preferably OH, or in a partially oxidized form of the compound, a combination of OH and =O. $R_3$ is preferably H, and $R_4$ is preferably $CH_2$, or in the partially oxidized form just mentioned, a combination of $CH_2$ and $\geq CH$.

In a more specific embodiment, $R_2$ has the form: $(CH_2)_m R_2'$, where m=1–3, and $R_2'$ is a sulfonate group, including a sulfonate ester or amide of a lower alkyl group.

In another embodiment, $R_2$ has the form: $(CH_2)_m$—$R_2'$, where m=0–3, and $R_2'$ is a carboxylate group, including a carboxylate ester or amide of a lower alkyl group.

In yet another embodiment, $R_2$ has the form: $(CH_2)_m$—$R_2'$, where m=0–3, and $R_2'$ is a phosphonate group, including a phosphonate ester or amide of a lower alkyl group.

The compound may be administered orally, for treatment, for example of human immunodeficiency virus (HIV) respiratory syncytial virus (RSV), and herpes simplex viruses HSV-1 or HSV-2.

The compound may be administered by inhalation, for treatment of respiratory syncytial virus, and topically for treatment of HSV-1 or HSV-2. Other modes of administration, e.g., intravenous, are also contemplated.

Also contemplated is a method which employs a combination of a calix(n)arene compound and an antiviral nucleoside analog compound for treating viral infection. The calix(n)arene and nucleoside analog compounds may be formulated in an ointment vehicle, for topical administration, e.g., in treating lesions due to HSV-1 or HSV-2. Alternatively, the compounds may be formulated in liquid or tablet form for oral administration, for treatment of systemic viral infection, or in solution form for systemic administration.

In another aspect, the invention contemplates novel calix(n)arene compounds of the type described above, and having sulfonate, phosphonate, and carboxylate terminal groups.

These and other objects and features of the invention will become more fully apparent when the following detailed description of the invention is read in conjunction with the accompanying drawings.

BRIEF DESCRIPTION OF THE DRAWINGS

FIGS. 3A and 3B illustrate two general methods of synthesis of a-macrocyclic compound like the one shown in FIG. 2A;

FIG. 27 shows reaction schemes for preparing a number of calix(n)arenes having 3-sulfonlypropyloxy groups attached to the calix(n)arene rings;

FIGS. 29A and 29B are plots of HSV viral yields, as a function of drug dose, for the macrocyclic compounds KY-1 (29A) and KY-42 (29B);

DETAILED DESCRIPTION OF THE INVENTION

I. Definitions

Figure 1:
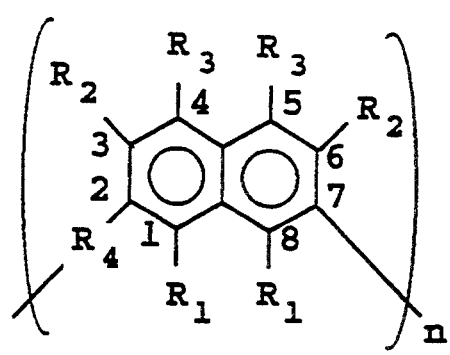
FIG. 1 shows the general structure of a macrocyclic compound composed of naphthalene subunits, for use in the present invention.

The terms defined in this section have the following meanings unless otherwise indicated.

An "enveloped virus" means a virus containing a proteinaceous viral envelope which surrounds the viral capsid. Such enveloped viruses include orthomyxoviruses and paramyxovirus, herpes viruses, togaviruses and retroviruses. During cell infection by an enveloped virus, the plasma membrane of the host cell is altered to include some viral-coded proteins and, as the viral nucleoprotein core exits the host cell in which it was assembled, it becomes enveloped with the modified membrane, thus forming the viral envelope. An "aryl ring" subunit is a single ring or fused ring structure containing at least one aromatic ring, i.e., a 5- or 6-member ring with 6 pi electrons necessary for aromaticity. Examples include benzene, naphthalene, fused ring structures, such as tetralin, and heterocyclic structures, including fused-ring structures, such as quinoline, isoquinoline, and indole.

A "macrocyclic compound composed of aryl ring subunits" is a cyclic compound formed by linking ring atoms in aryl ring subunits to form a cyclic chain.

A "calix (n) arene" or "calixarene compound" is a macrocyclic compound having a skeletal structure of the form:

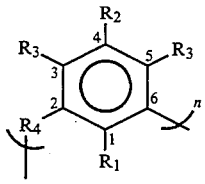

where n is preferably 4–10, more preferably 6 or 8.

The "positions of bridge attachments to the ring" in a calixarene compound refer to ring positions 2 and 6 in each ring of the compound.

The "non-bridge positions" in a calixarene compound refer to ring positions 1, 3, 4, and 5 in each ring of the compound.

The "ring position meta to the bridge attachments" in a calixarene compound refer to ring position 4 in each ring of the compound.

A "polar substituent" refers to a radical R whose octanol/water partition coefficient is less than 1.

A "polar substitutent having a terminal carboxylate, phosphonate, or sulfonate refers to R having the form —$CO_2^-$ or R'—$CO_2^-$ (carboxylate), —$PO_3^-$ or R'—$PO_3^-$ (phosphonate), —$SO_3^-$ or R'—$SO_3^-$ (sulfonate), —$SO_2^-$ or R'—$SO_2^-$ (sulfinate), where R' is a linear chain 1–4 atoms in length which is effective to link the associated carboxylate, phosphonate, or sulfonate group to the phenyl ring of calixarene. One preferred R' linear chain is $(CH_2)_m$, where m =1–3.

A "carboxylate" group includes the carboxylic acid group —$CO_2^-$, carboxylate salts, and carboxylic acid esters and amides which are cleavable in vivo. A carboxylic acid ester has the general form —$CO_2$—R, where R is an unsubstituted lower alkyl or a substituted alkyl, and a carboxylic acid amide has the general form CONR'R" where NR'R" is a secondary or tertiary amine, i.e., R' and R' are H or lower substituted or unsubstituted lower alkyl groups. A carboxylic acid ester or amide is cleavable in vivo if it is hydrolysed by serum esterases or amidases, respectively, to the corresponding carboxylic group.

A "phosphonate" group includes the phosphonic acid group —$PO_3^{-2}$ including phosphonate salts, and phosphonic acid esters and amides which are cleavable in vivo. A phosphonic acid ester has the general form —$PO_3$—RR' where R and R' are lower alkyl groups, or substituted lower alkyl groups, and a phosphonic acid amide has the general form $PO(NRR')_2$, where NRR' is a secondary or tertiary amine, where R and R' are as above. A phosphonic acid ester or amide is cleavable in vivo if it is hydrolysed by serum phosphatases or phosphoamidases, respectively, to the corresponding sulfonic acid group.

A "sulfonate" group includes the sulfonic acid group, including sulfonate salts, and sulfonic acid esters and amides which are cleavable in vivo. A sulfonic acid ester has the general form —$SO_3R$, where R is an unsubstituted lower alkyl or substituted lower alkyl group, and a sulfonic acid amide has the general form $SO_2NR'R''$, where NR'R" is a secondary or tertiary amine. A sulfonic acid ester or amide is cleavable in vivo if it is hydrolysed by serum esterases or sulfoamidases, respectively, to the corresponding sulfonic acid group.

A "lower alkyl group" is a linear or branched alkyl group containing 1–5 carbon atoms.

A "substituted lower alkyl group" is a lower alkyl group having one or more substitutions at its carbon atoms.

II. Preparing Aryl-Subunit Macrocyclic Compounds

This section describes the synthesis of two general types of aryl macrocyclic compounds which are useful in the anti-viral treatment method of the invention. The first type is composed of naphthalene subunits with sulfonic acid-derived substituents, and is the subject of earlier filed patent applications Ser. Nos. 07/791,920, 07/647,720, and 647,469. Synthesis of these compounds in described in Section A herein. The second general type, and the one which is the subject of the present application, is a calix(n)arene compound which is derivatized, at its ring positions meta to the bridge attachments to the ring, with polar substitutents having terminal carboxylate, phosphate, or sulfonate groups. Synthesis of these compounds are described in Sections B and C. From the synthetic routes given in the two sections, it will be apparent how macrocycles composed of mixed subunits, e.g., both naphthalene and calix(n)arene phenyl subunits can be prepared. The synthetic methods are also generally applicable to macrocycles composed of heterocyclic subunits with sulfonic acid-derived substitutents.

A. Macrocyclic Compounds with Substituted Naphthalene
Subunits

Figure 2A:
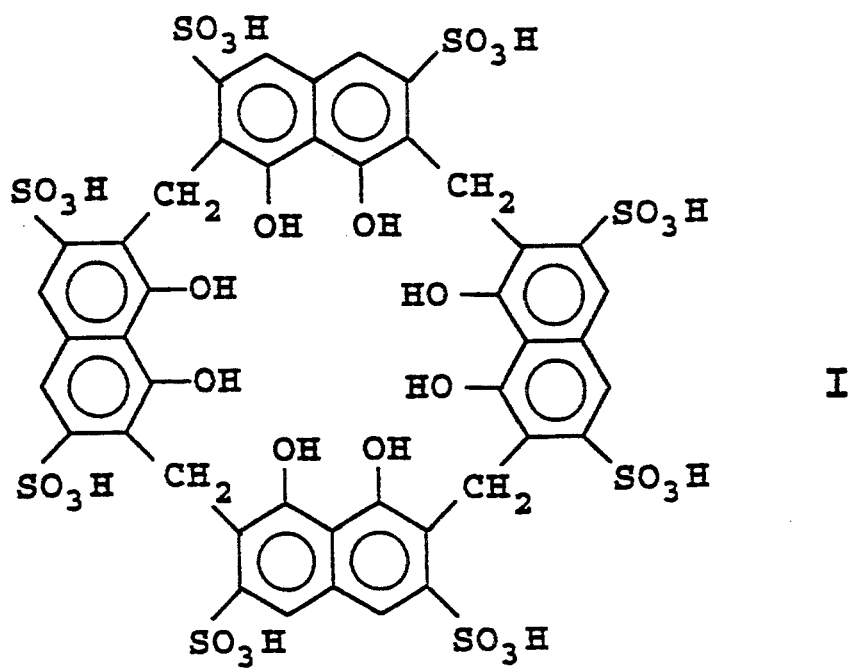
FIGS. 2A and 2B show non-oxidized (2A) and partially oxidized (2B) forms of the FIG. 1 structure, where n=4 and the subunit is chromotropic acid.

FIG. 1 shows the general structural formula of a macrocyclic compound composed of substituted naphthalene subunits, for use in the present invention. One exemplary compound of this type is shown in non-oxidized (I) and partially oxidized (II) form in FIGS. 2A and 2B, respectively. The compound is a tetramer of chromotropic acid (1,8-dihydroxy, 3,6-disulfonic acid naphthalene) subunits linked by methylene or methine (>$CH_2$ or ≧CH) bridges ($R_4$). As seen, the methylene bridges and the "interior" ring atoms (ring positions 1, 2, 7, and 8) form a continuous chain having $R_1$=OH or =O groups attached at the 1 and 8 positions. The non-chain atoms (ring positions 3–6 on each substituent) $R_2$=sulfonic acid substituents on the 3 and 6 ring atoms. The nature of the partially oxidized structure was deduced from $H^1$ and $C^{13}$ NMR studies, and from mass spectroscopy evidence.

Figure 2B:
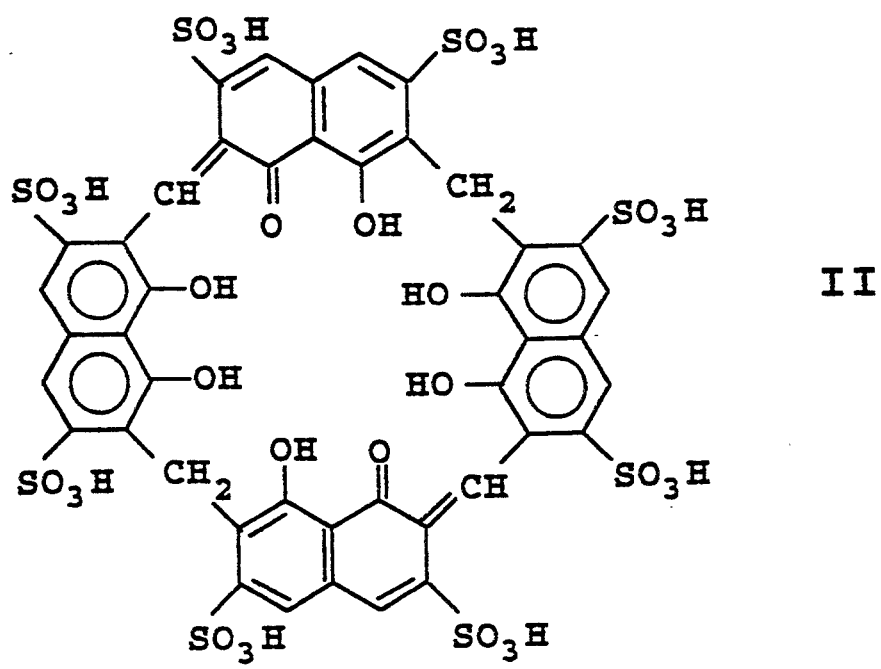

For purposes of the following discussion, and for illustrating synthetic routes, usually only the non-oxidized subunit form of the compound is given. It will be understood that the compound may be partially oxidized, after exposure to air under heat and acidic conditions, i.e., contain one or more $R_1$ ketone (=O) groups, and a double bond between the ring and the associated bridge methylene group, as indicated in FIG. 2B. It will also be understood that the same reaction mechanisms will apply generally to the partially oxidized form of the compound, i.e., the structure shown in FIG. 2B, or similar structures containing additional $R_1$=O groups, except that $R_1$ modification reactions will typically selectively modify an $R_1$ —OH group, and leave the corresponding $R_1$=O group intact.

As will be seen below, the compound preferably includes the chromotropic acid derivatives in which $R_1$ is a polar substituent, such as OH, =O, $CO_2H$ or an ether, thioether, ester, or thioester linked alkyl or aryl group, and combinations of these group, e.g., where only the OH groups in the partially oxidized structure are substituted by one of the above groups.

$R_2$, as noted, is a sulfonic acid-derived substituent which may be sulfonic acid, as shown in FIG. 2, a sulfonate salt, sulfinic acid (—$SO_2$), and sulfinate salts, a sulfonate or sulfonate ester or sulfonamides.

$R_3$ is H or an uncharged or negatively charged substituent, but subject to the activity constraints discussed below.

Also as will be seen below, the $R_4$ bridge linking the chromotropic acid derivative subunits is preferably of the form >CHR or ≧CR (indicating unsaturated bridges in the partially oxidized form), where R is H or a small carbon-containing group, such as lower alkyl, alkenyl, ketone, or carboxylic acid group, or aryl group. The bridge may also be of the form —$CH_2NR'CH_2$—, where R' is similarly H or a small carbon containing group, such as a lower alkyl group.

Alternatively, the bridges in the macrocycle may be ring structures, including aryl ring structures, such as in the dimeric macrocycle shown in FIG. 4, or analogous structures formed by bridging through heterocyclic rings, such as pyrole or furan rings.

The number of subunits may vary from 4 (e.g., FIG. 2A structure) to 8, with macrocycles containing 4, 6 and 8 subunits being preferred. In the reaction schemes described below, the macrocycle formed may include mixtures of compounds with different subunit numbers (n) values, e.g., a dominant n=4 structure (4 subunits) with additional structures containing 6 and 8 subunits.

Representative macrocyclic compounds which have been synthesized and tested for anti-viral activity are identified by their $R_1$, $R_2$, $R_3$, and $R_4$ substituents in Table 1 below. The KY and Y number in the lefthand column in the table refers to the analog designation of the corresponding compound. For example, the compound in which $R_1$ is OH, $R_2$ is $SO_2NH_2$, $R_3$ is H, and $R_4$ is —$CH_2$— is designated KY-3. Although not shown in the table, the compounds may exist in a partially oxidized state in which one of more $R_1$ groups are =O, and adjacent bridges contain a double-bond carbon linkage to the ring.

TABLE 1

| KY | $R_1$ | $R_2$ | $R_3$ | $R_4$ |
|---|---|---|---|---|
| KY-1 | OH | $SO_3Na$ | H | >$CH_2$ |
| KY-3 | OH | $SO_2NH_2$ | H | >$CH_2$ |
| KY-42 | OH | $SO_3Na$ | H | >$CHCO_2H$ |
| KY-48 | OH | $SO_3Na$ | H | >$CHCHOHCH_2OH$ |
| KY-85 | OH | $SO_3Na$ | OH | >$CHC_6H_6$ |
| KY-97 | OH | $SO_3Na$ | H | >$CH_2CH=CH_2$ |
| KY-110 | OH | $SO_3Na$ | H | >$CHC(O)CH_3$ |
| KY-121 | OH | $SO_2C_6H_3(OH)_2$ | H | >$CH_2$ |
| KY-123 | OH | $SO_2Na$ | H | >$CH_2$ |
| KY-143 | OH | $SO_3Na$ | OH | >$CH_2$ |
| KY-147 | OH | $SO_2NHCH_3$ | H | >$CH_2$ |
| KY-148 | OH | $SO_2NHEt$ | H | >$CH_2$ |
| KY-151 | $OCH_3$ | $SO_3Na$ | H | >$CH_2$ |
| KY-158 | OH | $SO_2CH_3$ | H | >$CH_2$ |
| KY-171 | OH | SH | H | >$CH_2$ |
| KY-175 | OH | $SO_3CH_3$ | H | >$CH_2$ |
| KY-176 | OH | $SO_2NHC_6H_6$ | H | >$CH_2$ |
| KY-193 | OH | $SO_3Na$ | Br | >$CHBrCH_2Br$ |
| KY-194 | OH | $SO_3Na$ | Br | >$CH_2$ |
| KY-270 | $OCOCH_3$ | $SO_3Na$ | H | >$CH_2$ |
| KY-272 | $OCOCH_3$ | $SO_3Na$ | H | >$CHCO_2H$ |
| KY-276 | OCOEt | $SO_3Na$ | H | >$CH_2$ |
| KY-277 | COEtCl | $SO_3Na$ | H | >$CH_2$ |
| KY-280 | $OCH_3$ | $SO_3Na$ | H | >$CH_2$ |
| KY-281 | $OCOC_3H_7$ | $SO_3Na$ | H | >$CH_2$ |
| KY-284 | $OCH_3$ | $SO_3Na$ | H | >$CHCO_2H$ |
| KY-285 | $OCOCH_3$ | $SO_3Na$ | H | >$CH_2$ |
| KY-288 | OCOPr | $SO_3Na$ | H | >$CH_2$ |
| KY-289 | $OCOC_4H_9$ | $SO_3NH_4$ | H | >$CH_2$ |
| KY-290 | OCOBu | $SO_3Na$ | H | >$H_2$ |
| KY-291 | $OCOC_5H_{11}$ | $SO_3NH_4$ | H | >$CH_2$ |
| KY-293 | $OCOCH=CHCH_3$ | $SO_3NH_4$ | H | >$CH_2$ |
| KY-294 | $OCO(CH_2)_6CO_2H$ | $SO_3NH_4$ | H | >$CH_2$ |
| KY-307 | $O(CH_2)_5CO_2H$ | $SO_3NH_4$ | H | >$CH_2$ |
| KY-346 | OH | $SO_3Na$ | H | —$CH_2N(CH_3)CH_2$— |
| KY-352 | OH | $SO_3NHC_6H_{11}O_5$ | H | >$CH_2$ |

TABLE 1-continued

| KY | $R_1$ | $R_2$ | $R_3$ | $R_4$ |
|---|---|---|---|---|
| KY-357 | OH | $SO_2NHCHC_2CO_2Na$ | H | $>CH_2$ |
| KY-359 | OH | $SO_2NHOH$ | H | $>CH_2$ |
| KY-395 | $OCH_3$ | $SO_3Na$ | H | $-CH_2N(CH_3)CH_2-$ |
| KY-397 | $OCH_3$ | $SO_2NH_2$ | H | $>CH_2$ |
| KY-398 | $OCH_3$ | $SO_2NHCH_2CO_2H$ | H | $>CH_2$ |
| KY-399 | $OCH_3$ | $SO_2NHCH_2CO_2H$ | H | $-CH_2N(CH_3)CH_2-$ |
| Y-20 | OH | $SO_3Na$ | H | $-CH_2C_4H_2OCH_2-$ |
| Y-34 | OH | $SO_3Na$ | H | $-CH_2C_6H_4CH_2$ |
| Y-66 | OH | $SO_3Na$ | H | $>CHCO_2H$ |
| KYY-19 | OH | $SO_2NHCH(CH_2)_2(CO_2H)_2$ | H | $>CH_2$ |

FIGS. 3A and 3B illustrate two preferred synthetic methods for preparing macrocyclic chromotropic acid compounds. The method illustrated in FIG. 3A involves cyclization of a chromotropic acid derivative (including chromotropic acid itself) with an aldehyde (RCHO) to form a macrocyclic compound, such as the tetramer shown FIG. 2, in which the chromotropic acid subunits are linked by R-substituted methylene groups, i.e., in which $R_4$ is $>CHR$ (including $\geq CR$). This synthetic scheme provides a convenient method for constructing macrocyclic compounds having a variety of different bridge-methylene R groups, by carrying out the cyclization reaction in the presence of an aldehyde of the form RCHO.

For example, to construct a macrocyclic compound with a $-CH_2-$ bridge, such as the KY-1 compound (IV), chromotropic acid (III) is reacted with formaldehyde. Typical reaction conditions are given in Example 1A for the synthesis of KY-1. Similarly, KY-42 is prepared by cyclization with glyoxylic acid (Example 1C); KY-48, in the presence of glyceraldehyde; KY-85, in the presence of benzaldehyde; KY-97, in the presence of acrolein; and KY-110, in the presence of pyruvic aldehyde. It will be appreciated that a variety of other RCHO aldehydes having small alkyl, alkenyl, acid and other hydrocarbon R groups would be suitable. Further, the R bridge group may be further modified after the cyclization reaction. For example, KY-193 may be prepared by bromination of the KY-97 compound.

Figure 4A:
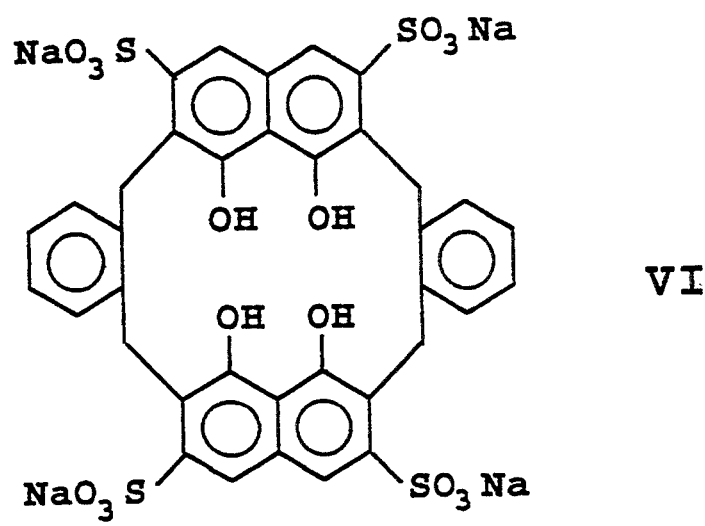
FIGS. 4A and 4B show an unoxidized (4A) and partially oxidized (4B) macrocycle with mixed phenyl and sulfonated naphthalene subunits.
Figure 4B:
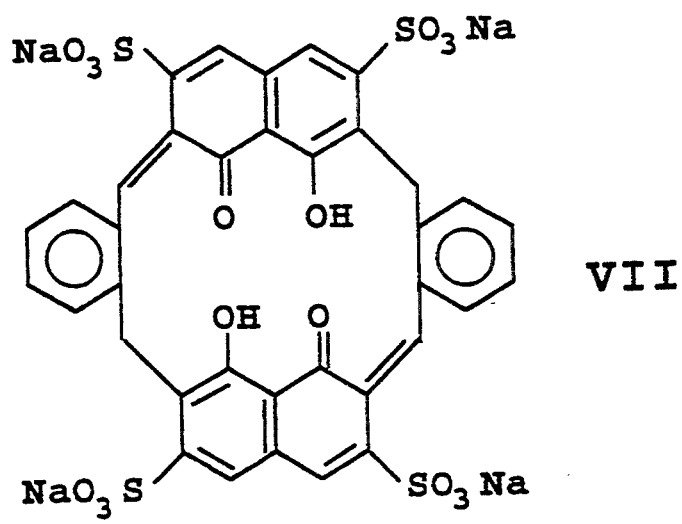
Figure 5:
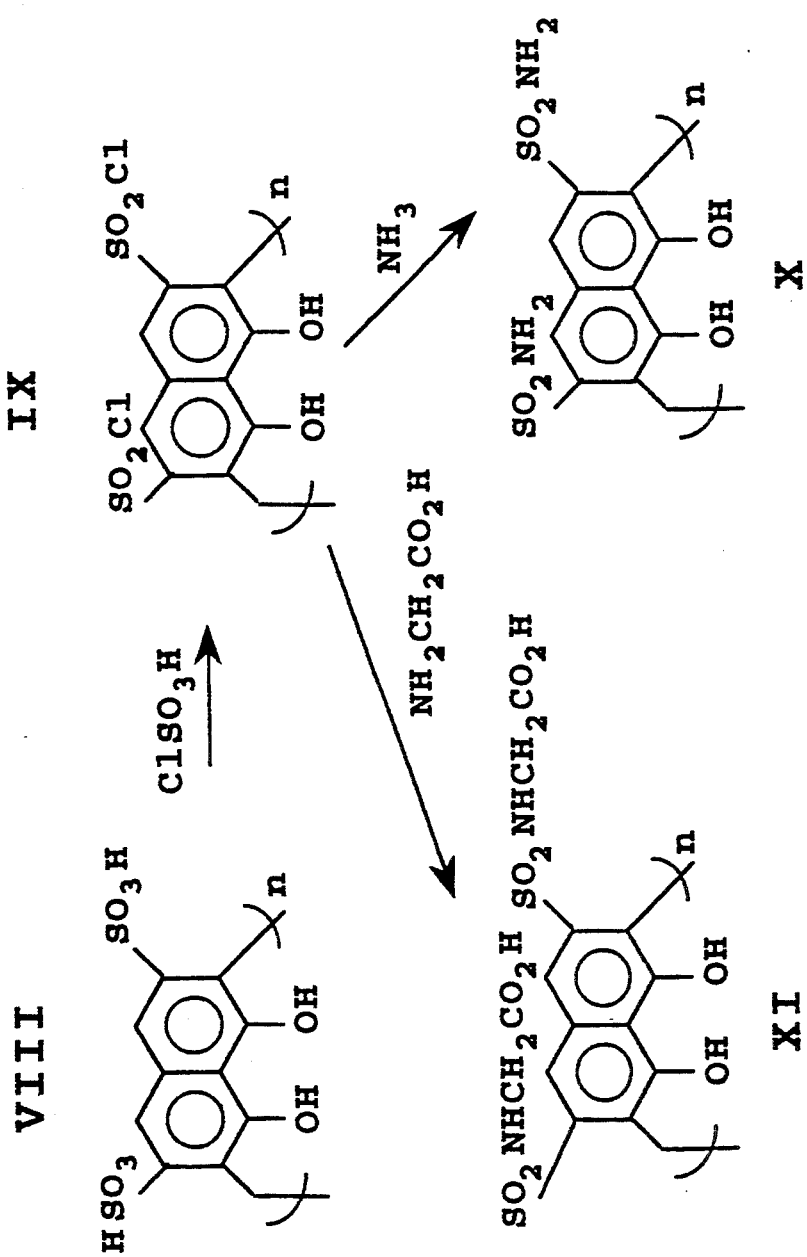
FIG. 5 illustrates reaction methods for converting the sulfonic acid substituents of macrocyclic chromotropic acid to glycyl sulfonamide and sulfonamide groups.
Figure 6:
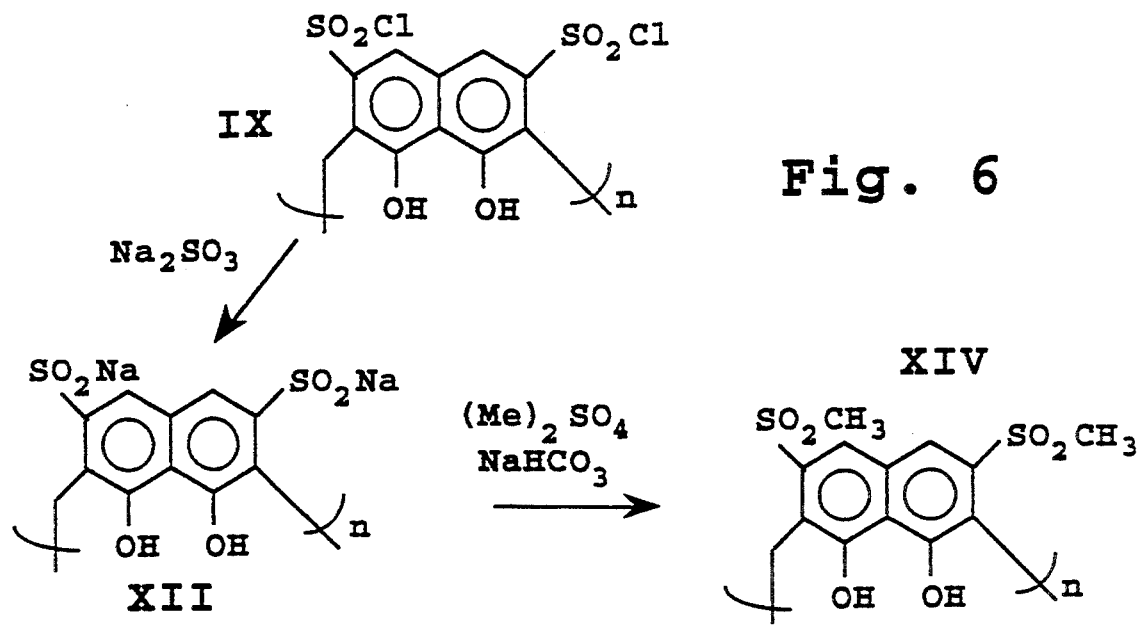
FIG. 6 illustrates a reaction method for converting the sulfonic acid residues of macrocyclic chromotropic acid to a sulfinic acid (sodium salt) or its methyl (aryl) ester.

In the method illustrated in FIG. 3B, cyclization of the chromotropic acid derivatives (III) is carried out by reaction with hexamethylenetetramine, to form a 3-atom chain bridge of the type $-CH_2N(CH_3)CH_2-$ (V). The cyclization reaction for the synthesis of KY-346 is given in Example 1J. The $-CH_2N(CH_3)CH_2-$ bridge may be modified, after the cyclization reaction, to form a variety of N-substituted bridges of the $-CH_2(R')CH_2-$, where R' is one of a variety of small carbon-containing groups, according to known synthetic methods. Some of the bridges in the partially oxidized structure will have the form $=CHN(R')CH_2-$. As noted above, the FIG. 4A compound (VI) is representative of macrocyclic naphthalene having a cyclic bridge, in this case a phenyl bridge. The compound is formed by reacting chromotropic acid, in the presence of hydrochloric acid with 1,2-benzenedimethanol in acetic acid, as detailed in Example 3. Similar methods can be employed to linked chromotropic acid subunits by other cyclic bridges, such as furan, pyrole, and the like. FIGS. 4A and 4B show the non-oxidized (VI) and partially oxidized (VIII) forms of the compound). For synthesis of macrocyclic compounds with selected R1, $R_2$, $R_3$ and $R_4$ substituents, two general approaches are available. In one approach, the chromotropic acid derivative is modified after cyclization so that the cyclized product will either contain the selected $R_1$, $R_2$, and $R_3$ and $R_4$ substituent, or contain a substituent which can be readily modified to the selected substituent. This approach is illustrated by the synthesis of KY-3, which has an $SO_2NH_2R_2$ substituent, as detailed in Example 1B. Here cyclized chromotropic acid (VIII) is reacted first with chlorosulfonic acid, to form the corresponding $R_2 =SO_2Cl$ derivative (IX, FIG. 5). The macrocyclic compound is then reacted with ammonia water to form the desired $R_2=SO_2NH_2$ derivative (X, FIG. 5). A similar strategy was employed for the synthesis of KY-357 ($R_2 =SO_2NHCH_2CO_2H$) by final subunit reaction with glycine (XI, FIG. 5), at basic pH. FIG. 6 illustrates the conversion of sulfonyl groups of cyclized chromotropic acid to sulfinate sodium salt (XII) and alkyl sulfonate ester (XIV). The first stage of the reaction involves the formation of the corresponding sulfonyl chloride derivative (IX), as outlined above. This compound is then treated with sodium sulfite, to form the corresponding a sulfinate salt (XII). Reaction with dimethyl sulfate in the presence of sodium bicarbonate produces the corresponding methyl sulfonate ester (XIV). Similarly, macrocyclic compounds with a variety of $R_1$ substituents may be prepared by modification of chromotropic acid after cyclization. In synthesizing KY-151, for example, ($R_1 =OCH_3$) cyclized chromotropic acid is reacted with dimethylsulfate under basic conditions, as detailed in Example if, to form the dimethylether of cyclized chromotropic acid. Similarly, in preparing KY-307 ($R_1 =O(CH_2)_5CO_2H$), cyclized chromotropic acid is first converted to the diether of hexanoic acid by initial reaction of cyclized chromotropic acid with 6-bromohexanoic acid under basic reaction conditions. As further examples, in preparing compounds such as KY-272 and KY-294, in which $R_l$ has the form OCOR, the macrocyclic compound formed by cyclization of chromotropic acid is reacted with an acid chloride of the form RCOCl, under basic conditions, as detailed in Example 1J for the synthesis of KY-285.

In a second general approach, the selected substituent is formed on the subunit naphthalene rings by derivatization of the naphthalene subunit, with subsequent subunit cyclization to form the desired macrocycle. For the synthesis of KY-175 ($R_2=SO_3CH_3$), chromotropic acid is reacted with sulfonylchloride, as above, to produce the corresponding $R_2 =SO_2Cl$ substituents. Further reaction with $NaOCH_3$ leads to the desired $R_2$ substituent. Reaction details are given in Example 1H.

It will be appreciated that the synthetic method for forming selected-substituent macrocyclic compounds may include both prior derivatization of chromotropic acid and subsequent derivatization of the subunits after cyclization. For example, in forming KY-397 ($R_1 =OCH_3$, $R_2 =SO_2NH_2$), chromotropic acid subunits are first reacted at the $R_1$ positions, to form the dimethyl ether derivative as described above. After cyclization with formaldehyde, the compound is further derivatized at the $R_2$ position, also as described above, to convert the $SO_3$ group to the desired $SO_2NH_2$ substituent.

The KY compounds described above can be converted readily to a variety of sulfonic acid or sulfonate salts, by reaction in acid or in the presence of a suitable salt, according to well known methods. Thus, for example, several of the KY compounds shown in Table 1 are ammonium salts formed by cation exchange of protons in the presence of an ammonium salt, such as ammonium chloride. In addition, exposure of the macrocyclic compound to a variety of metal cations, such as the cations of Ca, Ba, Pt, Cu, Bi, Ge, Zn, La, Nd, Ni, Hf, or Pb, may produce both a metal salt and a metal chelate of the macrocyclic compound in which the metal is chelated at interior polar pocket in the compound.

The physical properties of several macrocyclic compounds prepared in accordance with the invention have been studied by absorption and mass spectrometry and by nuclear resonance spectroscopy (NMR), as detailed in Examples 1A, 1B, 1C, and 1J. These compounds include tetrameric macrocyclic compounds, such as indicated in FIG. 2, or mixtures with predominantly tetrameric forms.

B. Calix(n)arene Compounds

Figure 7:
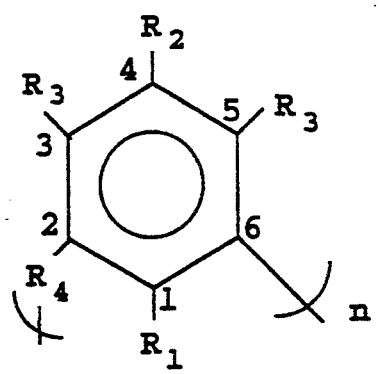
FIG. 7 shows the general structure of a macrocyclic compound composed of phenyl groups with para-position sulfonic acid-derived substitutents, for use in the present invention.
Figure 8:
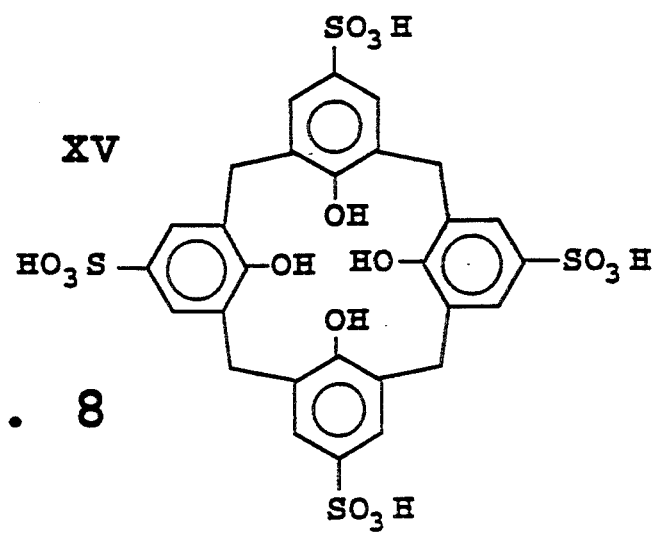
FIG. 8 shows a non-oxidized form of the FIG. 7 structure, where n=4 and the subunit is parasulfonic acid.

FIG. 7 shows the general structural formula of a calix(n)arene compound of the type used in the method of the present invention. One exemplary compound of this type is shown in FIG. 8, which is a tetramer of phenol parasulfonic acid subunits linked by methylene bridges (XV). As seen, the methylene bridges and the "interior" ring atoms (ring positions 2, 1, and 6) form a continuous chain having $R_l$=OH groups attached at the 1 ring positions. The non-chain atoms (ring positions 3–5 on each substituent) have $R_2$=sulfonic acid substituents on the 4 ring atoms.

Figure 9A:
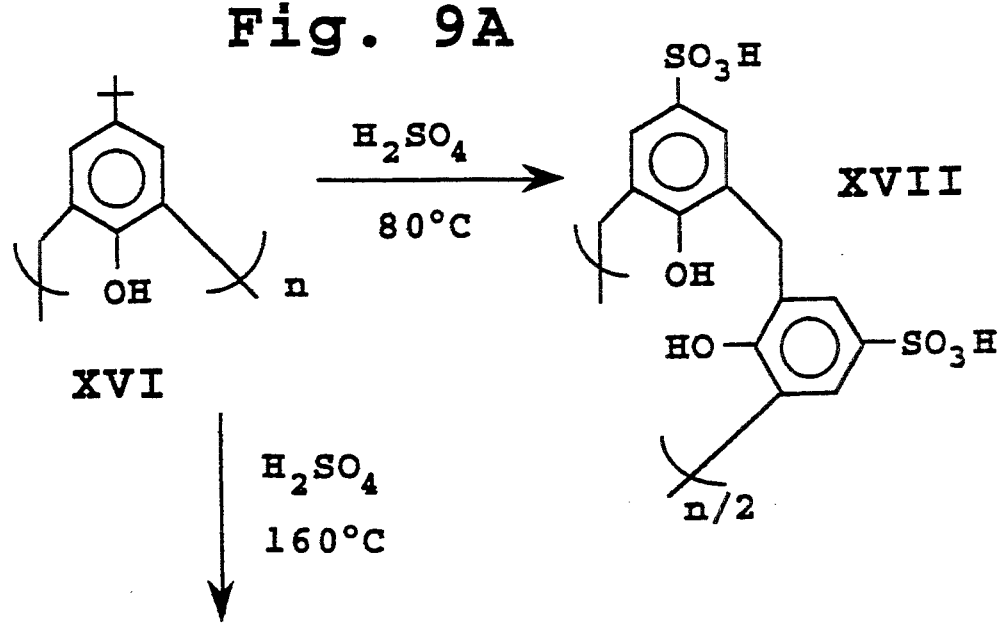
FIGS. 9A and 9B illustrate general methods of synthesis of non-oxidized and partially oxidized forms of the FIG. 8 compound.

FIG. 9A illustrates a general method for forming calix(n)arene compounds. The precursor shown at the left (XVI) is a tert-butyl calix(n)arenes, where n is the number of phenolic subunits (with para-position t-butyl substituents) in the macrocycle, and the bridge connections are methylene groups. t-butyl calixarenes with 4, 6, and 8, subunits are commercially available, and larger and uneven-numbered subunit calix(n)arenes can be prepared by standard purification methods.

In the sulfonation reaction shown in FIG. 9A, a t-butyl calixarene with a selected subunit number is treated with concentrated sulfuric acid, typically for about 4 to 5 hours at 75°–85° C. to effect substantially complete displacement of the 4-position t-butyl group by a sulfonic acid group. Details of the sulfonation reaction are given in Example 2A. The method has been used to produce the n=4 macrocycle compound shown in FIG. 8, and related macrocycles with 6 and 8 phenol subunits.

Figure 9B:
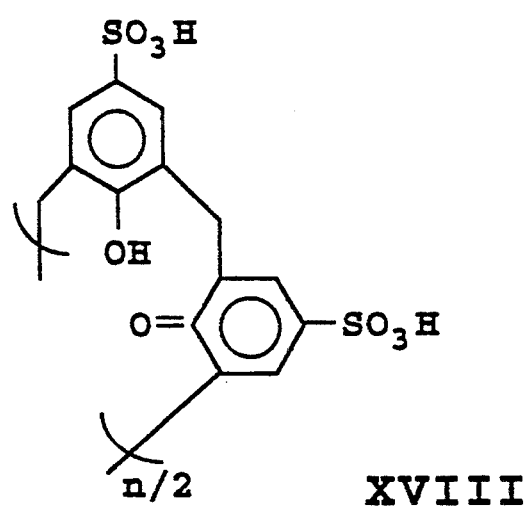

A similar method is used for preparing a sulfonated calixarene with partially oxidized 1-position OH groups, as shown at 9B. Here the t-butyl calixarene starting material is treated with conc. sulfuric acid at a temperature above 100° C., preferably between 150°–170° C. The reaction is effective to sulfonate the subunit rings and to partially oxidize the interior OH groups. As indicated in FIG. 9B, partial oxidation can lead to a conjugated calix(n)arene structure (XVIII) in which bridge contributes delocalized electrons. This conjugated structure is colored, and the development of a colored product can be used to monitor the course of the oxidation reaction. Details of the reaction are given in Example 2B.

Figure 12:
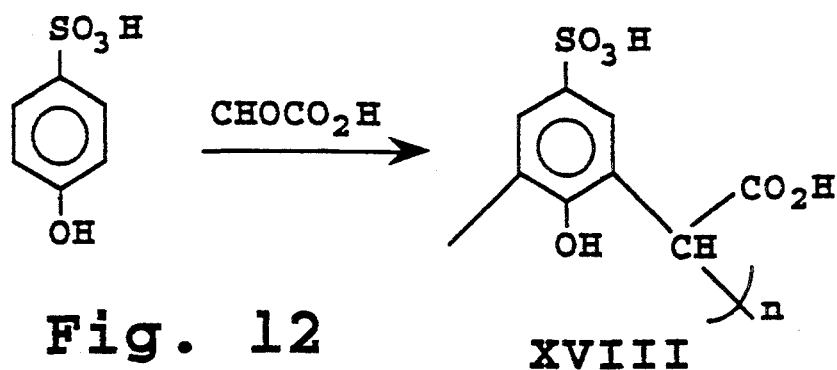
FIG. 12 shows a reaction scheme for producing a macrocylic compound like that shown in FIG. 8 but with carboxylic acid-containing bridge linkages.

It will be appreciated that the desired macrocycle can also be formed directly by reacting parasulfonic acid phenol (or precursors thereof) under suitable bridging conditions, such as described above for producing naphthalene-subunit macrocycles. This is illustrated by the reaction shown in FIG. 12, for production of a macrocyle having carboxylic acid-containing bridge groups. In this method, phenol parasulfonic acid is reacted with glyoxylic acid, under conditions similar to those described in Example 1C, to form the cyclized structure shown (XXII).

Figure 10:
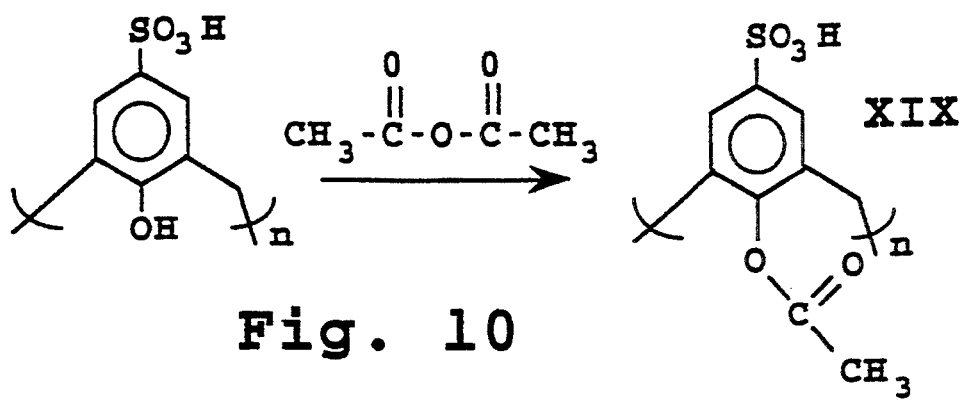
FIG. 10 shows a reaction scheme for replacing the ring hydroxyl groups in the FIG. 8 compound with acetyl groups.
Figure 11:
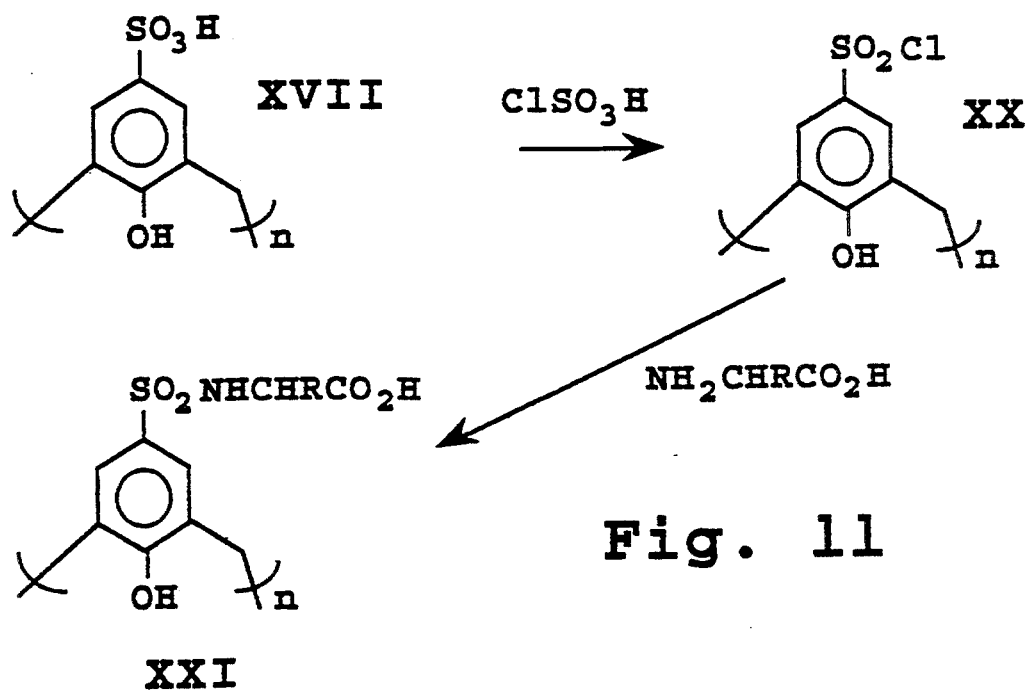
FIG. 11 shows a reaction for converting sulfonic acid substituents to glycyl sulfonamide groups in a phenyl-subunit macrocyclic compound.
Figure 13:
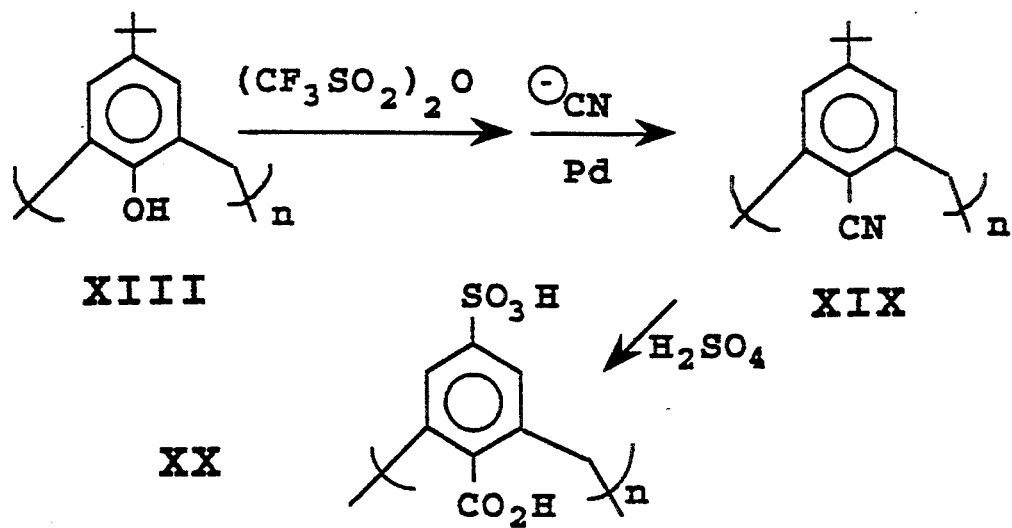
FIG. 13 shows a reaction scheme for replacing hydroxyl groups in the FIG. 8 compound with carboxylic acid groups.

The calix(n)arene compounds formed as above can be modified, according to general procedures outlined in Section IIA above, to achieve selected $R_1$ groups, modified sulfonyl groups, and/or addition of $R_2$ groups. The range of $R_1$ and $R_2$ substituents is substantially the same as that discussed above. FIGS. 10, 11, and 13 illustrate various reaction methods for modifying the $R_1$ group of an already formed macrocycle. In FIG. 10, the sulfonated structure shown in FIG. 8 is treated with acetic anhydride, to form an O-acetyl $R_1$ group. Details of the reaction are given in Example 2C. Since this structure would be expected to undergo hydrolysis in the presence of serum esterases, differences in the activity of the ester compound and the free OH compound would be expected to occur after intravenous (IV) administration. Example 2G describes a similar reaction scheme for forming a toluene sulfonic acid ester at the $R_1$ position.

FIG. 11 illustrates a general method for forming sulfonamides, such as glycylsulfonamide (XXI) of the FIG. 8 compound. Analogous to the reactions described with respect to FIG. 5, the sulfonated phenyl calix(n)arene compound (XVII) is treated with chlorosulfonic acid, to form the corresponding sulfonyl chloride analog (XX). Further reaction with a selected amine, in this case glycine, gives the desired sulfonamide. Reaction details are given in Example 2D for the synthesis of the $R_2$=$SO_2NH_2$ compound and in Example 2E, for the synthesis of the glycyl sulfonamide compound.

FIG. 13 depicts a general non-exclusive synthetic method for a net substitution of $R_1$=OH by $R_1$=carbon moieties. In Example 2H, the reactions detail a process from which a substrate ($R_1$=OH, $R_2$=tert-butyl, $R_4$=$CH_2$, n=4) affords an intermediate ($R_1$=CN, $R_2$=tert-butyl, $R_4$=$CH_2$, n=4). Further modification then provides the product ($R_1$=$CO_2H$, $R_2$=$SO_3H$, $R_4$=$CH_2$, n=4).

It will be appreciated that substituent modifications at the $R_1$ site can be selectively carried out at OH sites in the partially oxidized macrocycle, such as the structure shown at FIG. 9B. That is, reactions which are specific for ring OH groups will leave the =O group intact, thus providing a mixed $R_1$ group containing =O groups.

The $R_3$ is generally H, but may be an uncharged or negatively charged substituent, similar to the $R_3$ group described in Section IIA above.

The $R_4$ bridge linking the chromotropic acid derivative subunits is preferably of the form >CHR or ≡CR, where R is H or a small carbon-containing group, such as lower alkyl, alkenyl, ketone, or carboxylic acid group, or aryl group, as noted above, or of the form —$CH_2NR'CH_2$—, where R' is similarly H or a small carbon containing group, such as a lower alkyl group. Alternatively, the bridges in the macrocycle may be ring structures, including aryl ring structures, analogous to the dimeric macrocycle shown in FIG. 4.

Also as above, the number of subunits may vary from 4 (e.g., FIG. 4 structure) to 8, with macrocycles containing 4, 6 and 8 subunits being preferred. In the reaction schemes described below, the macrocycle formed may include mixtures of compounds with different subunit numbers (n) values, e.g., a dominant n=4 structure (4 subunits) plus additional structures containing 5–8 subunits.

Representative calix(n)arene compounds which have been synthesized and tested for anti-viral activity are identified by their $R_1$, $R_2$, and $R_4$ substituents in Table 2 below. The KY and Y number in the lefthand column in the table refers to the analog designation of the corresponding compound, as in Table 1. Compounds which are partially oxidized at the $R_1$ position, and have which may have both saturated and unsaturated bridge methylene carbon groups are indicated as in Table 1.

TABLE 2

| Compound | $R_1$ | $R_2$ | $R_4$ | n |
|---|---|---|---|---|
| Y-1 | OH | $SO_3$ | $-CH_2-$ | 8 |
| KY-226 | O/OH | $SO_3$ | $-CH_2/=CH-$ | 8 |
| Y-49 | OH | $SO_3$ | $-CH_2-$ | 4 |
| KY-225 | O/OH | $SO_3$ | $-CH_2/=CH-$ | 4 |
| Y-77 | OH | $SO_3$ | $-CH_2$ | 6 |
| Y-48 | O/OH | $SO_3$ | $-CH_2/=CH-$ | 6 |
| KY-268 | O/OH | $SO_3$ | $-CH_2/=CH-$ | 3 |
| KY-269 | $O/CO_2CH_3$ | $SO_3$ | $-CH_2/=CH-$ | 4 |
| KY-271 | $O/CO_2CH_3$ | $SO_3$ | $-CH_2/=CH-$ | 3 |
| Y-78 | O/OH | $SO_2NH_2$ | $-CH_2-$ | 8 |
| Y-100 | O/OH | $SO_2OCH_3$ | $-CH_2-$ | 8 |

The compounds shown in Table 2, and R-group combinations thereof, described above can be converted readily to a variety of sulfonic acid or sulfonate salts, by reaction in acid or in the presence of a suitable salt, according to well known methods, as described above.

C. Calix(n)arene Compounds with Sulfonate, Phosphonate, and Carboxylate Groups. One general class of calix(n)arene compounds which are useful in treating enveloped viruses, in accordance with the present invention, are calix(n)arene compounds in which the ring position meta to the bridge attachments, i.e., 4-position carrying substituent $R_2$ in FIG. 7, is substituted with a polar substituent having a terminal sulfonic acid, phosphonic acid or carboxylic acid group. Included are polar substituents which terminate in a sulfonic acid ester or amide, a phosphonic acid ester or amide, or a carboxylic acid ester or amide, as defined above, where the ester and amide groups are cleavable, in vivo to form the corresponding acid group.

Methods for preparing calix(n)arene compounds in which a sulfonic acid is carried at the ring 4 position are given in Examples 2A, 2B, and 2C, including compounds with different substitutions at the ring 1 position. Compounds having sulfonamide group, including a group which terminates with an end terminal carboxyl group are given in Examples 2D and 2E, respectively.

Figure 15:
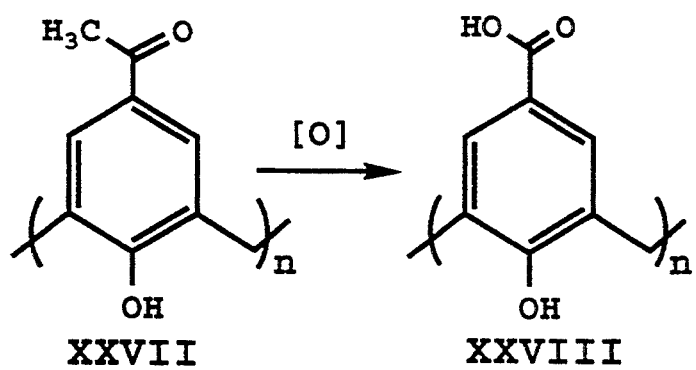
FIG. 15 shows a reaction scheme for preparing a calix(n)arene having para-carboxyl substituents.

FIG. 15 shows the conversion of a calix(n)arene (XXVII) carrying a p-acetyl group to the corresponding calix(n)arene with a p-carboxyl group (XXVIII). Details are given in Example 2K.

Figure 14:
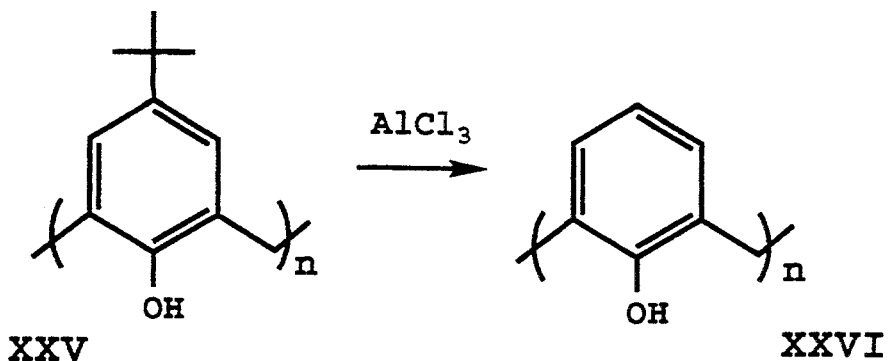
FIG. 14 shows a reaction scheme for producing a calix(n)arene from a para-tert-butyl-precursor.

FIG. 14 illustrates a method for converting a t-butyl calix(n)arene (XXV) to the unsubstituted compound (XXVI), which can be used as a starting material for some of the syntheses described below. Details of the reaction are given in Example 2J.

Figure 16:
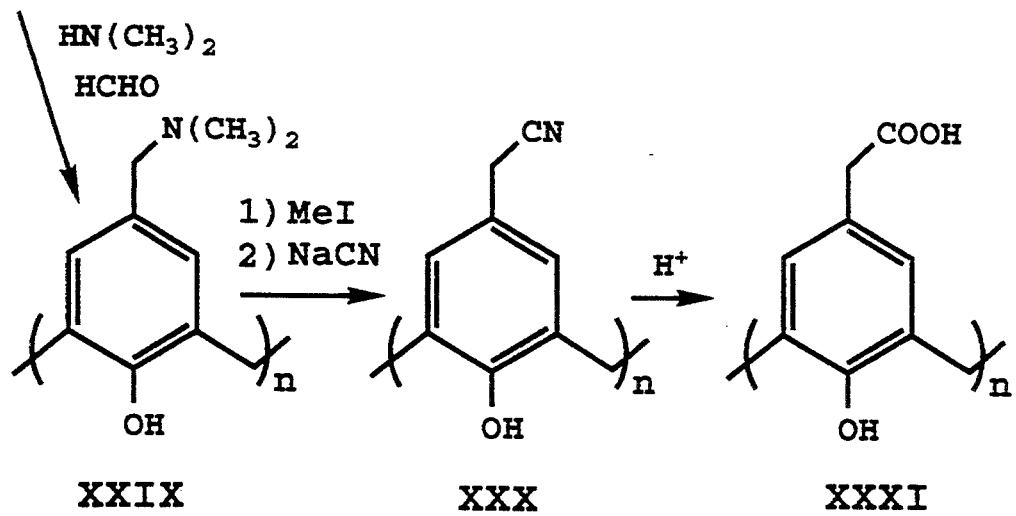
FIG. 16 shows a reaction scheme for preparing a calix(n)arene having carboxyl substituents linked to the para position by a methylene linker.

To form the p-carboxyethyl compound shown at XXXI in FIG. 16, compound XXVI produced above is converted to the corresponding (dimethylaminio)-methyl compound (XXIX) by reaction with dimethylamine and formaldehyde. This compound is then taken to the corresponding cyanomethyl compound (XXX), which when heated in acid, is converted to the desired carboxymethyl compound (XXXI). Details are given in Example 2L.

Figure 17:
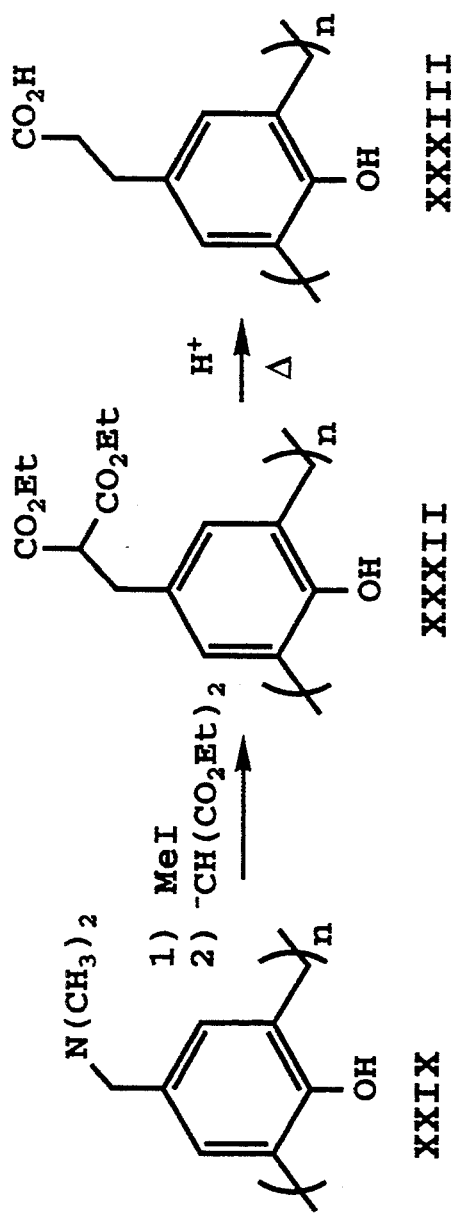
FIG. 17 shows a reaction scheme for preparing a calix(n)arene like that of FIG. 16 but where the carboxyl substituents are linked to the para position by an ethylene linker.

FIG. 17 illustrates the synthesis of a carboxyethyl calix(n)arene (XXXIII). Here the intermediate (XXIX) from above (FIG. 16) is treated sequentially with MeI and the sodium salt of diethylmalonate to give the diethylmalonylmethyl compound (XXXII). Heating in acid gives the desired compound XXXIII. Details are given in Example 2M.

Figure 18:
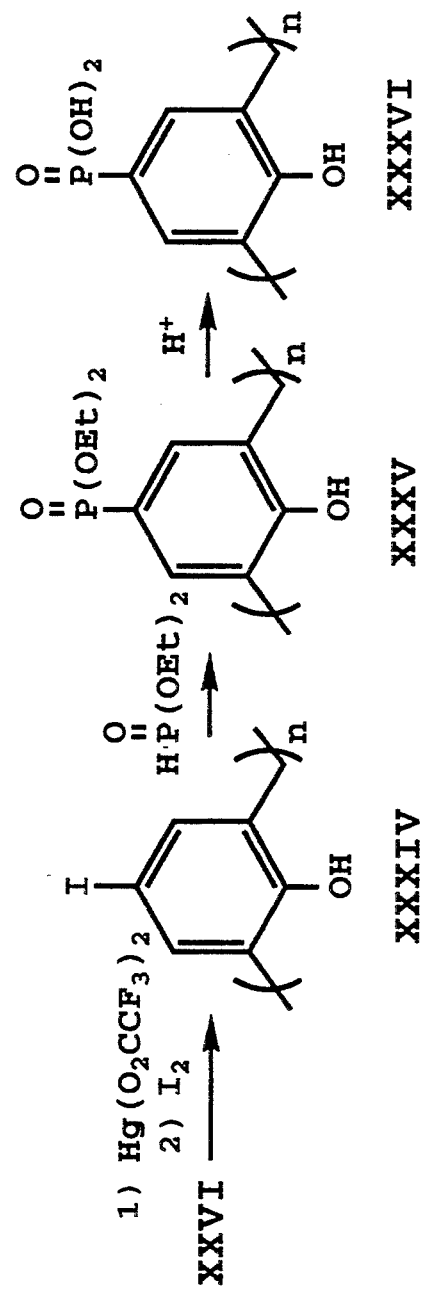
FIG. 18 shows a reaction scheme for preparing a calix(n)arene having para-phosphonate substituents.

FIG. 18 illustrates the synthesis of a p-phosphonate calix(n)arene (XXXVI). In this synthesis, compound XXVI from above is iodinated and then reacted with diethylphosphite to give the diethylphosphonate compound (XXXV). Refluxing in acid gives the desired compound XXXVI. Details are given in Example 2N.

Figure 19:
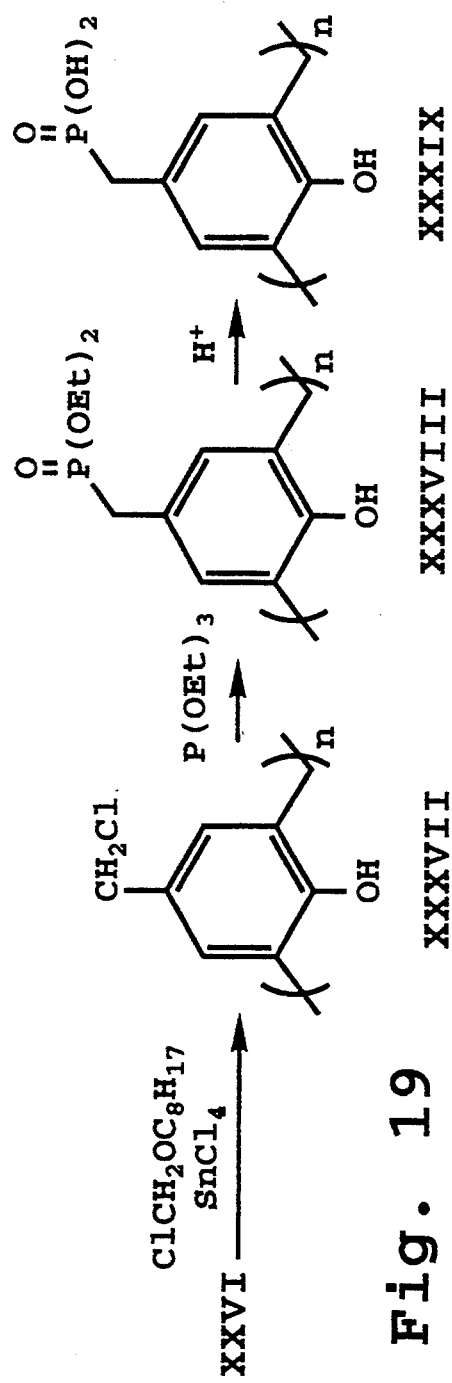
FIG. 19 shows a reaction scheme for preparing a calix(n)arene having phosphonate substituents linked to the para position by a methylene linker.

The synthesis of a phosphonomethyl calix(n)arene (XXXIX) is shown in FIG. 19. As seen, compound XXVI from above is chloromethylated (compound XXXVII), and further reaction with triethylphosphite gives a diethylphosphonyl ester compound (XXXVIII). Heating in acid gives the desired phosphonomethyl compound. Details are given in Example 20. Note that the chloromethyl intermediate is also useful in synthesis of the sulfonylmethyl calix(n)arene analog.

Figure 20:
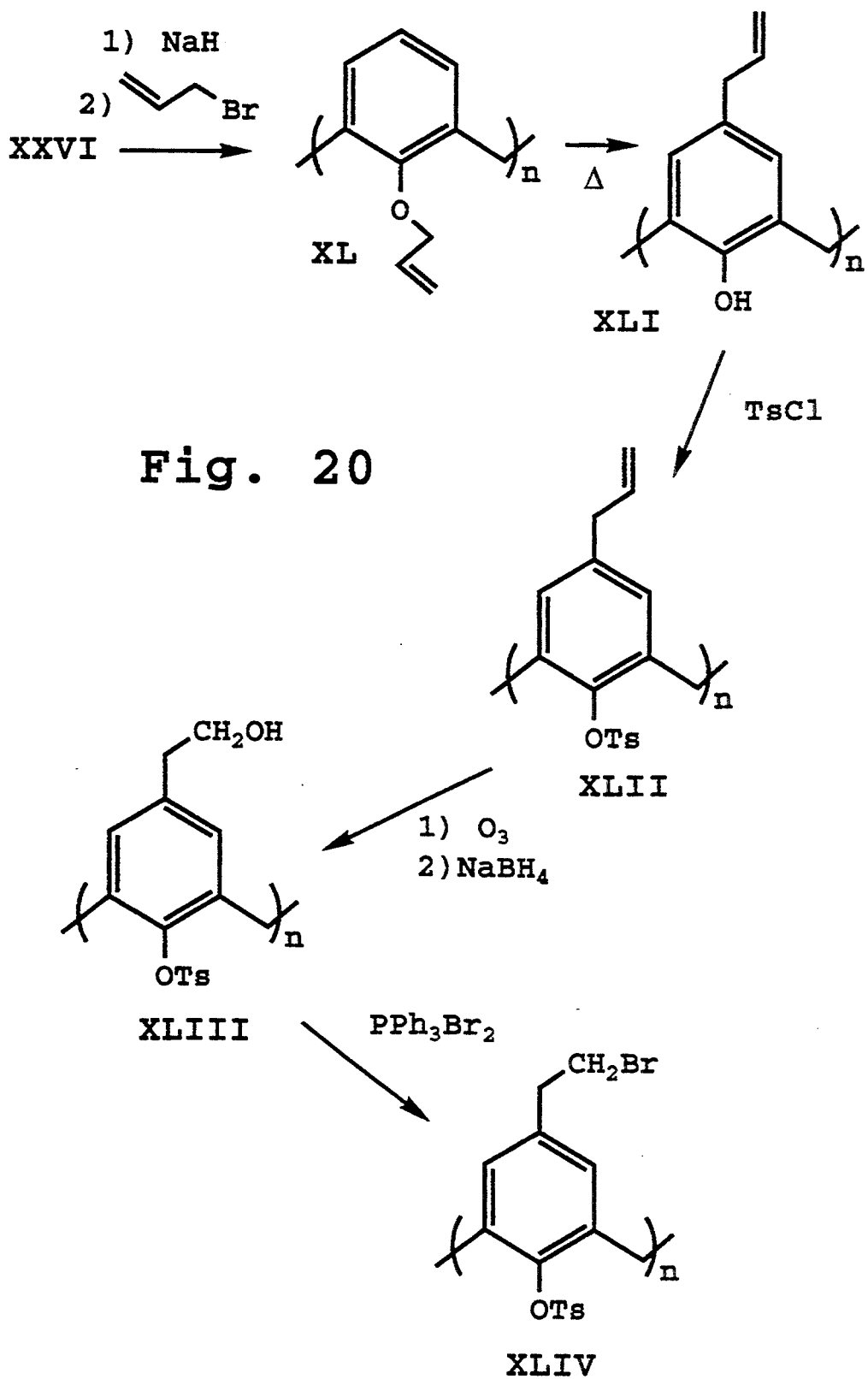
FIG. 20 shows a reaction scheme for preparing a p-2-bromoethyl-O-tosyl-calix(n)arene as a precursor for preparing other calix(n)arene derivatives.

The synthesis of a p-2-bromoethyl compound useful in the synthesis of a phosphonoethyl or sulfonylethyl calix(n)arene is outlined in FIG. 20, with details given in Example 2P. With reference to the figure, compound XXVI from above is allylated at the phenol hydroxyl (compound XL), and heated to give the rearrangement product XLI. Tosylation serves to protect the phenyl hydroxyl position (compound XLII), allowing conversion to the p-hydroxyethyl derivative (XLIII). Further reaction with triphenylphosphine dibromide gives the desired p-bromoethyl XLIV compound.

Figure 21:
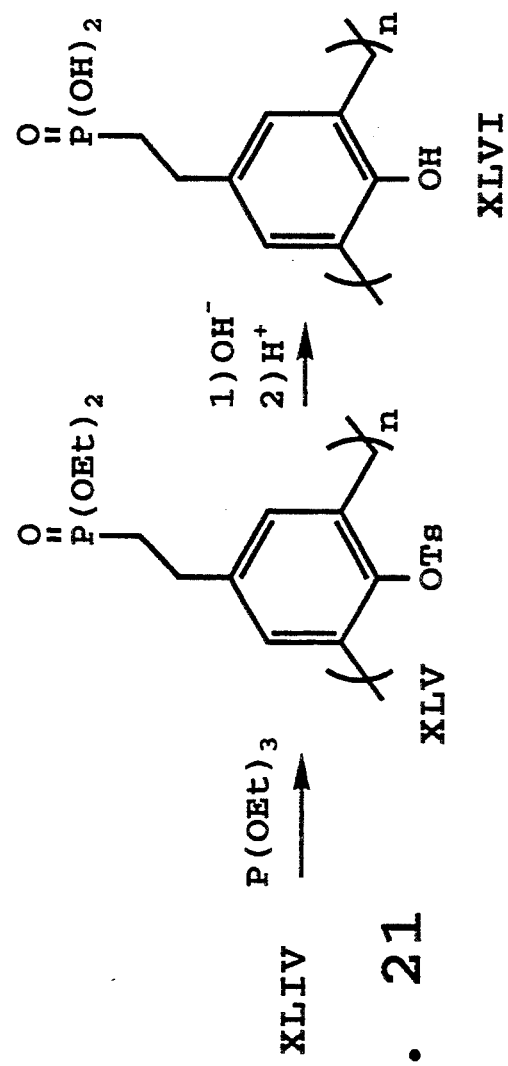
FIG. 21 shows a reaction scheme for using the bromoethyl-calix(n)arene of FIG. 20 to prepare a calix-(n)arene like that of FIG. 19, but where the phosphonate substituents are linked to the para position by an ethylene linker.

The p-bromoethyl calix(n)arene (XLIV) is used in the synthesis of the p-phosphonoethyl compound (XLVI), by a reaction sequence which is analogous to that shown in FIG. 19, described above. Details of the reaction scheme shown in FIG. 21 are given in Example 2Q.

Figure 22:
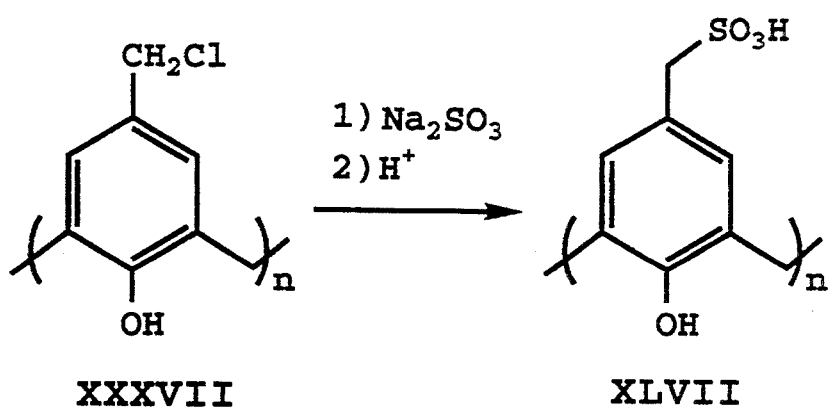
FIG. 22 shows a reaction scheme for preparing a calix(n)arene derivative like that of FIG. 19, but with a sulfonate group instead of a phosphonate group.

The intermediate p-chloromethyl calix(n)arene (compound XXXVII) used above can also be used in the synthesis of a p-sulfonylmethyl calix(n)arene (XLVII), as shown in FIG. 22, with details provided in Example 2R.

Figure 23:
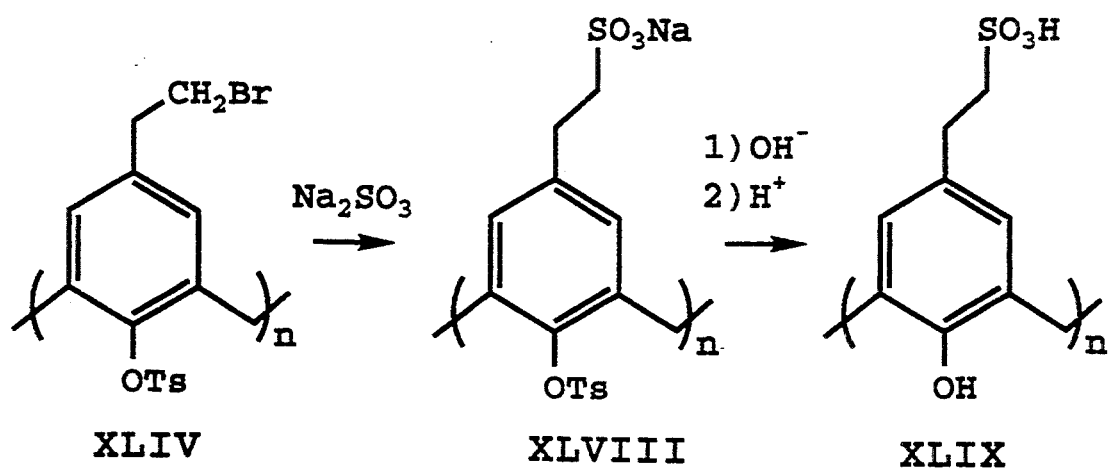
FIG. 23 shows a reaction scheme for preparing a calix(n)arene derivative like that of FIG. 21, but with a sulfonate group instead of a phosphonate group.

Similarly, the p-2-bromoethyl intermediate (XLIV) described above can be used in the synthesis of the p-sulfonylethyl calix(n)arene (XLIX) as shown in FIG. 23, with details given in Example 2S.

The foregoing synthetic methods can be used to produce calix(n)arene compound having at the position meta to the bridge positions (the C4 ring positions), polar substituents which terminate with sulfonic acid, phosphonic acid, and carboxylic acid. The syntheses outlined show both direct acid-group attachment to the rings, or attachment through alkyl linkages, such as methyl and ethyl linkages. It will be appreciated from the discussion below, how acid groups linked to the rings through longer alkyl groups can be prepared. Also, as detailed above, the acid groups can be converted to the corresponding salts.

It will also be appreciated how a variety of esters and amides of the terminal acid groups in the calix(n)arene compounds can be prepared. Generally, the acid esters of carboxylic acid and sulfonic acid can be prepared by standard esterification reactions in which the acid is converted to, for example, an acid chloride, then reacted with an alcohol, such as an alkyl alcohol. The amides of carboxylic and sulfonic acid can similarly be formed by reaction of the acid chloride with an amine, such as an alkyl amine. Preferred esters include aryl and lower alkyl carbonate esters, such as n-butyl alkyl group. Preferred amides include amides of lower alkyl groups.

The conversion of a phosphonic acid calix(n)arene to a corresponding ester or amide likewise follows conventional phosphonate esterification or amidation reaction methods. One method for generating a diethylphosphonyl ester has been described above with reference to FIG. 21.

In addition to the polar substitutents at the C4 position in the calix(n)arene rings, the present invention contemplates, for use in anti-viral treatment, calix(n)arene compounds which are substituted at other ring positions and at the bridge positions in the macrocycle. For example, the C3 and/or C5 ring positions may be substituted with halogens such as F of Cl. Also as described above with respect to several of the naphthyl-ring macrocycles, substitutions at the "inner" ring positions (the C1 ring positions in calix(n)arene) are compatible with anti-viral activity. Also as described above, substitutions at the bridge positions in naphthyl-ring macrocycles are compatible with activity.

Figures 24, 25:
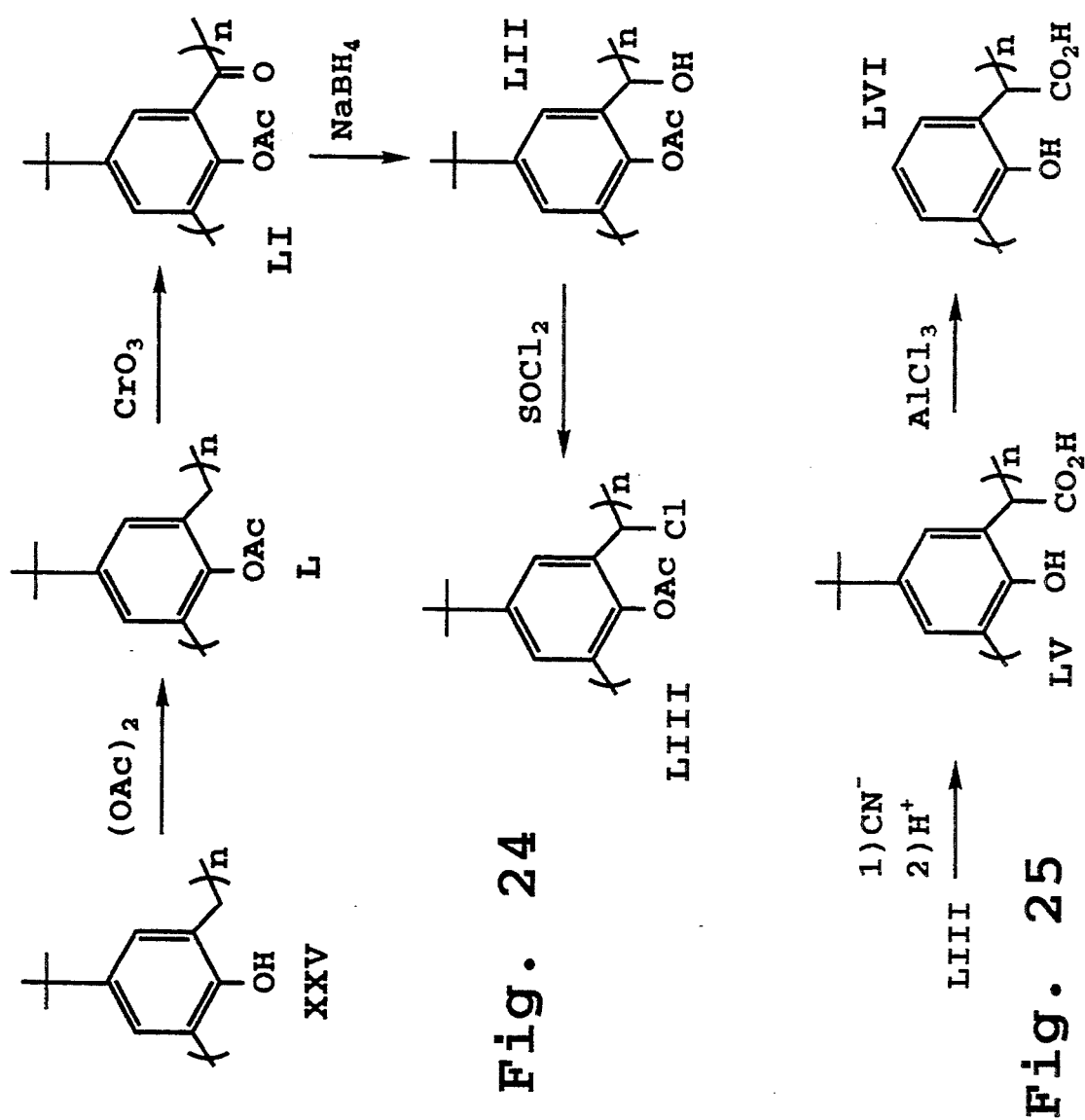
FIG. 24 shows a reaction scheme for preparing a calix(n)arene having a chlorine atom at the methylene bridge for further introduction of other substituents at the methylene bridge.
FIG. 25 shows a reaction scheme for preparing calix-(n)arenes like that of FIG. 12, but starting from the cyclized precursor from FIG. 24.

FIGS. 24 and 25 illustrate one method of attaching carboxyl groups to the bridge methylene in calix(n)arene. In this method, the hydroxyl group of p-t-butyl calix(n)arene (XXV) is acetylated (L), and the product is oxidized at the bridge methylene, to give the bridge ketone (LI). Reduction with sodium borohydride, and subsequent reaction with thionyl chloride yield the compound LIII which is chlorinated at the methylene bridge. Details are given in Examples 2T and 2U.

With reference to FIG. 25, the compound LIII is cyanylated, then treated with acid to form the carboxylic acid group at the bridge methylene. The resulting compound LV can be de t-butylated by treatment with aluminum chloride to give the bridge-carboxylated calix(n)arene shown at LVI. Alternatively, compound LV may be sulfonated, at the C4 ring position, by treatment with sulfuric acid, as above. It will be appreciated that similar methods, but involving initial protection of the bridge carboxyl and/or ring hydroxyl groups, can be used to form corresponding p-phosphonic acid or p-carboxylic acid calix(n)arenes.

Figure 26:
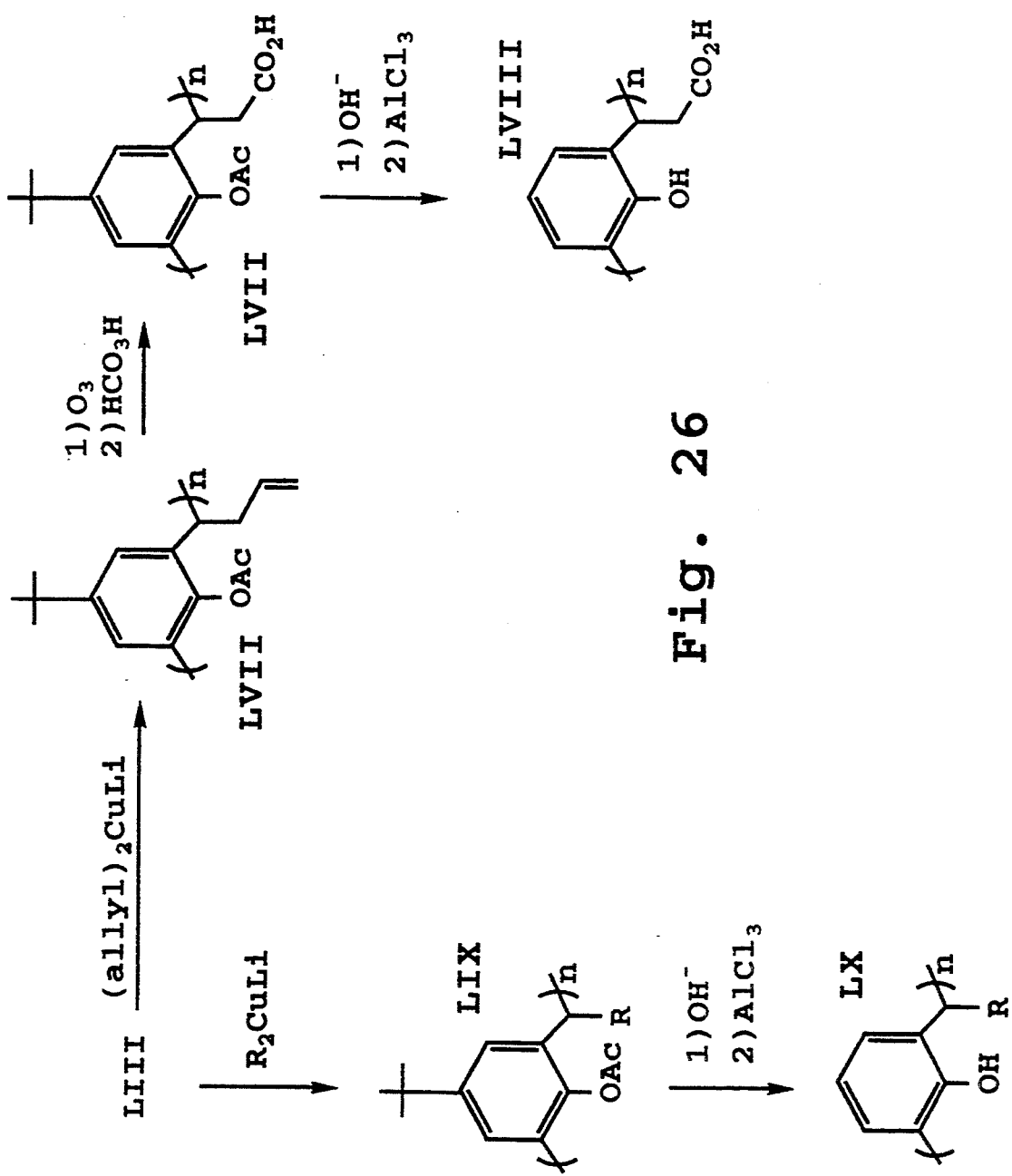
FIG. 26 shows a reaction scheme for preparing a calix(n)arene having a carboxymethyl group attached to the bridge methylene, as well as a general approach for preparing a variety of calix(n)arenes having selected R groups at the methylene bridge, using organocuprate reagents.

Using compound LIII from above, a variety of bridge substitutions can be produced, by the method outlined in FIG. 26, using a suitable cuprate reagent as illustrated at the left in the figure. The reaction at the right in the figure shows how a calix(n)arene LIII can be converted to a compound having a carboxymethyl group attached to the bridge methylene group. Details of this reaction sequence are given in Examples 2W and 2X. The final reaction product (LVIII) can be p-sulfonated or derivatized with other acid groups at the para position as above.

FIG. 27 shows a variety of derivatization reactions involving calix(n)arenes and propane-1,3-sulfone. The reactions are effective to add alkylsulfonate groups at ring hydroxyl positions, as shown. This method provides an alternative approach for producing calix(n)arenes with ring-attached sulfonic acid groups. Reaction details are given in Examples 2Y and 2Z.

Figure 28:
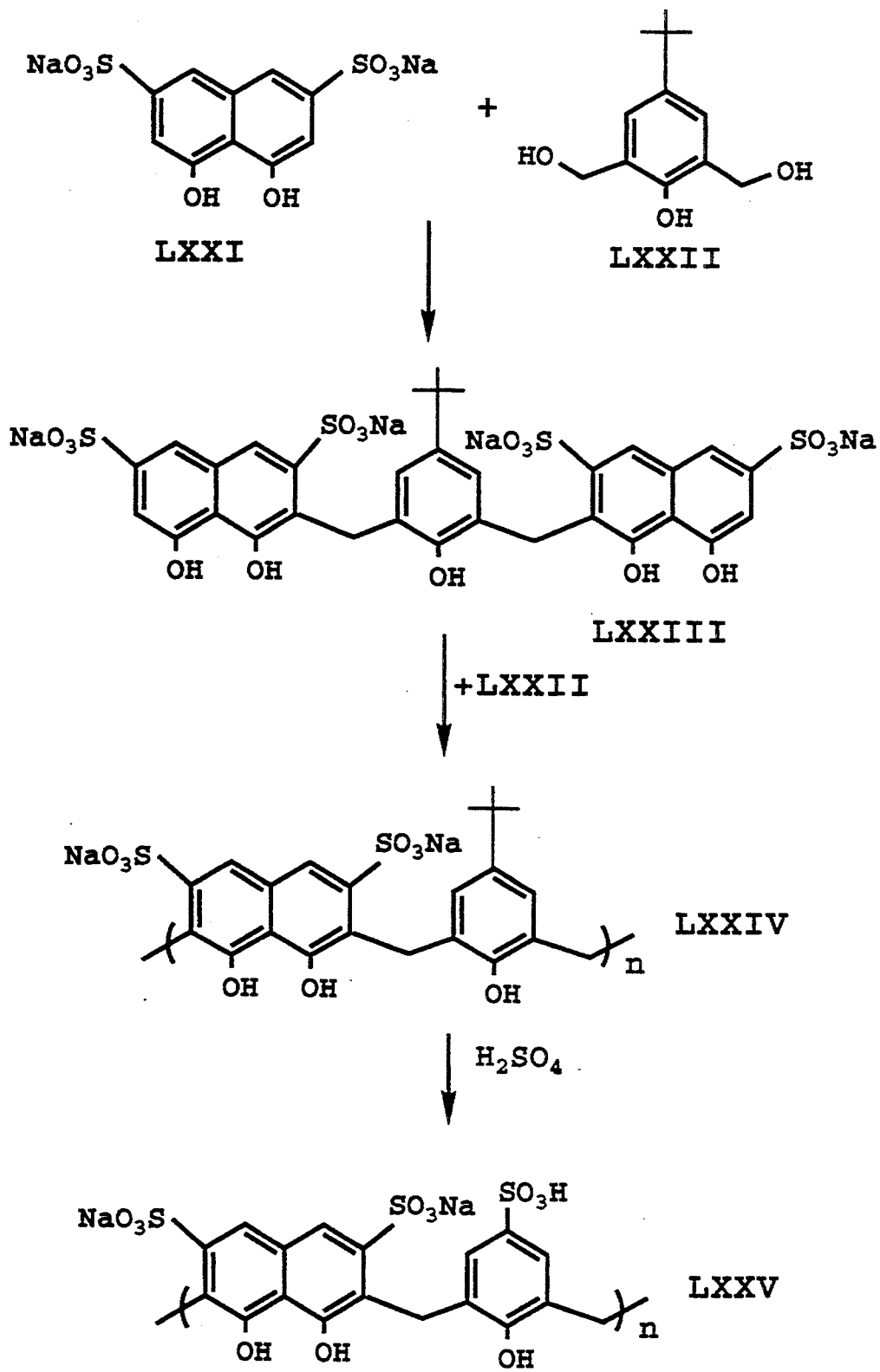
FIG. 28 shows a reaction scheme for preparing a macrocyclic compound having alternating phenyl and naphthyl rings.

Finally, FIG. 28 shows the preparation of a mixed macrocyle containing alternating phenyl and naphthyl groups. The reaction method is described in Example 3B.

III. Inhibition of Virus Infectivity

This section examines the ability of compositions containing a macrocyclic compound to inhibit cell infection by a variety of enveloped viruses. The enveloped viruses which were examined are the herpes viruses, Herpes simplex virus-1 (HSV-1) and herpes simplex virus-2 (HSV-2), which are double-stranded DNA viruses (Roizman); human immunodeficiency virus (HIV), an RNA retrovirus (Popovic; Barre-Simoussi); and influenza A and B and respiratory syncytial viruses (RSV), all RNA viruses (Chanock).

For comparative purposes, selected non-enveloped viruses, including adenovirus, a double-stranded DNA virus (Rowe; Hilleman), and rhinovirus, a single-strand RNA virus (Dick), were examined. Typically, inhibition of virus infectivity was measured by the extent of inhibition of cytopathic effects detectable in infected cultured cells. Inhibition of HSV-1 and HSV-2 infectivity in cultured cells was also shown by inhibition of virus binding to infectable cells, and inhibition of viral plaque formation in infected cells, as described below.

In addition, a large number of representative aryl macrocyclic compounds (including those shown in Tables 1 and 2) were examined for toxicity in cell culture, using a panel of human cell lines, as detailed in Example 4. Briefly, the selected KY- or Y- compound was added to cell cultures at a final concentration of 5, 10, 25, 50, or 100 $\mu$g/ml. Three days later the cells were washed to remove drug, and stained with a vital stain, to determine the percentage of dead cells in each culture. The $IC_{50}$ drug concentration, i.e., value concentration of drug which produced 50% cell death, was 50 $\mu$g/ml for KY-143, KY-151, and KY-163, and 100 $\mu$g/ml or greater for all of the other KY compounds tested. For KY-1, which has a molecular weight of 1404 daltons, a drug concentration of 100 $\mu$g/ml is equivalent to about 66 $\mu$M.

A. Inhibition of HSV Infectivity: Naphthalene-Subunit Compounds

Several compositions containing one of the compounds in Tables 1 and 2 were tested for inhibition of cytopathic effects (CPE's) in cultured, HSV-infected cells. In the method reported in Example 5, Vero cells were infected with HSV-1 or HSV-2 and allowed to grow in culture until cytopathic effects were clearly visible. In the absence of infection, the cells form an even monolayer of fibro-blastlike cells. With HSV infection, a cytopathic effect characterized by round cells in suspension is clearly evident after 24 hours, followed by clumping and lysis of infected cells after 24–72 hours.

In the drug inhibition study reported in Example 5, cells were exposed to HSV-1 or HSV-2 virus and, at the same time, to a selected aryl macrocyclic compound, at a final drug concentration of 10 $\mu$g/ml. Twenty-four hours later the cells were examined for cytopathic effect. If a clear cytopathic effect was not observed with 10 $\mu$g/ml of the drug, the study was repeated at a drug concentration of 20 $\mu$g/ml for some compounds.

Table 3 below lists 50 naphthalene-subunit macrocycles which were tested in this assay. A "+" symbol in the second column indicates that the compound was effective in inhibiting cytopathic effects at 10 or 20 µg/ml. A "−" symbol indicates that CPE was observed at 10 or 20 µg/ml.

TABLE 3

| Compound | CPE 10,20 µg/ml | HSV-1 IC$_{50}$ (µg/ml) | HSV-2 IC$_{50}$ (µg/ml) |
|---|---|---|---|
| KY-1 | + | 2.7 | 1.7 |
| KY-3 | + | 2.4 | 2.5 |
| KY-42 | + | 1 | 3 |
| KY-48 | − | N[1] | N |
| KY-85 | − | N | N |
| KY-97 | + | N | N |
| KY-110 | − | N | N |
| KY-121 | + | 1.5 | 1.8 |
| KY-123 | + | 1.5 | 1.5 |
| KY-129 | + | 1 | 1 |
| KY-143 | − | N | N |
| KY-147 | − | N | N |
| KY-148 | − | N | N |
| KY-151 | + | 1.25 | 1.8 |
| KY-158 | − | N | N |
| KY-171 | + | 2.5 | 3 |
| KY-175 | − | N | N |
| KY-176 | N | N | N |
| KY-193 | GC | N | N |
| KY-194 | + | 1 | 1 |
| KY-280 | + | 2 | 2 |
| KY-272 | + | N | N |
| KY-276 | + | 1.3 | 1.2 |
| KY-277 | + | 1 | 1.2 |
| KY-280 | + | 1.1 | 1 |
| KY-281 | + | 0.5 | 1.5 |
| KY-284 | + | 1 | 1.6 |
| KY-285 | + | 1 | 1.5 |
| KY-286 | + | 2 | 2 |
| KY-288 | + | 1.7 | 2 |
| KY-289 | + | 2.2 | 1.7 |
| KY-290 | + | 1.2 | 1.3 |
| KY-291 | + | 1.4 | 2 |
| KY-293 | + | 1.9 | 2.7 |
| KY-294 | + | 1 | 2.2 |
| KY-301 | + | 1 | 1 |
| KY-307 | + | .8 | 2 |
| KY-308 | + | .9 | 1.2 |
| KY-345 | + | 5 | 6.7 |
| KY-346 | + | 4.4 | 6.2 |
| KY-352 | + | 3.4 | 4.1 |
| KY-357 | + | 4 | 3.3 |
| KY-359 | + | 5.75 | 4.2 |
| KY-376 | + | 2.7 | 1 |
| KY-395 | − | N | 9 |
| Y-4 | + | 5.5 | 6.4 |
| Y-14 | + | 2.5 | 3.5 |
| Y-20 | + | 5 | 3.2 |
| Y-34 | + | 2.5 | 2 |
| Y-66 | + | N | N |

[1]N, no inhibition of CPE observed at highest concentration tested, or insufficient inhibition observed to predict IC$_{50}$.

The compounds used in Table 3 were further tested for activity against HSV infection in a plaque reduction assay, as detailed in Example 6. Here Vero cells, after overnight incubation, were exposed to serial dilutions of KY compound, from 0.625-10 µg/ml, and HSV-1 or HSV-2 virus for two hours. After washing to remove drug and extracellular virus, the cells were further incubated for 2 days, then stained and counted for plaque formation. Percent inhibition was determined by dividing plaques produced by total number of plaques in infected, untreated controls. From the concentration effect curve of plaque inhibition (expressed as percent of control), the concentration of compound required to produce 50% plaque reduction, IC$_{50}$, was determined. The IC$_{50}$ values for infection by HSV-1 and HSV-2 infection is given in the right-hand columns in Table 3. With reference to the compound structures given in Table 1, the following R-group features can be identified as contributing to low activity (no protection of cells from CPE effect seen at 10–20 µg/ml: in KY-48, KY-49 and KY-110, a bulky side chain in the methylene bridge; in KY-143, an OH R$_3$ group; in KY-147 and KY-148, a sulfonamide with a non-polar alkyl group at the R$_2$ position; in KY-158 and KY-175, a sulfone or sulfonyl with a non-polar alkyl group at the R$_2$ position; and in KY-395, a trimethylamine bridge in combination with a methyl ether substituent at the R$_1$ position. The "GC" symbol for KY-193 means that some giant cells were formed, indicating partial inhibitory activity. Despite the lower activity of alkyl sulfinate ester or sulfinate ester sulfone compounds, these compounds have the ability in vivo for conversion to the corresponding sulfonic acid compound by esterase action. Looking now at the compounds which give complete CPE at 10–20 µg/ml, the following R-group structures can be identified as preferred radicals:

The R$_1$ position contains OH, including combinations of OH and =O groups; alkyl and aryl esters, including combination of such esters and =O; and alkyl ethers, including combinations of such ethers and =O.

The optimal radicals at the R$_2$ position are sulfonic acid or sulfonic acid salts, sulfinic acid and salts thereof, and sulfonamides with polar amine groups, such as NH$_2$, NHOH, N-glycosides (KY-352), and amino acids.

The preferred radicals at the R$_3$ position are H or Br.

The optimal bridge linkage groups are substituted and unsubstituted methylenes, where the R group is not a bulky alkyl group, and preferably a carboxylic acid group.

As a further guide to R-group selection, compounds having an ED$_{50}$ value of ≦1 µg/ml for at least one of the two HSV tests have one of the following R-group characteristics:

Compounds whose R$_1$ groups are lower-alkyl ethers or esters, or contain a terminal carboxylic acid group are typically most active, especially in combination with =O groups at other R$_1$ sites in the compound.

The R$_2$ groups are sulfonic acid or sulfonic acid salts or sulfonamides with a terminal carboxylic acid. This feature indicates that an R$_2$ position acid group favors high activity.

The R$_4$ bridge is methylene or a methylene carrying a carboxylic acid (acetyl) group.

The ability of selected naphthalene-subunit compounds to inhibit HSV-1 and HSV-2 viral yields at selected drug concentrations up to 10 µg/ml was assessed in the viral inhibition assay described in Example 7. Briefly, cultured Hela cells were exposed to serially diluted KY compound and virus, allowed to grow for 24 hours, then freeze/thawed 3 times to release virus particles. Vero cells were infected serial dilutions of the viral lysates were assayed for plaque counts as described in Example 6. The drop in viral yield, as a function of drug concentration, is plotted in FIGS. 29A and 29B for compounds KY-1 and KY-42 respectively. The dose dependent drop in viral yield was between about 3–5 orders of magnitude, depending on drug and virus. The degree of inhibition of viral yield was generally greater for HSV-1 than for HSV-2. Similar results were observed with several other KY compounds.

B. Inhibition of HSV Activity: Calix(n)arene Compounds

A similar study of anti-HSV activities was carried out with several of the calix(n)arene compounds listed in Table 2 above, with the results shown in Table 4. As seen from column 2 of the table, all of the compounds which were tested gave inhibition of CPE at 10–20 μg/ml. Inhibition activity of the tested compounds against HSV-1 and HSV-2 in the plaque reduction assay is shown in the two righthand columns in the table (given as $IC_{50}$ in μg/ml).

TABLE 4

| Compound | CPE 10,20 μg/ml | HSV-1 $IC_{50}$ (μg/ml) | HSV-2 $IC_{50}$ (μg/ml) |
| --- | --- | --- | --- |
| Y-1 | + | 7 | 7.2 |
| KY-226 | + | 1.6 | 3 |
| Y-49 | + | 5 | 10 |
| KY-225 | + | 1.8 | 1.8 |
| Y-77 | + | 8 | 11 |
| Y-48 | + | 1.5 | 1 |
| KY-268 | + | 4.4 | 1.5 |
| KY-269 | + | 2.4 | 2.3 |
| KY-271 | + | 4.2 | 2.4 |

The highest activities observed for the phenyl-subunit compounds are comparable to the highest activities seen with the naphthyl compounds, e.g., from about 1–3 μg/ml $IC_{50}$ values.

The most active compounds, Y-226 (n=8), Y-48 (n=6), and Y-225 (n=4) all have partially oxidized $R_1$ OH/=O groups, and each partially oxidized compound is substantially more active than its corresponding non-oxidized analog.

The partially oxidized n=3 compound, KY-268, is somewhat less active than its n=4, 6, and 8 analogs. Among the non-oxidized compounds, the n=8 compound, Y-1, is somewhat more active than the corresponding n=4 and n=6 compounds.

Addition of acetyl groups at the $R_1$ position produces little change in the activities of partially oxidized compounds, also consistent with the results observed with the naphthalene-subunit compounds, addition of alkyl esters at the $R_1$ positions gave activities comparable to the partially oxidized analog.

As a general guide to optimizing compound activity in the phenyl-subunit compounds, the same rules discussed above generally apply. Thus, for example, highest activity is expected when the $R_2$ group terminates in an acid group, such as sulfonic acid. More generally, the present invention contemplates, for use in treatment of infection by enveloped virus, a calix(n)arene compound whose $R_2$ group is a polar substitutent which terminates in a sulfonic acid, phosphonic acid, or carboxylic acid group, including esters and amides of these acids which can be converted to the corresponding acid by hydrolytic cleavage in vivo. A variety of esters and amides of sulfonic acid, phosphonic acid, and carboxylic acid have been shown to undergo hydrolytic cleavage in vivo to the corresponding acids (Svensson, 1988, 1991; Stella; Bundgaard) including esters and amides of lower alkyl groups. Methods for preparing a variety of exemplary compounds of this type are described in Section IIC above.

The calix(n)arene compounds having terminal acid groups (or groups cleavable to terminal acid groups) may be substituted at other ring and bridge positions, as indicated in Section IIB and IIC above. In one preferred embodiment, the $R_1$ position of the rings is an OH group, or a combination of OH and =O groups, in the partially oxidized form of the compound.

C: Comparison of Anti-HSV Compounds

The inhibitory effect of KY-1 against drug-resistant strains of HSV-1 and HSV-2 was compared with several anti-viral agents which have been used in treating HSV infection. These compounds tested were the nucleoside analogs acyclovir (ACV), ganciclovir (DHPG), phosphonoformate (PFA), and phosphomethoxyethyladenine (PMEA). Inhibition of viral yield was determined, as above, by infecting Hela cells in the presence of wild type or drug-resistant strains of HSV-1 or HSV-2, and serial dilutions of a selected anti-viral compound, and infecting Vero cells with serial dilutions of the Hela cell lysate, as above. Details of the inhibition study are given in Example 8.

The $ID_{90}$ concentration (which effects 90% inhibition of viral yield) is given in Table 5. The KOS (HSV-1) and 333 (HSV-2) are wild type viruses; the KOS(PMEA)' and KOS(PFA)' are drug-resistant HSV-1 strains having a DNA polymerase mutation. The 333(DHPG) strain is a drug-resistant HSV-2 strain having a thymidine kinase mutation. With the exception of DHPG as an inhibitor of drug-resistant strains of HSV-1, and PMEA as an inhibitor of drug-resistant strains of HSV-2, all of the nucleoside analogs were at least about 20 times less active against drug-resistant strains than wildtype strains of either HSV-1 or HSV-2, as measured by drug concentration required to inhibit yield. By contrast, the aryl macrocyclic compound showed substantially the same specific activity against drug-resistant strains of HSV-1 and HSV-2 as against wild-type strains.

TABLE 5

| Virus | Strain/ drug selection | Mutation Locus | Drug Tested ($ID_{90}$) # | | | | |
| --- | --- | --- | --- | --- | --- | --- | --- |
| | | | KY-1 (μg/ml) | ACV (μM) | DHPG (μM) | PFA (μM) | PMEA (μM) |
| HSV-1 | KOS | None | 1.9 | 14 | 2 | 180 | 100 |
| | KOS(PMEA)' | DNA pol | 2.6 | 380 | NT | 3000 | >2000 |
| | KOS (PFA)' | DNA pol | 4.3 | 100 | 1 | >1000 | >1000 |
| HSV-2 | 333 | None | 3.2 | ≈10 | 2 | 150 | 155 |
| | 333 (DHPG)' | TK | 3.7 | >100 | 215 | NT | 120 |

The data demonstrate that aryl macrocyclic compounds are effective against drug-resistant HSV strains at drug concentrations comparable to those which are effective against wild type virus strains. By contrast, and with the exception of DHPG as an inhibitor of HSV-1 strains, both drug-resistant strains showed a significant resistance to ACV, DHPG, PFA, and PMEA, as evidenced by the several fold greater $ID_{90}$ drug concentrations required for virus inhibition.

D. Inhibition of RSV and Influenza A Virus Infectivity Representative macrocyclic compounds from Table 1 were tested for inhibition of cytopathic effects in cultured MDCK or HEp2 cells after infection by Influenza A virus (A/Taiwan strain) or RSV virus. In the method of inhibiting virus infectivity by influenza A, MDCK cells were infected with the virus, and the cells were allowed to grow in culture until cytopathic effects were clearly visible. In the absence of infection, the cells form an even monolayer of fibroblast-like cells. With virus infection, a cytopathic effect characterized by cell clumping is observed. For each compound tested, drug concentrations of 0.1, 1, 10, 25, and 100 µg/ml were added to cultured cells at the time of virus infection, as detailed in Examples 9 and 11. Twenty-four hours later the cells were examined for percent clumping, based on the percent of clumped cells of total cell particles in a given view field. The inhibition of clumping was plotted as a function of drug concentration, to determine the dose effective to produce a 50% reduction in the percent clumped cells, measured with respect to control (no drug treatment). The measured $ED_{50}$ values are given in Table 6 below.

A similar method was employed to determine the $ED_{50}$ of RSV inhibition of cytopathic effect (cell clumping) in HEp2 cells, with the results shown in Table 6. Details are given in Example 9.

TABLE 6

| Compound | $ED_{50}$ (µg/ml) Influenza A (Taiwan) | RSV |
|---|---|---|
| KY-1 | >188 | 0.19 |
| KY-3 | 6 | 0.75 |
| KY-42 | 94 | 1.50 |
| KY-47 | 94 | >250 |
| KY-85 | >250 | 1 |
| KY-97 | 5 | 0.5 |
| KY-110 | >250 | 4 |
| KY-123 | 31.3 | 1 |
| KY-151 | >94 | 1.5 |
| KY-193 | 5.0 | 0.8 |
| KY-194 | 7.9 | 0.5 |

In general, RSV was significantly more sensitive to compound inhibition than the Influenza A/Taiwan virus. Highest-IAV activity was seen with a sulfonamide with polar amine ($SO_2NH_2$) at the $R_2$ position, and with selected methylene bridge groups. Relatively high anti-RSV activity was seen with all compounds except KY-47.

E. Inhibition of HIV Infectivity: Naphthalene-Subunit Compounds

Representative macrocyclic compounds from Table 1 were tested for inhibition of cytopathic effects in cells infected with one of two HTLV-III strains, HTLV-III$_B$ and RF-II strains, as described in Example 12. Briefly, cells chronically infected with HTLV-III$_B$ or RF-II HIV strains were incubated in the presence of serial dilutions of the selected KY compound, then further cocultured with indicator cells. The extent of syncytia formation was scored under phase microscopy. The concentration effective to produce complete inhibition of syncytia formation, $ED_{100}$, is shown in Table 7 for the two HIV strains. The "N" means that the compound was not tested for that virus.

TABLE 7

| | Inhibition of Syncytia Formation | |
|---|---|---|
| Compound | HIV-HXB $ED_{100}$ | HIV-RF-II $ED_{100}$ |
| KY-1 | 8 | N |
| KY-3 | 16 | N |
| KY-42 | 8 | N |
| KY-48 | 250 | N |
| KY-85 | 32 | N |
| KY-97 | 32 | N |
| KY-110 | 63 | N |
| KY-121 | 16 | 16 |

TABLE 7-continued

| | Inhibition of Syncytia Formation | |
|---|---|---|
| Compound | HIV-HXB $ED_{100}$ | HIV-RF-II $ED_{100}$ |
| KY-123 | 16 | 16 |
| KY-129 | 16 | 8 |
| KY-143 | 250 | 125 |
| KY-147 | 250 | 250 |
| KY-148 | 250 | N |
| KY-151 | 32 | 125 |
| KY-158 | 500 | 7500 |
| KY-171 | 125 | 250 |
| KY-175 | 63 | 250 |
| KY-176 | 125 | 250 |
| KY-193 | 63 | 500 |
| KY-194 | 63 | 125 |
| KY-270 | 16 | 32 |
| KY-272 | 63 | 250 |
| KY-276 | 16 | 32 |
| KY-277 | 16 | 32 |
| KY-280 | 16 | 32 |
| KY-281 | 16 | 32 |
| KY-284 | 16 | 32 |
| KY-285 | 16 | 32 |
| KY-286 | 16 | 32 |
| KY-288 | 8 | 16 |
| KY-289 | 16 | 32 |
| KY-290 | 16 | 32 |
| KY-291 | 16 | 32 |
| KY-293 | 16 | 63 |
| KY-294 | 16 | 16 |
| KY-301 | 8 | 8 |
| KY-307 | 8 | 32 |
| KY-308 | 8 | 32 |
| KY-345 | 63 | 125 |
| KY-346 | 16 | 32 |
| KY-352 | 32 | 125 |
| KY-357 | 32 | 63 |
| KY-359 | 32 | 63 |
| KY-376 | 8 | 16 |
| KY-395 | | |
| Y-4 | 8 | 125 |
| Y-14 | 16 | 32 |
| Y-20 | 4 | 16 |
| Y-34 | N | N |
| Y-66 | N | N |

As seen from these results there is a general correlation between anti-viral activity against the two strains; that is, compounds which are most active against the HTLV-III$_B$ strains are also most active against the RF-11 strain.

With reference to the compound structures given in Table 1, the following R-group features can be identified as contributing to sub-optimal activity ($ED_{50}$ values $\geq 63$ g/ml for both strains): in KY-48, a bulky side chain in the methylene bridge; in KY-110, a methyl ketone group in the bridge; in KY-143, an OH $R_2$ group; in KY-147 and KY-148, a sulfonamide with a non-polar alkyl group at the $R_2$ position; in KY-158 and KY-175, a sulfonate ester or sulfonate ester with a non-polar alkyl group at the $R_2$ position; and in KY-272, a methyl ester at the $R_1$ position combined with an acetyl-group bridge. These features are substantially the same as those which gave reduced activity against HSV viral infectivity, i.e., showed no inhibitory effect on CPE at 10–20 µg/ml.

Similarly, those factors which promote high activity against HSV activity are in general the same as those which give highest activity against HIV infectivity. These factors include: the groups at the $R_2$ position are OH, including combinations of OH and =O groups; alkyl and aryl esters, including combination of such esters and =O; and alkyl ethers, including combinations of such ethers and =O.

The preferred radicals at the $R_3$ position are sulfonic acid or sulfonic acid salts, sulfinic acid and salts thereof, and sulfonamides with polar amine groups, such as $NH_2$, NHOH, N-glycosides (KY-352), and amino acids, with sulfonic acid. In particular, high activity was seen with sulfonic acid, sulfonate salts, and sulfonamides having a terminal carboxylic acid group.

The optimal radicals at the $R_3$ position is H, with both OH and Br giving reduced activity.

The bridge groups are preferably substituted and unsubstituted methylenes, where the R group is not a bulky alkyl group.

As a further guide to R-group selection, compounds having an $Ed_{50}$ value of $\leq 1$ $\mu g/ml$ for at least one of the two HSV tests have one of the following R-group characteristics:

Compounds whose $R_1$ groups are lower-alkyl ethers or esters, or contain a terminal carboxylic acid group are typically most active, especially in combination with =O groups at other $R_1$ sites in the compound.

The $R_2$ groups are sulfonic acid or sulfonic acid salts or sulfonamides with a terminal carboxylic acid. This feature indicates that an $R_2$ position acid group favors high activity.

The $R_4$ bridge is methylene or a methylene carrying a carboxylic acid group.

These preferred R-groups are intended to provide guidance in the selection of R groups at the $R_1$ 14 $R_4$ positions, for optimizing compound efficiency.

F. Inhibition of HIV Infectivity: Calix(n)arene Compounds

Representative calix(n)arene compounds from Table 2 were tested for inhibition of cytopathic effects in cells infected with one of two HTLV-III strains, HTLV-III$_B$ and RF-II strains, as described in Example 12, and in the subsection above. The $IC_{50}$ values measured for the HXB and RS-11 strains of HIV are given in units of $\mu g/ml$ in Table 8 below.

TABLE 8

| Compound | HIV-HXB $IC_{50}$ | HIV-RF-11 $IC_{50}$ |
| --- | --- | --- |
| Y-1 | 16 | N |
| KY-226 | 16 | 250 |
| Y-49 | N | N |
| KY-225 | 32 | 125 |
| Y-77 | N | N |
| Y-48 | N | N |
| KY-268 | 32 | 32 |
| KY-269 | 32 | 32 |
| KY-271 | 32 | 63 |

Interestingly, the Y-1 compound and KY-226 (the corresponding partially oxidized analog) have comparable activities against the HXB strain, in contrast to the significantly higher activity of KY-226 seen against HSV viruses. All of the other compounds tested have partially oxidized $R_1$ =O groups, and all compounds give comparable activity.

IV. Specificity Toward Enveloped Viruses

This section examines the specificity of the viral-inhibition method to enveloped viruses. The studies reported in subsection A show that the macrocyclic compounds used in the method act, at least in part, by binding selectively to viral envelope proteins, and that this binding blocks virus attachment to infectable cells, thereby inhibiting virus infectivity. These studies are detailed in parent U.S. patent application Ser. No. 647,720, filed Jan. 29, 1991. Subsection B examines the inhibitory effect of the macrocyclic on non-enveloped viruses.

A. Mechanism of Viral-Infection Inhibition

Figure 30:
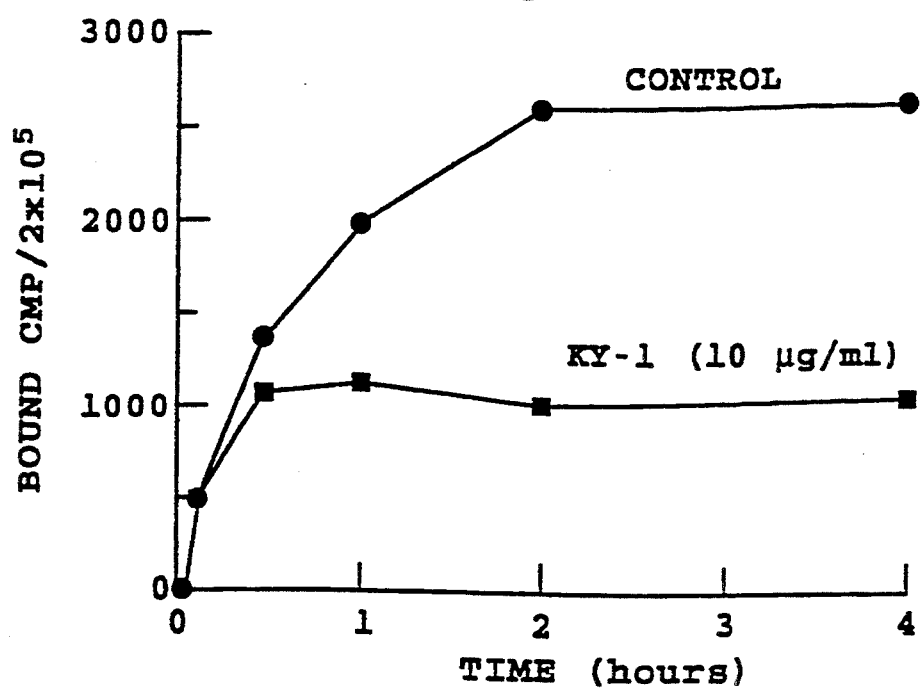
FIG. 30 hows the inhibition of 3H-labeled HSV-1 binding to cells by the compound KY-1.

In one study, the ability of a macrocyclic compound to block HSV binding to infectable cells was examined as described in Example 14. Briefly, Vero cells were exposed to radiolabeled HSV-1 or HSV-2 in the absence of KY compound or in the presence of 10 $\mu g/ml$ KY-1, and binding of the virus at times up to 4 hours after exposure to the virus was measured. FIG. 30 shows a plot of virus (radiolabel) binding to cells over the four-hour incubation period. In the absence of drug, the amount of bound virus increased steadily over two hours, and slightly from 2–4 hours. By contrast, virus binding to cells peaked at about ½ hour in the presence of drug, presumably reflecting the time during which the binding events effective to block virus binding to the cells are equilibrating.

Figure 31:
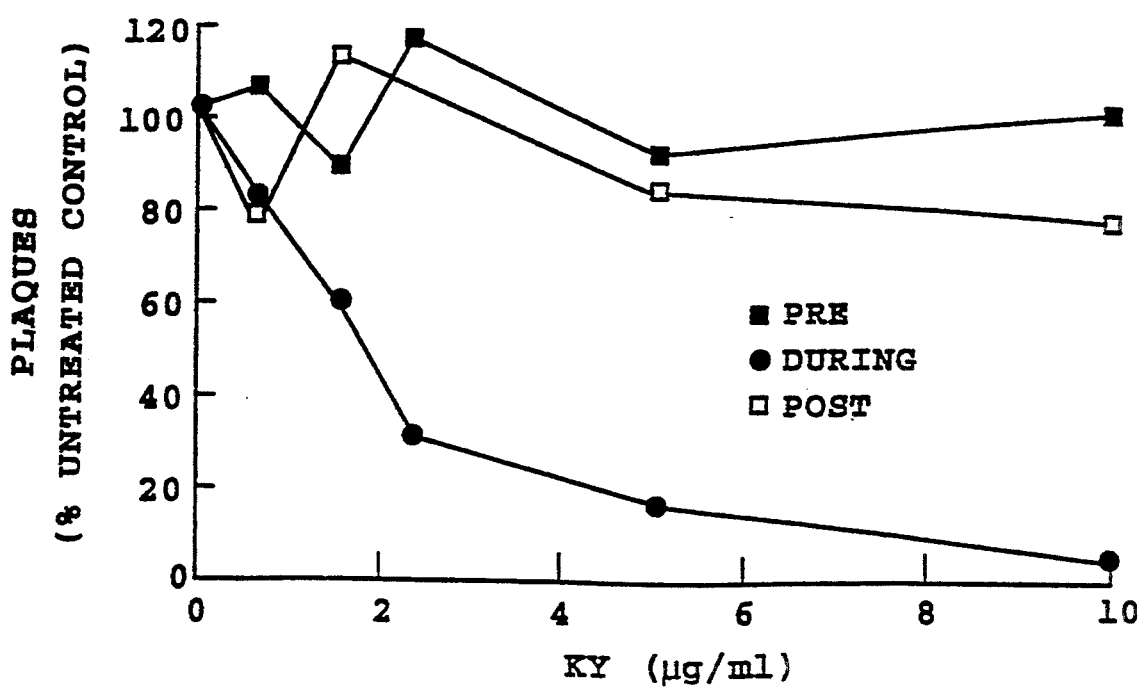
FIG. 31 is a plot of the inhibition in plaque formation of HSV-1 virus when the virus is exposed to the compound KY-1 before (open squares), (ii) after (closed squares), and during (closed circles) incubation with Vero cells.

In a second study, the effect of compound when administered prior to, during, or after cell infection by HSV-1 was examined as described in Example 15. In these studies, cells were exposed to one of a series of increasing KY-2 concentrations, and the extent of infection was measured by number of plaques observed 24 hours after infection. The reduction in plaque formation, expressed as a percent of control, is shown in FIG. 31 for cells treated with drug prior to (solid rectangles), during (closed circles), and after (open rectangles). Virus inhibition was seen most significantly when the cells were treated with drug during exposure to virus, indicating that virus inhibition occurs at the period of virus binding to and entry into infectable cells.

In a third study, purified HSV-1 virus suspensions were incubated with KY-1 or the sodium salt thereof, or a control solution for 1 hour, then serially diluted to drug concentrations between $10^1$ to $10^{-4}$ $\mu g/ml$ as described in Example 16. Addition of the serially diluted virus suspensions gave the plaque counts, measured in duplicate, shown in Table 9. The "X" symbol in the table indicates plaques too numerous to count. The results of the study demonstrate that inhibition of HSV infection by KY compounds is due, at least in part, to binding of drug to HSV particles. Further, complete virus inhibition was seen at drug final drug concentration of $10^{-2}$ to $10^{-4}$ $\mu g/ml$ (which are much lower than those needed to inhibit HSV in Vero cell culture). It can be concluded that the drug-binding/inactivation of the virus is effectively irreversible, i.e., not reversed by high dilution effects.

TABLE 9

| KY Compounds | Initial Viral Input (pfu/cell) | Plaque Number after Serial 10-time Dilutions | | | | | |
| --- | --- | --- | --- | --- | --- | --- | --- |
| | | 1 | $10^1$ | $10^2$ | $10^3$ | $10^4$ | $10^5$ |
| Control (media only) | 0.3 | XX | XX | XX | 50,41 | 9,4 | 0,0 |
| | 3 | XX | XX | XX | XX | 38,49 | 8,4 |
| KY 1 (10 $\mu g/ml$) | 0.3 | 3,2 | 0,0 | 0,0 | 0,0 | 0,0 | 0,0 |
| | 3 | 2,2 | 2,1 | 17,16 | 5,2 | 0,0 | 0,0 |
| KY 217 (10 $\mu g/ml$) | 0.3 | 2,8 | 3,3 | 0,0 | 0,0 | 0,0 | 0,0 |
| | 3 | X,X | X,X | 6,0 | 5,0 | 0,0 | 0,0 |

Figure 32A:
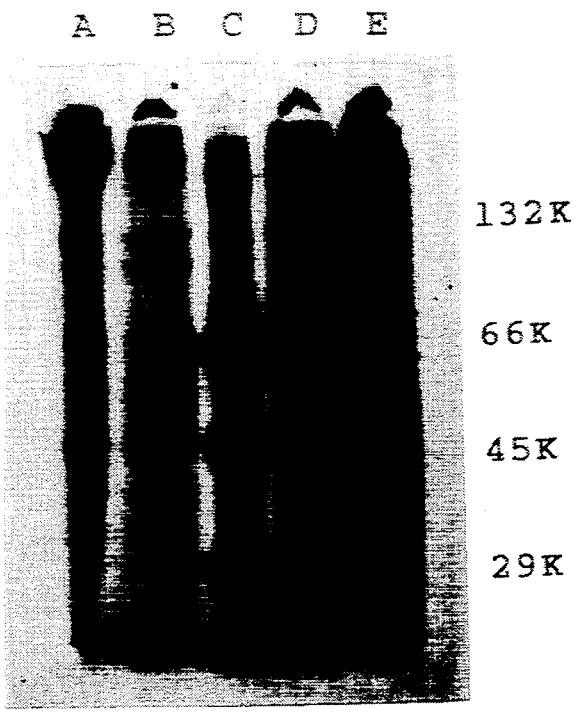
FIG. 32A shows SDS-PAGE autoradiograms of HSV-1 proteins in the presence (lane A) and absence (lane B) of mercaptoethanol, and of HSV-2 proteins in the presence (lane C) and absence (lane D) of mercaptoethanol, all with bound radiolabeled KY-1, and stained marker proteins (lane E)

In a fourth study, the binding of radiolabeled KY-1 compound to HSV-1 and HSV-2 viral proteins was examined. After compound binding, virus proteins were fractionated by sodium dodecyl sulfate polyacrylamide gel electrophoresis (SDS-PAGE), and the gel patterns developed by autoradiography. In FIG. 32A, lanes A and B in the figure are autoradiographs of HSV-1 proteins in the presence (lane B) and absence (lane B) of mercaptoethanol, and lanes C and D, analogous patterns for HSV-2 proteins. The lane at the right contains the molecular weight markers, as indicated. The major bands of drug binding in HSV-1 have molecular weights, as determined from SDS-PAGE, of 45, 66, and about 130 kilodaltons. The major bands of drug binding in HSV-2 have similar molecular weights. The major bands which show KY binding in FIG. 32B correspond in molecular weight, to HSV glycoproteins gD, gB, and gC.

B. Effect on Non-Enveloped Viruses

The ability of KY compounds to inhibit cell infection by a rhinovirus and adenoviruses 5 and 7 which are non-enveloped viruses, was similarly studied. Vero cells ($10^5$) were infected with a rhinovirus in the presence of KY-1, at concentrations ranging between 1-100 μg. Twenty-four hours after virus infection, the cells were examined for cytopathic effect, evidencing viral infection. No reduction in cell clumping was observed at any of the KY drug concentrations tested.

Vero cells were infected with adenovirus in the presence of KY-1, also at concentrations ranging between 1-100 μg, and twenty-four hours after virus infection, the cells were examined for cytopathic effect. No reduction in cell clumping was observed at any of the KY-1 drug concentrations.

In summary, a broad range of macrocyclic compounds are effective inhibitors of cell infection by each of the several enveloped viruses which were studied. Binding studies carried out in particular with respect to HSV viruses indicate that the anti-viral activity of the compounds is dependent on binding to virus envelope components, which in turn inhibits virus attachment to infectable cells. The apparent inability of the compounds to inhibit infection of non-enveloped viruses is consistent with this mechanism.

V. Viral Inhibition by a Composition Containing a Macrocyclic Compound and a Nucleoside Analog Compound The invention also includes a composition containing a macrocylcic compound of the type described above in combination with a nucleoside analog anti-viral compound. The nucleoside analog compound is one effective to inhibit viral replication at the level of viral replication or transcription. Among the nucleoside analog compounds which are useful in combination with a macrocyclic compound, in accordance with the invention are:

(1) Pyrophosphate analoges, such as phosphoformic acid (PFA), phosphonoacetic acid (PAA), methanediphosphonic acid (MDP), carbonyldiphosphonic acid (COMDP), phosphonoglyoxalic acid (COPAA), and various halogen-and/or methyl-substituted derivatives thereof, which are inhibitors of viral nucleic acid polymerases. In particular, these compounds are known to inhibit herpes virus (Blackburn, Sidwell) and Influenza (Sidwell) infections, and reverse transcriptase activity in retroviruses, such as human HIV.

(2) Base-modified analogs, such as IUDR, trifluorothymidine, AraA, and azidothymidine (AZT), didieoxyinosine (DDI), D4T, dideoxycytidine (DDC), and ribavirin. Trifluorothymidine, IUDR, and AraA are active mainly against herpes virues (Nicolson, 1984a, 1984b). Ribavirin is active against several RNA and DNA viruses (Sidwell), and AZT is active against HIV (Fischl), as are other dideoxynucleoside analogs, such as DDI.

(3) Sugar-modified analogs, such as N-acyl derivatives of 5'-amino-2', 5'-dideoxy 5'-ioduridine, sulphonamide derivatives of 5'-amino-5'-deoxythymidine, 2'-deoxy-5-ethyluridine, and N-acyl derivatives, 5'-Sulfate and 5'-sulfamate nucleoside analogs, such as nucleocidin, adenosine 5' sulfamate, and ribavarin, which may act primarily at the level of protein synthesis inhibition (Martin).

(4) Phosphate analogs, including acyclonucleoside phosphonates, such as acyclovir and gangiclovir, and their isosteric phosphonate analogs. These compounds can act as virus-selective substrates for viral thymidine kinases, in the synthesis of nucleoside triphosphate analogs intracellularly (Galbraith). Subsequently, the nucleoside triphosphate analogs can act as selective substrates for viral DNA polymerase, acting as a chain terminator since the analog does not have the bifunctionality necessary for chain extension (Allen). These compounds have demonstrated anti-viral activity against herpes viruses (Collins), including HSV-1, HSV-2, varicella zoster (VZV), and cytomegalovirus (CMV) (Smith).

Also included in this class are phosphonomethyl ethers of nucleosides, and their acyclic analogs, such as N-(3-hydroxy-2-phosphonylmethoxypropyl)- (HPMP-) and N-(2-phosphonylmethoxyethyl-)(PME-) derivatives of heterocyclic bases. These compounds act specifically against herpes viruses, adenoviruses, cytomegalovirus (DeClercq), poxviruses, vaccinia viruses, and retroviruses.

The ability of the two-compound composition to inhibit viral infection in enveloped virus is demonstrated in the study reported in Example 18, which examines the viral yields after infection of Vero cells with serial dilutions of HSV-1 or HSV-2 particles, as described above.

Figure 34A:
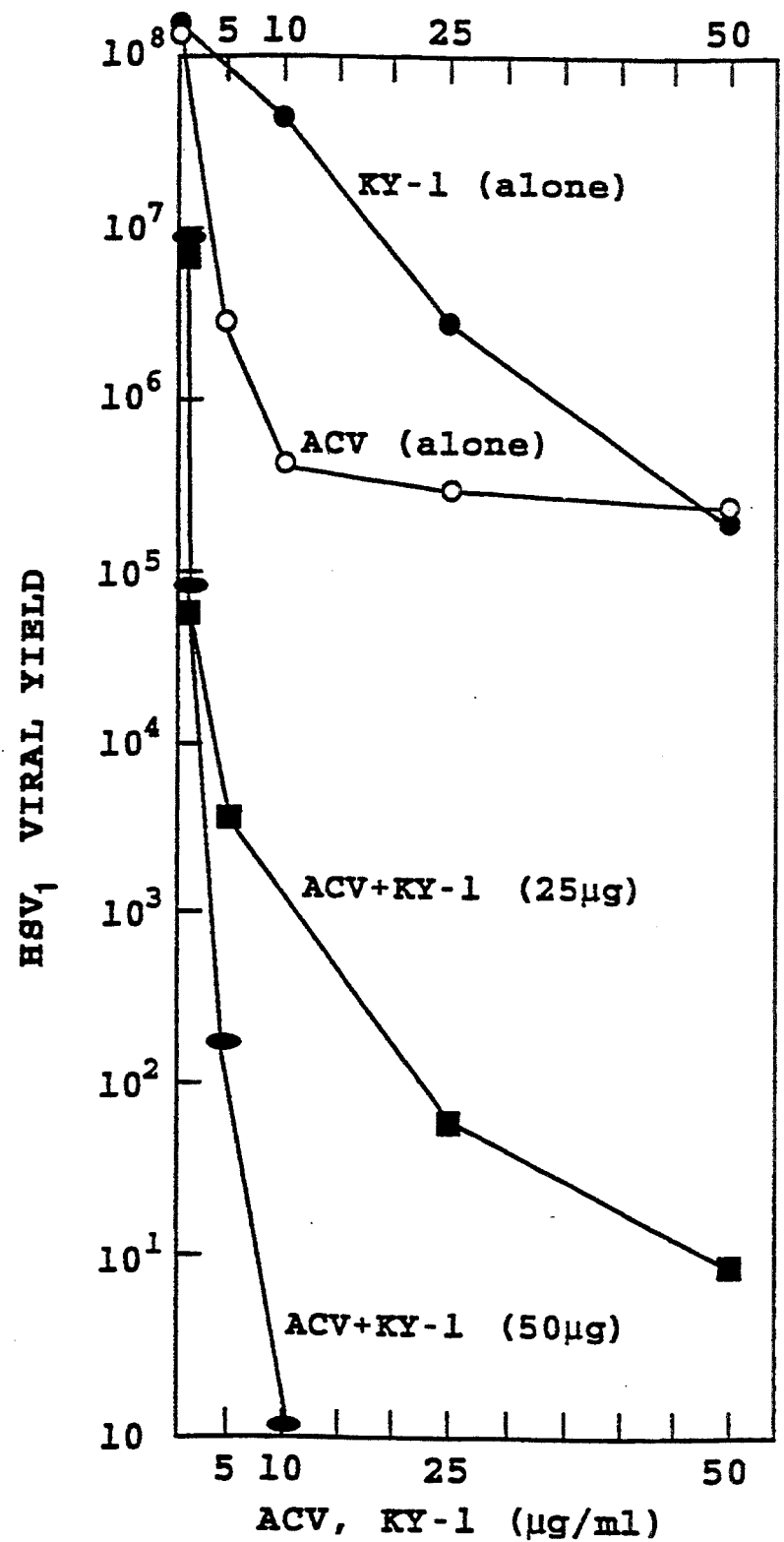
FIGS. 34A and 34B show the drop in HSV-1 (34A) and HSV-2 (34B) viral yields when infected cells are exposed to increasing concentrations of Y-1 alone (solid circles), increasing concentrations of acyclovir alone (open circles), increasing concentrations of acyclovir plus 25 µg/ml Y-1 (solid rectangles), and increasing concentrations of acyclovir plus 50 µg/ml Y-1 (solid ovals).

FIG. 34A shows the drop in HSV-1 viral yields when infected cells are exposed to increasing concentrations of the macrocyclic compound Y-1 alone (solid circles), increasing concentrations of acyclovir alone (open circles), increasing concentrations of acyclovir plus 25 μg/ml Y-1 (solid rectangles), and increasing concentrations of acyclovir plus 50 μg/ml Y-1 (solid ovals). With either drug alone, a maximum decrease in viral yield was slightly less than three logs (orders of magnitude).

Figure 34B:
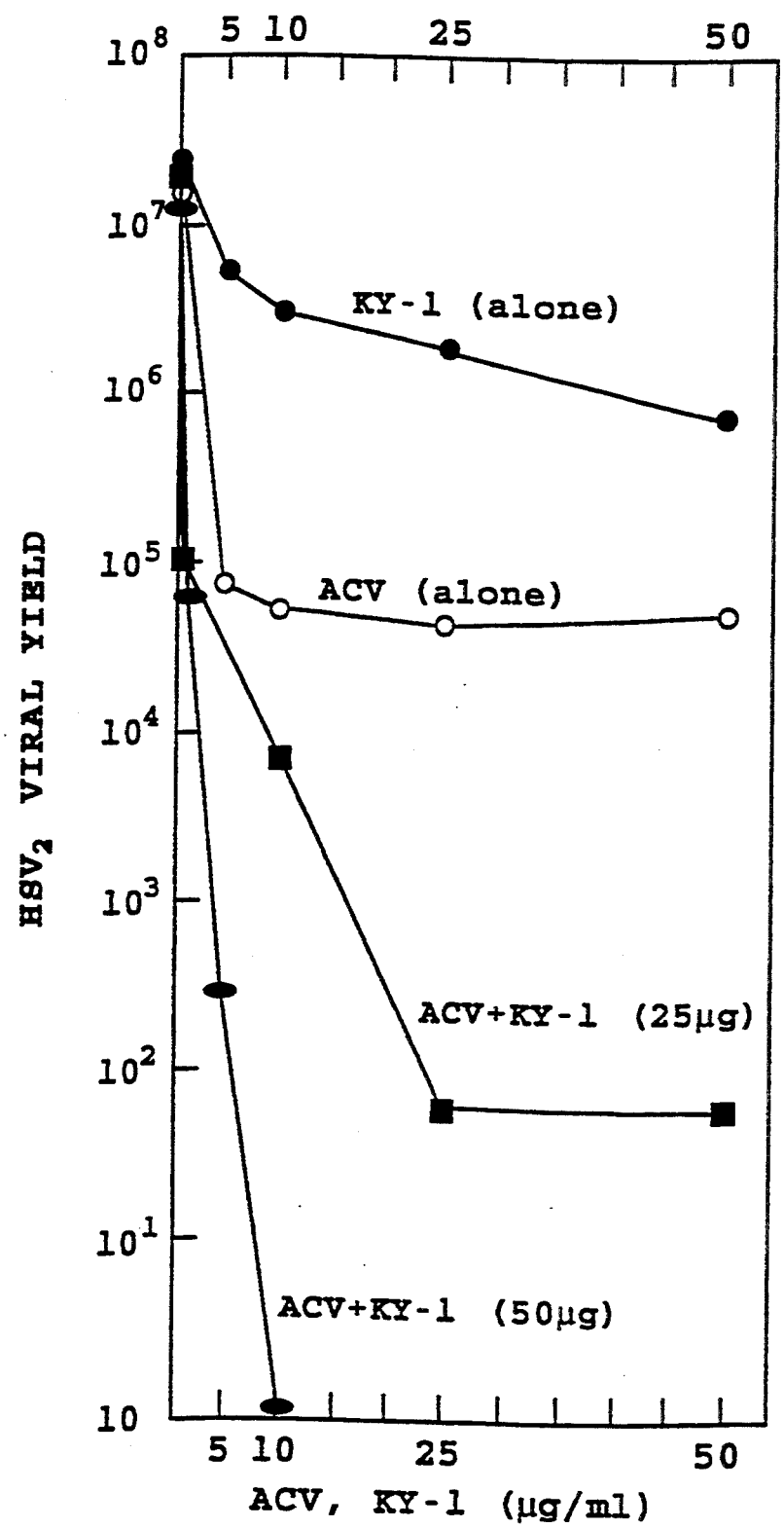

The effect of combined compounds was tested at two Y-1 concentrations. At the lower Y-1 concentration of 25 μg/ml, the two compounds together gave over seven logs inhibition in viral yield, i.e., more than tenfold greater than the sum of the inhibition produced by the two drugs alone. At the higher Y-1 concentration, the combined inhibitory effect of the two compounds was several orders of magnitude greater than the sum of effect of macrocyclic compound and acyclovir alone. Similar results were observed for inhibition of HSV-2 viral yields with combined compound treatment, as seen in FIG. 34B.

The two compounds are formulated in tablet, ointment, or injectable form at a preferred weight ratio of between about 10:1 to 1:1 macrocyclic compound and nucleoside analog, respectively. The viral-yield plots in FIGS. 34A and 34B a significantly higher level of inhibition was observed when the co-administered compounds were at a ratio of about 5:1 macrocyclic compound to nucleoside. The macrocyclic compound in the composition is preferably selected for optimal activity against the target virus, e.g., a herpes virus, respiratory syncytial virus, or retrovirus, as detailed above. Similarly, the preferred nucleoside analog compound is selected for activity against the target virus (Martin)

One advantage of the combined-drug composition is that substantially lower doses of both types of compounds are required for achieving a selected viral inhibition level, reducing drug side effects in a composition that also is characterized by greater anti-viral activity.

VI. Use of the Composition in Treatment of Viral Infection

In accordance with the invention, calix(n)arene compounds of the type described herein are administered to the site of infection in an individual infected with an enveloped virus, for treatment of the invention. The composition of the invention includes novel includes the calix(n)arene compound contained in a pharmaceutical carrier which is suitable for oral, topical or parenteral administration of the compound. The composition may contain the calix(n)arene compound alone, or in combination with an anti-viral nucleoside analog.

The dosage form of the composition is one which is pharmaceutically effective, i.e., effective to inhibit viral infection of host cells. As seen above, compound doses in the range 1–50 µg/ml are generally effective in inhibiting viral infection of cells. Thus, for many applications, an effective dose is preferably one which produces a concentration of compound in this range at the site of infection. For topical administration, a composition containing between 1–5% or more calix(n)arene is suitable.

In a composition containing both calix(n)arene and nucleoside analog compounds, the composition dose may be substantially lower in one or both compounds, as discussed in the section above.

One of the considerations in the administering the composition, particularly when the drug is administered parenterally or orally, is systemic side effects. Studies conducted in support of the present invention indicate that the calix(n)arene compound, particularly the sulfonic acid compound, may show anti-coagulant activity after oral and intravenous administration. One conclusion from these studies is that the anticoagulant effect of calix(n)arene in the bloodstream can be effectively blocked by administering a polycationic compound, such as protamine sulfate, by intravenous administration. The protamine administration is timed to correspond to highest blood levels of the calix(n)arene compounds. In a typical method, a dose of protamine equivalent to about 1 mg per 100 heparin anticoagulant units is administered intravenously simultaneously with IV administration of the calix(n)arene, or 1–2 hours after oral administration of the macrocyclic drug. It is generally recommended that protamine be infused slowly (i.e., not more than a total of 50 mg/10 minutes).

Therefore in the case of simultaneous administration of calix(n)arene compound, the rate of co-infusion of the two compounds would be adjusted such that the protamine sulfate was not introduced to the subject at a rate exceeding 50 mg/10 minutes. The composition of the invention can therefore include protamine in an amount effective to reduce the anti-coagulant effect of the macrocyclic compound, when the compound is administered for uptake into the bloodstream. Where the composition also contains a nucleoside analog drug, and lower amounts of macrocyclic drug, the protamine may be reduced or eliminated, due to the lower amounts of macrocyclic compound.

A. Injectable Composition

Studies on the pharmacokinetics and efficacy of intravenously administered composition has been studied. Briefly, it was shown that a macrocyclic compound of the type used in the method, when administered intravenously, (a) is cleared relatively slowly from the bloodstream ($t_{\frac{1}{2}}$=approx. 5–8 hours), (b) is present predominantly in free form, and (c) retains activity in the bloodstream for inhibiting viral (e.g., HSV-1, HSV-2, RSV, and HIV) infection.

The injectable composition contains the calix(n)arene in a suitable IV solution, such as sterile physiological salt solution. The solution may additionally contain nucleoside analog compound and/or protamine.

B. Topical Composition: Treatment of Genital Herpes Lesions

For inhibiting viral infection of skin and mucosal membrane, the composition is preferably formulated in an ointment form. The use of a topical composition for treatment of genital herpes lesions is illustrated in the following study, which is detailed in Example 13. Briefly, female guinea pigs were infected intravaginally with HSV-2, then treated topically three times daily beginning 6 hours or 48 hours after inoculation with HSV-2, as described in Example 13. Animal groups included control animals (no treatment following virus inoculation), placebo (vehicle treatment), KY-1 in vehicle, or acyclovir. Swabs of vaginal secretion were obtained and assayed for viral activity by a standard CPE assay. The severity of genital lesions was scored on a 0–5+ scale through the period of primary infection (21 days).

Three to four days after HSV-2 inoculation, vesicular lesions appeared on the external genital skin. Lesions progressed to an ulcerative stage by days 7–8 and gradually healed by days 15–21. The effect of topical treatment with the KY-1 preparations on lesion development and severity is shown in Table 10. The group treated with placebo at +6h had a significantly increased lesion score-day AUC ($P < 0.05$); however, mean peak lesion scores were not different when compared to the untreated control group. Lesion development as determined by both AUC values and mean peak lesion scores was significantly reduced by treatment with 5% KY-1 when given at 6h after infection compared to the placebo ($P < 0.001$). Treatment with 1% KY-1 significantly reduced the AUC at +6h ($P < 0.01$) but not mean peak lesion scores.

TABLE 10

| | Lesion Score | | | |
|---|---|---|---|---|
| | Area | | Mean Peak | |
| Treatment | Under Curve | P-Value | Lesion Score | P-Value |
| Control | 37.0 | — | 3.6 | — |
| Placebo +6 h | 47.0 | <0.05 | 3.9 | NS |
| Placebo +48 h | 42.8 | NS | 3.6 | NS |
| KY 5% +6 hr | 3.8 | <0.001 | 0.8 | <0.001 |
| KY 5% +48 h | 45.7 | NS | 3.7 | NS |
| KY 1% +6 h | 30.8 | <0.01 | 2.9 | NS |
| KY 1% +48 h | 46.6 | NS | 4.3 | NS |
| ACV 5% +6 h | 2.7 | <0.001 | 0.6 | <0.001 |
| ACV 5% +48 h | 45.8 | NS | 3.8 | NS |

No sign of any skin irritation from any of the formulations was observed. Throughout the treatment period, the genital skin remained normal in appearance; no redness or swelling was observed. The guinea pigs also remained normal and healthy in appearance throughout the entire study.

In another study using the guinea pig genital model described above, animals were infected with HSV-2, then treated with KY-1 or Y-1 topically at concentrations of 2% or 5% drug. Treatment of animals was initiated 6 or 24 hours post infection, as described in Example 13. Animals were treated and scored daily for severity of infection for 19 days. The effects of topical treatment with KY-1 and Y-1 on infection are tabulated in Table 11 and compared to treatment with 5% acyclovir (ACV).

Treatment with placebo (vehicle only) resulted in significantly worse infection scores than no treatment in this study. Drug treatment with 2% or 6% Y-1, administered hours post infection, resulted in reduced numbers of animals exhibiting lesions, decreased mean lesion scores and decreased peak lesion score, in comparison to placebo treatment. Likewise, treatment with a 6% formulation of either KY-1 or Y-1 or a 2% formulation of KY-1, administered 24 hours post-infection, resulted in reduced numbers of lesion bearing animals and reduced severity of lesions.

TABLE 11

Effect of Topical KY-1 and Y-1 on HSV-2 Genital Lesions

| Treatment | Time | N | % Animals with Lesions | Lesion Score (AUC) | Mean Peak |
|---|---|---|---|---|---|
| None | — | 9 | 66.7 | 9.1 | 1.3 |
| Placebo | 6 h | 10 | 100 | 29.0 | 3.0 |
| Y-1 (2%) | 6 h | 9 | 66.7 | 16.9 | 1.8 |
| Y-1 (6%) | 6 h | 10 | 30 | 8.1 | 1.2 |
| Placebo | 24 h | 10 | 100 | 22.3 | 2.7 |
| Y-1 (2%) | 24 h | 10 | 60 | 22.0 | 2.3 |
| Y-1 (6%) | 24 h | 10 | 40 | 14.7 | 1.8 |
| KY-1 (2%) | 24 h | 10 | 70 | 16.2 | 2.2 |
| KY-1 (6%) | 24 h | 10 | 50 | 17.5 | 1.7 |
| ACV (5%) | 24 h | 8 | 37.5 | 11.7 | 1.5 |

C. Topical Composition: Treatment of Eye Infections

In another embodiment, the topical composition includes a calix(n)arene compound in a ointment or solution form suitable for administering the compound to the eye, e.g., to the corneal surfaces of the eye. The composition may also include a nucleoside compound effective against the target viral infection.

In one treatment method, described in Example 18, graded topical doses of compound Y-1 were administered to the corneal regions of rabbits previously infected with HSV-1. Clinical slit lamp biomicroscopy was used to assess disease severity as measured by average epithelial disease involvement (FIG. 33A), conjunctivitis rating (FIG. 33B), iritis rating (FIG. 33C), and stromal disease (FIG. 33D).

Figure 33A:
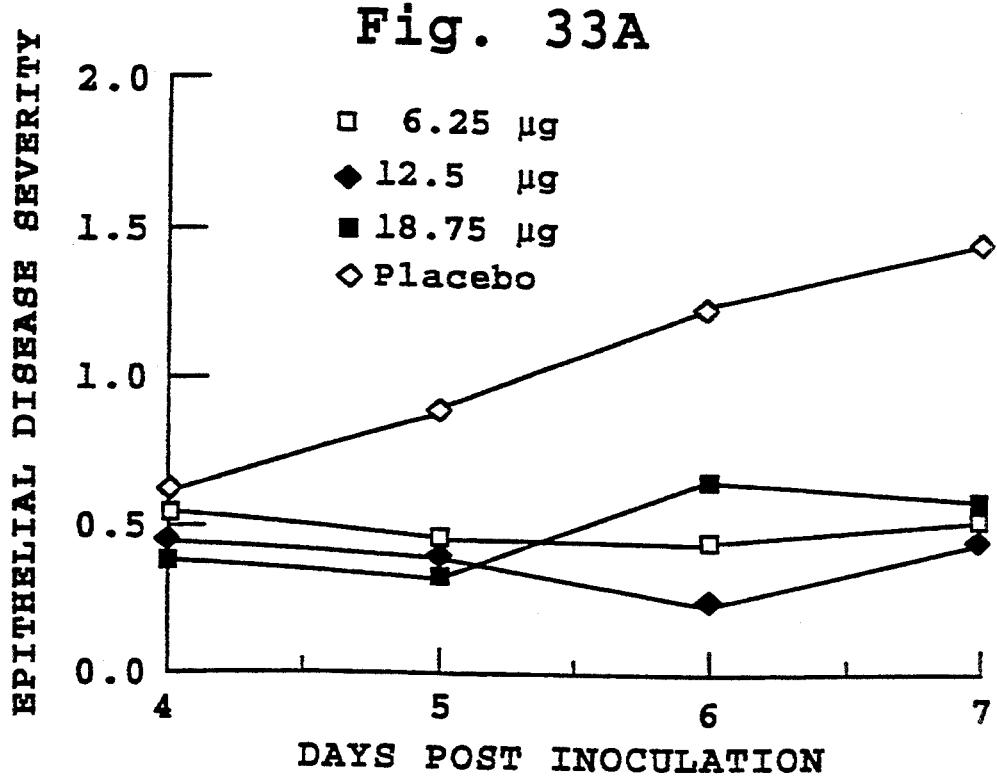
FIGS. 33 (A–D) show plots of effects of topical Y-1 on epithelial damage (33A), conjunctivitis (33B), iritis (33C), and stromal disease (33D) subsequent to ocular application of HSV-1 in rabbits.
Figure 33B:
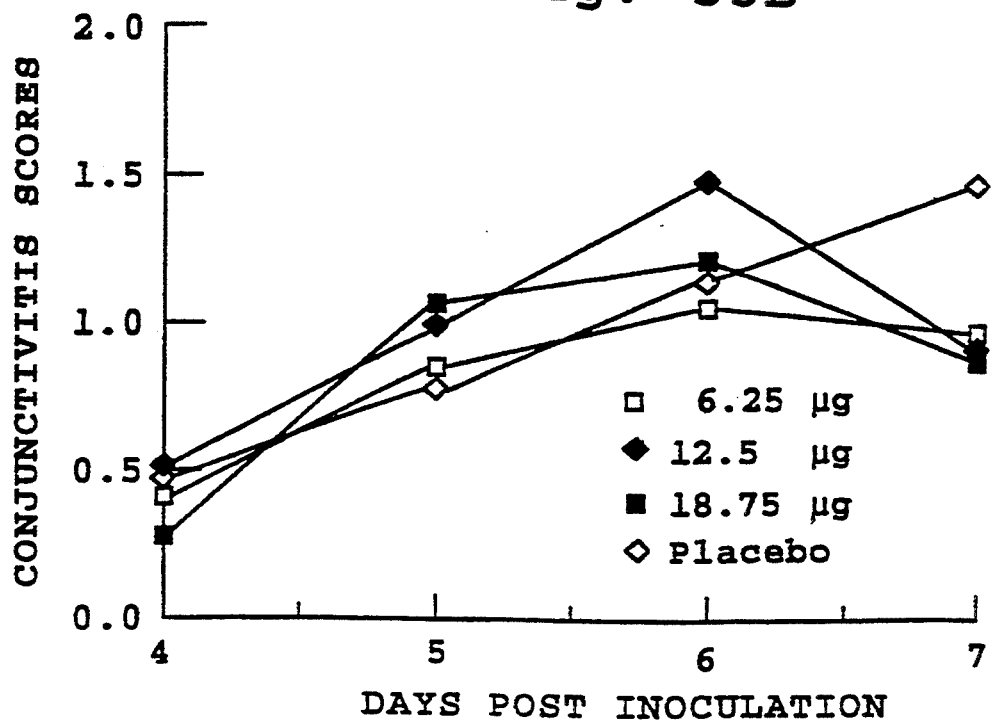
Figure 33C:
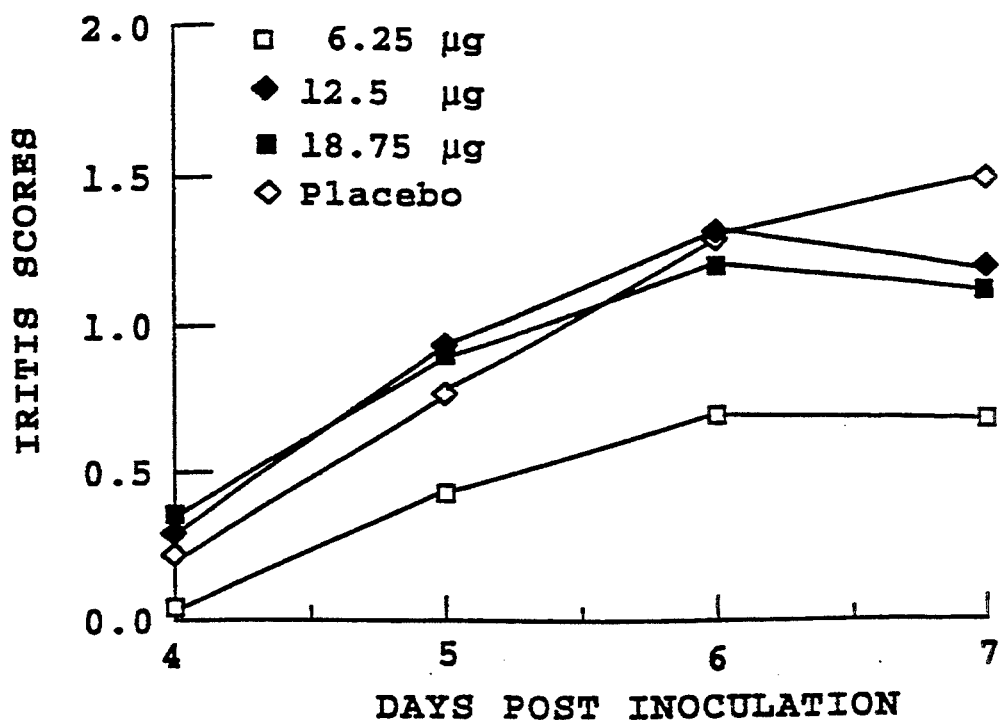
Figure 33D:
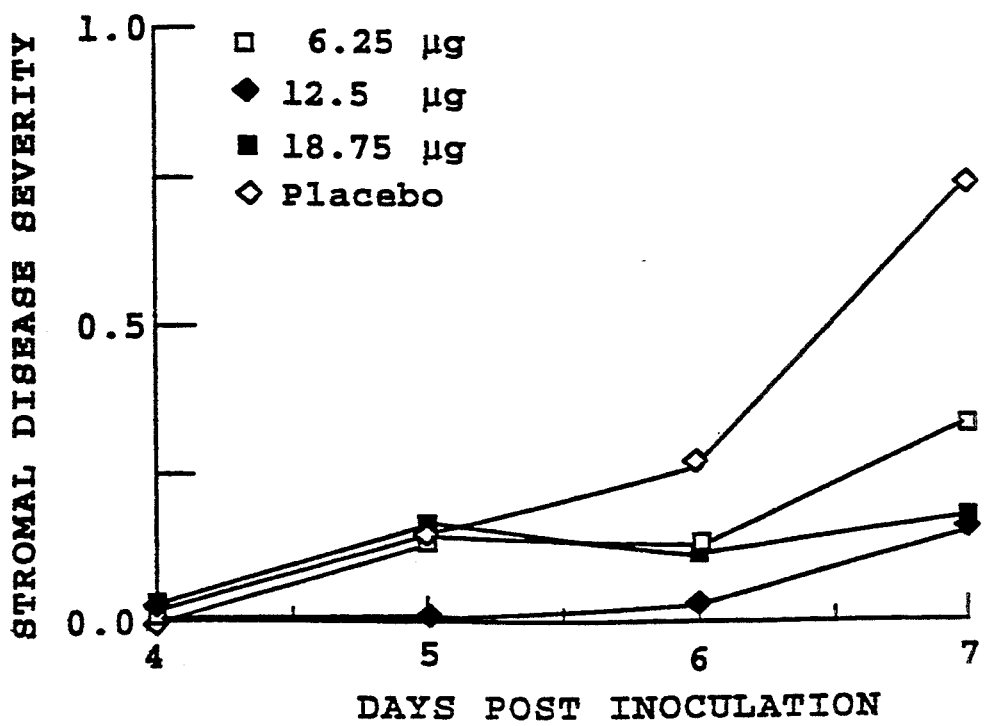

By day 7 post infection, the severity of the epithelial disease had peaked, as observed in placebo treated animals (FIG. 33A). Conjunctivitis, iritis and stromal disease parameters also progressed throughout the study (FIGS. 33B-D).

In all four assessments of ocular infection, drug treatment resulted in less severe infection as compared to placebo treatment. All concentrations of Y-1 were effective in reducing the development of HSV-1 induced ocular disease. Therapy with all concentrations of Y-1 were statistically different from each other.

A topical concentration of 12.5 $\mu$g/50 $\mu$l was the most effective ocular therapy. The epithelial disease scores decreased through day 6 post infection, and rebounded slightly on day 7 post infection. Compared to the other two Y-1 therapies, this concentration was effective in reducing the development of HSV-1 disease in the eye and was associated with only mild conjuctival, iris, and stromal disease development parameters. A higher concentration (18.75 $\mu$g/50 $\mu$l) was also effective in reducing the development of corneal epithelial HSV-1induced disease. However, this concentration of Y-1 appeared to be somewhat toxic to the corneal epithelial surface and to the conjunctiva, iris and stroma. This toxicity was evidenced as an increase in all disease parameters on days 6 and 7 post infection.

Viral titers were recovered from tear film at days 0, 3, 5, and 7 post-inoculation and from epithelial scrapings performed on day 7 post-infection (sacrifice). Viral titers were determined by plaque reduction and multiple regression analysis, as described in Example 10. In the tear film study, a marked reduction of viral titer was observed in all animals given topical doses of Y-1, and this reduction appeared dose-dependent, although no difference was seen at the highest doses (12.5 and 18.75 $\mu$g/50 $\mu$l). A dose-dependent reduction in viral titer was observed in the scrapings taken on day 7.

Based upon these studies, dose efficacy/range was generated. The optimal concentration of compound appeared to be 12.5 $\mu$g/50 $\mu$l in this study.

D. Oral Composition

Studies conducted in support of the present invention have shown that a macrocyclic drug of the type used in the invention is available in the plasma for a period from about 0.5 hrs. after oral administration (e.g., by gavage), with a peak at about 2–4 hours. The period of effective drug concentration in the bloodstream is roughly between 4 and 18 hours after IV administration. The relatively short distribution volume halflife of the drug, reflecting distribution to extracorporeal body compartments when the compound is administered intravenously, is generally advantageous in the case where drug is one which shows anti-coagulant side effects, since the concentration of compound in the bloodstream can be more closely titrated.

The following examples illustrate methods of preparing tetrameric macrocyclic compounds, in accordance with the invention, and the use in inhibiting cell infection by enveloped viruses. The examples are intended to illustrate but not limit the scope of the invention.

Materials

All chemical reagents were obtained from Aldrich Chemical Co., or from other commercial sources.

EXAMPLE 1

Preparation of Naphthalene Macrocyclic Compounds

A. KY-1 ($R_1$=OH, $R_2$=SO$_3$Na, $R_3$=H, $R_4$=>$CH_2$)

To a 41 mM aqueous solution (50 ml) of disodium chromotropic acid, 15 ml of 37% formaldehyde was added, giving a final molar ratio of 5:1 formaldehyde:chromotropic acid. The mixture was reacted with stirring in a stoppered flask at room temperature for 1 week. The resulting dark red solution (70 ml) was filtered under vacuum, and the filtrate, after being concentrated was precipitated by adding 200 ml of acetonitrile. The precipitated product was collected by filtration and taken to dryness under vacuum. The yield of KY-1 was 95%. The compound was characterized as follows:

Melting point (M.P)>300° C.; HPLC in CH$_3$CN/MeOH/H$_2$O/TFA: 14'48" single broad peak; (IR/KBr)=3425 (OH), 1638 (Ar), 1181, 1044 (SO$_3$) cm$^{-1}$; UV (H$_2$O): 238.0, 358.5 nm Mol Weight: 1505 (M+1) by mass spectroscopy; H$^1$NMR(CD$_3$OD), chemical shifts on the γ scale: 5.20 ($CH_2$, 8.01 (ArH) ppm; $C^{13}$NMR ($D_2O$), chemical shifts on the v scale: 27.19, 120.18, 121.69, 122-06, 122-67,133-30, 142.97, 154.42 and 181 ppm. Analysis: ($C_{22}H_{10}O_{16}S_4Na_4)_2 \times 6$ $H_2O$ or ($C_{22}H_{11}O_{16}S_4Na_4)_2 \times 5$ $H_2O$ Found: C 33.17, H 2.54, Na 11.93 Calculated: C 32.75, H 2.23, Na 11.41; C 33.16, H 2.13, Na 11.56.

B. KY-3 ($R_1$=OH, $R_2$=$SO_2NH_2$, $R_3$=H, $R_4$=—$CH_2$—)

KY-1 (2 mM) was treated with 5 ml chlorosulfonic acid and the mixture was stirred at 50° C. for one-half hour. The resultant mixture was added to 20 g of crushed ice to precipitate the product, which was collected by filtration and then washed with ether.

The crude product was dissolved in 100 ml of 25% ammonium water solution and allowed to react for 2 hours at room temperature. The mixture was concentrated in vacuo and the remaining oil was dissolved in a small amount of water and filtered. The product was precipitated by adding acetonitrile to the filtrate and collected by filtration and washing with acetonitrile. The compound was characterized as follows:

Melting point (M.P.)>300° C; Mass spec: 1452 (M-7$NH_2$);. HPLC in $CH_3CN$/MeOH/$H_2O$/TFA: 11'46" single peak; (IR/KBr)=3430 (OH), 3187, 1686 ($NH_2$), 1637 (Ar), 1211, 1110, 1044 ($SO_3$) $cm^{-1}$; UV ($H_2O$): 246 nm; $H^1$ NMR($D_2O$), chemical shifts on the v scale: 5.15 ($CH_2$), 7.5–8.2 (ArH) ppm; Analysis: ($C_{44}H_{40}O_{26}S_{10}N_{1}$-$_2Na_4$) -16$H_2O$ Found: C 28.62, H 3.93, N 8.82, S 17.17, Na 5.44; Calculated: C 28.51, H 3.89, N 9.07, S 17.28, Na 4.97;

C. KY-42 ($R_1$=OH, $R_2$=$SO_3Na$, $R_3$=H, $R_4$=>CHCOOH)

Chromotropic acid, disodium (10 mM) in 50 ml water was mixed with glyoxylic acid (10.0 mM, in 5 ml water) and 10 ml of 37% hydrogen chloride at room temperature. The mixture was boiled for 8 hours and the color of the solution turned to dark red. The resultant solution was added to 50 ml of water and filtered. The filtrate was concentrated and ethanol was added to precipitate the product of KY-42. The yield was 87%. The compound was characterized as follows:

Melting point (M.P.)>300° C.; Mass spec: 1623 (M-3$H_2O$). HPLC in $CH_3CN$/MeOH/$H_2O$/TFA: 10'36" single peak; (IR/KBr)=3452 (OH), 1801, 1719 (Co), 1638 (Ar), 1206, 1050 ($SO_3$) $cm^{-1}$; UV ($H_2O$): 238.0, 351.5, 520 nm; $H^1$ NMR($D_2O$), chemical shifts on the γ scale: 7.10 (CH$CO_2H$) 8.00 (ArH) ppm; $C^{13}$ NMR ($D_2O$), chemical shifts on the F scale: 116.04,118.90, 120.94, 121.27, 122.30, 124.30, 124.68, 126.60, 128.37, 136.48, 136.71, 140.50, 143.93, 144.26, 145.75, 152.01, 154.33, 156.01, 156.67; Analysis: ($C_{48}H_4O_{40}S_8Na_8)_4$-4$H_2O$ Found: C 32.74, H 2.50; Calculated: C 32.58, H 2.71;

D. KY-123 ($R_1$=OH, $R_2$=$SO_2Na$, $R_3$=H, $R_4$=>$CH_2$)

KY-1 (2 mM) was treated with 5 ml chlorosulfonic acid and the mixture was stirred at 50° C. for one-half hour. The resultant mixture was added to 50 g of crushed ice to precipitate the product which was collected by filtration and then washed with ether. The crude sulfonyl chloride product was treated with sodium sulfite (20 mM) in 4 ml water. The reaction mixture was kept slightly alkaline by addition at intervals of small portions of 50% NaOH for 2 days. After solvent removal, ethanol was added to precipitate the product, which was acidified by addition of 50% $H_2SO_4$, followed by addition of ethanol to precipitate sodium sulfate. The ethanol phase was mixed with ether (1:2, v/v) to precipitate the desired product. Product yield was 39%.

E. KY-147 ($R_1$=OH, $R_2$=$SO_2NHCH_3$, $R_3$=H, $R_4$=>$CH_2$)

N-methyl chromotropic acid chloride was formed by reacting chromotropic acid (disodium salt) with sulphonylchloride in the presence of DMF. The reaction was carried out with stirring at 80° C. for 4 hours. After removal of solvent and excess of thionylchloride in vacuo, ether was added to precipitate the chromotropic acid chloride which was subsequently collected by filtration and washed with ether. The crude product was added to 20 ml of methylamine and stirred for 2 hours. After removal of all solvent from the resultant substance, the residue was dissolved in a 200 ml of cold methanol and filtered. The filtrate was added with acetonitrile to precipitate the product chromotropic acid methyl sulfonamide. Yield 56%.

The chromotropic acid methyl sulfonamide (2 mM) in 3 ml water was reacted with 37% formaldehyde (1 ml) at room temperature for one week. Acetonitrile was added to precipitate the product which was collected by filtration and washed by acetonitrile. Yield was 85%.

F. KY-151 ($R_1$=$OC_3$, $R_2$=$SO_3Na$, $R_3$=H, $R_4$=>$CH_2$)

KY-1 (50 mM) was dissolved in 80 ml of NaOH water solution (0.2M NaOH) and heated to 50° C., dimethylsulfate (0.2M) was added slowly for 1 hour. The mixture was continuously stirred for another 2 hours and left at room temperature for 2 days. Saturated NaCl solution (100 ml) was added to the resultant substance and filtered. The precipitate was washed with ethanol, acetonitrile and ether sequentially. The dry substance was dissolved in 100 ml of methanol and filtered. The filtrate was concentrated and ether was added to precipitate the dimethyl ether of chromotropic acid, disodium.

G. KY-158 ($R_1$=OH, $R_2$=$SO_2CH_3$, $R_3$=H, $R_4$=>$CH_2$)

KY-1 from Example 1A was first treated with thionyl chloride to produce chromotropic acid sulfonyl chloride. This compound was reduced by excess sodium sulfite in the presence of sodium bicarbonate to produce the corresponding sodium sulfonate salt of cyclized chromotropic acid ($R_2$=$SO_2Na$). The sulfonate salt was treated with dimethyl sulfate in the presence of $NaHCO_3$, and worked up as described in Example 1A. Product yield was about 21%.

H. KY-175 ($R_1$=OH, $R_2$=$SO_3CH_3$, $R_3$=H, $R_4$=>$CH_2$)

Chromotropic acid was first treated with thionyl chloride to produce chromotropic acid sulfonyl chloride. This compound was then treated with sodium methoxide in methanol in the presence of sodium salt. The product was worked up as described in Example 1A to form the macrocyclic compound. Product yield was about 29%.

I. KY-285 ($R_1$=$OCOCH_3$, $R_2$=$SO_3Na$, $R_3$=H, $R_4$=>$CH_2$)

KY-1 from Example 1A (0.66 mmole) was dissolved in 3 ml water containing 0.1 g NaOH. To this was added 1 g acetyl chloride (13 mmole) and the reaction was allowed to proceed at room temperature overnight with stirring. After solvent removal, 25 ml ethanol was added to precipitate the product. The crude product was dissolved in methanol and filtered. The filtrate was allowed to precipitate, giving a 87% yield.

J. KY-346 ($R_1$=—OH, $R_2$=—SO$_3$Na, $R_3$=—H, $R_4$=—CH$_2$—N(CH$_3$)CH$_2$)

Chromotropic acid disodium salt, was dissolved in 80 ml of water at a concentration of 50 mM with stirring at 50° C. until the solution turned to clear, hexamethylenetetramine (50 mM) was then added to above solution with continuous stirring at the same temperature for additional two hours. At this time, the color of this mixture converted to dark blue. The mixture was allowed to stir at room temperature for 2 days. The resultant dark blue solution was filtered and the filtrate was concentrated, evaporated by flask, which was subsequently treated with 200 ml methanol to precipitate the product KY-346. The yield of KY-346 was 85%. The compound was characterized as follows:

M.P.>300° C.; HPLC in CH$_3$CN/MeOH/H$_2$O/TFA: 13'07" single peak; (IR/KBr)=3425 (OH), 1626 (Ar), 1197, 1052 (SO$_3$) cm$^{-1}$; UV (H$_2$O): 232.0, 377.5 nm Analysis: (C$_{13}$H$_{11}$O$_8$NS$_2$na$_2$)$_4$×12 H$_2$O Found: C 33.17, H 3.13, N 2.75 Calculated: C 33.98, H 3.59, N 2.96. Molecular weight: 1668 by gel filtration.

EXAMPLE 2

Preparation of Calix(n)arene Compounds A. Y-49 ($R_1$=—OH, $R_2$=—SO$_3$H, $R_3$=—CH$_2$—, n=4)

4-tert-butylcalix(4)arene (10 g) was treated with 200 ml of concentrated H$_2$SO$_4$ at room temperature for 0.5 hour and then at 75-85° C. oil bath for another 4 hours. The reaction was completed when no water-insoluble material was detected. The resultant oil was dropped into 500 g of crushed ice and the solution was filtered by reduced pressure. After the water removed away from the filtrate, acetonitrile (500 ml) was added to the residual and allowed to stand for 4 hours to precipitate the crude product which was then collected by filtration and washed with acetonitrile, ethyl acetate and ether. Yield 8 g (73%). The pure product was furnished by recrystallization of the crude compound with methanol-ether or methanol-acetonitrile system. The single crystal compound was also found in the recrystallization process.

Similar methods were used in the synthesis of Y-77 ($R_1$=OH, $R_3$=SO$_3$H, $R_2$=—CH$_3$—, n=6) and Y-1 ($R_1$=OH, $R_2$=SO$_3$H, $R_4$=— CH$_2$—, n=8 ) .

B. KY-225 ($R_1$=—OH, =O), $R_2$=SO$_3$H, $R_4$=>CH$_2$, ≧CH, n=4)

4-tert-Butylcalix(4)arene (1 g) was treated with 10 ml of 95-98% sulfuric acid at room temperature for 0.5 hours then at 160° C. for 5 minutes. After the resultant mixture was cool, the mixture was poured slowly into 100 ml of crushed ice and filtrated. The solution was evaporated and the residual was added with 300 ml acetonitrile to produce great amount of precipitate which was collected by filtration and washed with acetonitrile. The crude product was dissolved in 20 ml methanol and the product was precipitated by addition of diethyl ether. Yield was 84%.

Similar methods were used in the synthesis of Y-48 ($R_1$=—OH or =O, $R_3$=SO$_2$H, $R_4$=—CH$_2$—, n=6) and Y-226 ($R_1$=—OH or =O, $R_2$=SO$_3$H, $R_4$=—CH$_2$—, n=8 ) .

C. O-Acetylate of Y-1 ($R_1$=—OCOCH$_3$, $R_2$=SO$_3$H, $R_4$=>CH$_2$, n=8)

Y-1 (0.75 g) was stirred in dry acetic anhydride (30 ml) overnight. The reaction was continued until the material was dissolved in the solvent. After cooling to room temperature, the suspension was filtered. The solid was washed twice with acetonitrile and dried in vacuo. The material was washed and recrystallized.

$^{13}$CNMR (D$_2$O, δ): 173.9, 151.6, 144.1, 135.6, 130.1, 34.2, and 22.4.

D. Y-78 ($R_1$=—OH, $R_2$=SO$_2$, $R_4$=>CH$_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the material is added to 50 ml of solution containing 5.7 g glycine and 2.1 g NaOH, and stirred for 2 hours at room temperature. The crude product was dissolved in 100 ml of 25% ammonium water solution and allowed to react for 2 hours at room temperature. The mixture is concentrated in vacuo and the remaining oil is dissolved in a small amount of water and filtered. The product is precipitated by adding acetonitrile to the filtrate and collected by filtration and washing with acetonitrile.

E. Glycyl sulfonamide of Y-1 ($R_1$=—OH, $R_2$=SO$_2$NHCH$_2$CO$_2$H, $R_{50}$ >$CH_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the material is added to 50 ml of solution containing 5.7 g glycine and 2.1 g NaOH, and stirred for 2 hours at room temperature. After removal of all solvent from the resultant substance, the residue is dissolved in a 200 ml of cold methanol and filtered. The filtrate is added with acetonitrile to precipitate the product.

F. Acetyl-Bridged Y-49 ($R_1$=—OH, $R_2$=SO$_3$H, $R_4$=—CHCO$_2$H—, n=4)

4.3 g of p-hydroxybenzenesulfonic acid was treated with g gram of glyoxylic acid in 30 ml 18% conc. HCl for 2 hours at 100° C. After the reaction product was dried under reduced pressure, 50 ml of methanol was added and insoluble impurities were removed by filtration. The product was precipitated from the filtrate by addition of ether then collected by filtration and dried in vacuo.

G. Toluene Sulfonyl Ester of Y-49 ($R_1$=—SO$_3$C$_6$H$_4$CH$_3$, $R_2$=SO$_3$H, $R_4$=>CHCO$_2$H, n=4)

Under nitrogen is added toluenesulfonyl chloride (1.9 g) to a suspension of dry sodium carbonate (1.06 g), dry dimethylformamide (10 ml) and Y-49 (0.75 g). After an overnight reflux, the resulting mixture is cooled to room temperature and filtered. The filtrate is diluted with ether to precipitate out the crude product. Recrystallization from acetonitrile/ether solvent provided the product.

H. Carboxylic Acid Derivative of Y-49 ($R_1$=—CO$_2$H, $R_2$=SO$_3$H, $R_4$=>CHCO$_2$H, n=4).

Under nitrogen, trifluoromethanesulfonic anhydride (1.0 ml) is added to ice cold dry dichloromethane solution (10 ml) of 2,6, di-tert-butyl-4-methylpyridine (1.25 g) and 4-tert-butylcalix[4]arene (0.65 g). After overnight stirring at room temperature, the mixture is diluted with pentane (10 ml) and filtered. The filtrate is extracted with ice cold in aqueous NaOH solution, ice cold 1N aqueous HCl solution, then saturated aqueous NaCl solution, dried over anhydrous sodium sulfate, filtered through a pad of silica gel and concentrated in vacuo. The residue is dissolved in a mixture of dry diisapropylethylamine (10 ml), trimethylsilyl cyanide (0.5 ml) and palladium tetrakis-triphenylphosphine (20 mg). After an overnight reflux under nitrogen and then cooling to room temperature, ether (50 ml) was added and the resulting suspension was filtered. After concentration of the filtrate in vacuo and silica gel chromatography (hexane/ethyl acetate eluent), the cyano intermediate is heated at 80° C. with concentrated sulfuric acid (10 ml) for 3 hours, diluted with water (10 ml) and refluxed overnight. After cooling to room temperature, the resulting mix is added to charcoal (0.5 g) and ice (50 g). After filtration, the resulting filtrate is concentrated in vacuo to ca 15 ml in volume and the resulting solid was filtered. The solid is dissolved in a minimal amount of methanol and precipitated out by adding ether. Final purification by reverse phase C18 chromatography (methanol/water eluent) provide the product.

I. Methyl Ether of Y-1 ($R_1$=—OMe, $R_2$=$SO_3Na$, $R_4$>$CH_2$, n=8).

A mixture of Y-1 (447 mg), NaOH (6 N in water, 1.53 ml), and dimethylsulfate (9 ml) was heated at 60° C. for 20 hours. The resulting mix was added dropwise into stirring absolute ethanol (100 ml). The resulting suspension was centrifuged (9000 rpm, 20 min) and then the supernatant was removed. Twice, the resulting solid was dissolved in water (6 ml), and the resulting solution was treated as above with ethanol, centrifuged, and supernatant removed. The remaining solid was lyophilized to yield the product (420 mg).

$^{13}$CNMR ($D_2O$, δ): 161.2, 140.9, 137.6, 129.5, 63.6, and 33.5.

J. XXVI. ($R_1$=—OH, $R_2$=H, $R_3$=$R_5$=H, $R_4$=—$CH_2$—, n=4)

Calix (4) arene XXVI is prepared from 4-tert-butyl-calix(4)arene (XXV; FIG. 13) as described (Gutsche, Levine, and Sujeeth, 1985). A hot solution of 5.0 g (6.75 mmol) of XXV in 250 ml of toluene is placed in a 500 ml three-necked round-bottom flask fitted with a mechanical stirrer and a gas inlet tube. The solution is cooled to 50°-55° C., treated with 5.0 g (37 mmol) of anhydrous $AlCl_3$, and stirred for 2 h at 50°-55° C. in an inert atmosphere. The mixture is cooled in an ice bath and stirred with 125 ml of 1N HCl for 30 min, and the organic phase is separated and washed, dried, and evaporated to leave a yellow residue. This is triturated with 500 ml of ether, and the insoluble material is recrystallized from $CHCl_3$—$CH_3OH$ to yield 1.9 g (66%) of XXVI as off-white microcrystals. m.p. 313°-318° C.

K. XXVIII ($R_1$=—OH, $R_2$=COOH, $R_3$=$R_5$=H, —$CH_2$—, n=4)

Calix (4) arene XXVIII is prepared as described (Yilmaz and Vural). Known p-acetyl-calix(4) arene (XXVII; 1.3 g) (Yilmaz and Vural, 1991; No et al., 1986) is dissolved in 50 ml of 2N aqueous NaOH. A solution of iodine (8 g) and potassium iodide (20 g) in 40 ml of water is added and the mixture stirred. The solution is warmed on a water bath for 1 h. Iodoform is removed by filtration, and $NaHSO_3$ (20 g) is added to the filtrate. Concentrated HCl is then added to the filtrate to produce a pale yellow precipitate which is then filtered off, washed with water, and dried. The crude product is dissolved in 10% aq. $NaHSO_3$ and treated with charcoal. After filtration, the solution is acidified with 1N HCl. The precipitated product is collected by filtration, washed with distilled water until free of $Cl^-$, and dried in a vacuum desiccator, yielding 1.04 g (79%) of XXVIII. m.p. 320° C. (dec.).

L. XXXI. ($R_1$=—OH, $R_2$=—$CH_2COOH$, $R_3$=$R_5$=H, $R_4$=—$CH_2$—, n=4)

Calix(4)arene derivative XXXI is prepared via p-(dimethylamino)methyl-calix(4)arene (XXIX) as described (Gutsche and Nam, 1989).

To a solution of 15.9 g (39.5 mmol) of calix(4)arene (XXVI) in 360 ml of THF are added 45 ml of acetic acid, 22.5 g (0.2 mol) of 40% aqueous dimethylamine, and 16.2 g (0.2 mol) of 37% aqueous formaldehyde. The reaction mixture is stirred for 24 h at room temperature, the solvents are removed under vacuum, and the residue is dissolved in 250 ml of water. The aqueous solution is extracted twice with 200 ml of ether and neutralized with 10% $K_2CO_3$ solution, and the precipitate that forms is removed by suction filtration. The product is dried under vacuum and then recrystallized from chloroform to give 19.1 g (78%) of p-(dimethylamino)$_m$methyl-calix(4)arene XXIX as white needles.

To a solution containing 16.3 g of p-(dimethylamino)-methyl-calix(4)arene in 220 ml of DMSO is slowly added 9.57 ml (0.15 mol) of methyl iodide. After the reaction mixture is stirred for 30 min at room temperature, 15 g (0.3 mol) of NaCN is added, and the mixture is heated for 2 h at 80° C. under a nitrogen atmosphere. The solution is then cooled, treated with 1 liter of ice water, acidified with 2N HCl, filtered, and air-dried. The crude product is recrystallized from $CH_3CN$ to yield 12.8 g (88%) of p-cyanomethyl-calix(4)arene XXX as a pale yellow solid.

p-Cyanomethyl-calix(4)arene (0.5 mmol) is then added to a solution of DMSO (25 ml) and conc. aqueous HCl (5 ml) and refluxed overnight. After dilution with water (100 ml) at room temperature, the precipitate is collected by filtration and recrystalized from methanol to provide purified XXXI.

M. XXXIII. ($R_1$=—OH, $R_2$=—$CH_2CH_2COOH$, $R_3$=$R_5$=H, $R_4$=—$CH_2$—, n=4)

Calix(4)arene derivative XXXIII is prepared as described (Gutsche and Nam, 1989).

To a solution of 3.26 g (5 mmol) of (dimethylamino)-$m$ethyl-calix(4)arene (XXIX; Example L) in 80 ml of DMSO, 1.90 ml (30 mmol) of methyl iodide is added. After the mixture is stirred for 30 min, sodium diethyl malonate, prepared from 1.20 g of Na, 7.28 g of diethyl malonate, and 28 ml of EtOH, is added, and the reaction mixture is heated for 2 h at 80° C. in an atmosphere of nitrogen. The solution is then cooled, poured onto 200 ml of ice-water, acidified with 2N HCl, and worked up in the usual fashion to give 5.50 g (99%) of p-(diethylmalonyl)methyl-calix(4)arene XXXII as crude product. Hydrolysis and decarboxylation is effected by dissolving the crude product in 100 ml of DMSO and 30 ml of conc. HCl and heating at 120° C. for 10 h in an atmosphere of nitrogen. The mixture is then cooled, poured onto 500 ml of ice-water, stirred for 10 min, and filtered. The precipitate is recrystallized from acetone-ethyl acetate to give 2.42 g (69%) of XXXIII as colorless crystals. m.p. 224.

N. XXXVI ($R_1$=—OH, $R_2$=—$PO_3H$, $R_3$=$R_5$=H, $R_4$=—$CH_2$—, n=4)

Derivative XXXVI is prepared by adaptation of the methods of Arduini et al. and Hirao et al.

Calix(4)arene (XXVI) is refluxed with $Hg(OCOCF_3)_2$ in $CHCl_3$, giving an almost quantitative yield of the tetra-($Hg$-$OCOCF_3$) calixarene derivative. Following evaporation of the $CHCl_3$, metal iodine exchange is carried out by reaction of the calixarene derivative with $I_2$ in $CHCl_3$, giving p-iodo-calix(4)arene XXXIV as a brown compound in 40% yield.

A concentrated toluene solution of HPO(OEt)$_2$ (10 mmol), triethylamine (10 mmol), Pd(PPh3)$_4$ (0.3 mmol) and p-iodocalix(4)arene (1.0 mmol) is stirred at 100° C. under nitrogen atmosphere for 3 days. After dilution with ether (50 ml) at room temperature, the reaction mixture is filtered and then concentrated under high vacuum (100° C., at <0.1 mm Hg). The resultant concentrate is purified by silica chromatography to obtain purified phosphonate diester (XXXV), which is then refluxed overnight in 6N HCl (5 ml) to produce the phosphonic acid product. After removal of solvent (100° C., at <0.1 mm Hg), the solid is recrystallized from methanol to yield purified XXXVI.

O. XXXIX. ($R_1$=—OH, —CH$_2$PO$_3$H, $R_3$=$R_5$=H, —CH$_2$—, n=4)

Calix(4) arene derivative XLIV is prepared via p-chloromethyl-calix(4) arene as described (Almi et al.).

To a solution of 1.0 g (2.4 mmol) of calix(4) arene (XXVI) and 14.4 g (81 mmol) of chloromethyl-n-octyl ether in 100 ml of CHCl$_3$ cooled at −10° C., is added 4.7 ml (40.3 mmol) of SnCl$_4$ dropwise over about 15 min. The cooling bath is then removed, and the reaction mixture is kept at room temperature until all of the calixarene starting material has reacted (after ~50 min), as judged by thin layer chromatography (hexane:ethyl acetate=4:3). Water is then added slowly and the two phases are allowed to separate. The organic layer is washed twice with distilled water and is then dried over Na$_2$SO$_4$. Following removal of the Na$_2$SO$_4$, the solvent is evaporated to give a residue that is then washed with n-hexane and filtered, giving 1.23 g (80%) of product, p-chloromethyl-calix(4)arene XXXVII.

Derivative XXXVII (1 g, 1.6 mmol) is refluxed for 6 h in 20 ml of triethyl phosphite. Excess triethyl phosphite is then removed by distillation, and the resultant solid residue (phosphonate diester XXXVIII) is dried under vacuum for 8 h. A solution of 20% HCl (60 ml) is added and the resultant reaction mixture is refluxed for 20 h. The solvent is then removed by evaporation, and the resultant precipitate is filtered, washed first with methanol and then with CHCl$_3$, and dried under vacuum to give 1.11 g (80%) of XXXIX as a white solid. m.p. 360° C.

P. XLIV. ($R_1$=—OTs, $R_2$=—CH$_2$CH$_2$Br, $R_3$=$R_5$=H, $R_4$=—CH$_2$—, n=4)

p-2-Bromoethyl-calix(4)arene derivative XLIV is prepared as described (Gutsche, Levine, and Sujeeth, 1985; Gutsche, Dhawan, et al., 1983).

(a) To a solution of calix(4)arene (XXVI; 2.14 g) in 100 ml of THF and 10 ml of DMF is added 2.0 g of NaH followed by 28 g of allyl bromide. The mixture is refluxed 1 h, after which the THF is removed by evaporation, and the residue is partitioned between water and CHCl$_3$. The CHCl$_3$ extract is washed with water, dried, and evaporated, and the residue is recrystallized from 95% ethanol to give 2.18 g (74 %) of 0-allyl-calix(4)arene XL as colorless needles.

(b) A solution of 1.66 g (2.84 mmol) of the O-allyl calix(4)arene in 25 ml of N,N-diethylaniline is heated at reflux for 2 h in an inert atmosphere. The solution is cooled, poured into 250 ml of ice-water, stirred with 250 ml of concentrated HCl, and filtered to yield a crude product, which is then crystallized from isopropanol to afford 1.22 g (74%) of p-allyl-calix(4)arene XLI as off-white needles, m.p. 245°-248° C.

(c) A solution of 2.09 g (3.57 mmol) of p-allyl-calix-(4)arene in 100 ml of dry THF is treated with 1.0 g (42 mmol) of NaH followed by 4.0 g (21 mmol) of p-toluenesulfonyl chloride, and the mixture is heated at reflux for 1.5 h. The solvent is removed by evaporation to leave a light brown oil, which is dissolved in 100 mL of CHCl$_3$, cooled in an ice bath, and treated with 100 ml of ice-water. The organic phase is dried and evaporated, and the residue is recrystallized from isopropanol to yield 3.41 g (79.5%) of tosylated p-allyl-calix(4)arene (XLII).

(d) A solution of 3.50 g of tosylated p-allyl-calix(4)arene in 60 ml of CH$_2$Cl$_2$ and 40 mL of CH$_3$OH is cooled in a dry ice-acetone bath and treated with ozone until it retains a blue color (10–15 min). Nitrogen is bubbled through the solution until the blue color disappears, and 2 g of NaBH$_4$ is added. The solution is stirred at room temperature for 3–4 h, poured into ice cold, dilute HCl solution, and worked up in conventional fashion to yield a crude product as a white resin. Recrystallization from 3:5 acetone-hexane produces 1.51 g (43%) of microcrystalline p-2-hydroxyethyl-calix(4)arene phenol-oxygen-tosylate (XLIII).

(e) A solution of triphenylphosphine dibromide, prepared from 6.5 g (25 mmol) of triphenylphosphine and Br$_2$ (Schaefer et al., 1973), in 150 ml of dry acetonitrile is treated with a solution of the product from step (d), prepared from 3.25 g of the product of step (c), in 50 ml of acetonitrile. The mixture is stirred for 2 h at room temperature and filtered, and the solvent is removed by evaporation to leave a sticky orange oil. This is stirred with 250 ml of 95% ethanol for 8 h, and 3.10 g (78%) of p-2-bromoethyl-O-tosyl-calix(4)arene XLIV is collected as a white powder by filtration.

Q. XLVI ($R_1$=—OH, $R_2$=—CH$_2$CH$_2$PO$_3$H, $R_3$=$R_5$=H, $R_4$=—CH$_2$—, n=4)

Calix(4)arene derivative XLVI is prepared from p-2-bromoethyl derivative XLIV (Example P) by modification of the method used to make XXXIX from p-chloromethyl-calix(4)arene (Example O).

Purified bromide XLIV (1 mmol) is refluxed in P(OEt)$_3$ (10 ml) overnight under nitrogen atmosphere. After removal of excess phosphite at high vacuum (100° C.,0.1 mm Hg), the residue (diethyl phosphite XLV) is added to a mixture of DMSO (5 mL) and 6N NaOH (1 ml) under nitrogen and heated at 100° C. overnight, thus removing the tosylate groups. After removal of DMSO under high vacuum (100° C., <0.1 mm Hg), the residue is diluted with hot water (25 ml) and acidified with conc. HCl to give upon cooling a precipitate which is then collected by filtration. Recrystallization of the solid from methanol provides purified XLVI.

R. XLVII. ($R_1$=—OH, $R_2$=—CH$_2$SO$_3$H, $R_3$=$R_5$=H, $R_4$=—CH$_2$—, n=4)

To a solution of p-chloromethyl-calix(4)arene (XXVII, Example O; 2.5 mmol) in 95% ethanol (10 ml) is added at room temperature an aqueous solution of Na$_2$SO$_3$ (2M, 11 mmol). After refluxing overnight, the solvent is removed by distillation until a precipitate forms. The precipitate is collected by filtration, washed with cold, saturated aqueous NaCl, and then suspended in a minimum of water and passed through a column of Amberlite IR-120 resin in water. The UV-active fractions containing product are concentrated under vacuum and the residue is recrystallized from methanol to give purified XLVII.

S. XLIX. ($R_1$=—OH, $R_2$=—CH$_2$CH$_2$SO$_3$H, $R_3$=$R_5$=H, $R_4$=—CH$_2$—, n=4)

Calix(4)arene derivative XLIX is prepared from bromoethyl derivative XLIV (Example P) by applying sequentially the sulfonation method of Example R to give XLVIII, the hydrolysis step of Example Q to remove the tosyl group, and the Amberlite IR-120 step of Example R to produce sulfonic acid XLIX.

T. LII. ($R_1$=—OAc, $R_2$=t-butyl, $R_3$=$R_5$=H, $R_4$=—CH(OH)—, n=4)

Calixarene LII is made via known calixarene LI (Gormer et al; 1990: $R_1$=—OAc, $R_2$=t-butyl, $R_3$=$R_5$=H, $R_4$=—C(=O)—, n=4) as follows.

A solution of 1.5 g (2.3 mmol) of p-tert-butylcalix(4)arene (XXV) is refluxed in a solution of acetic anhydride (37 ml) and conc. sulfuric acid (0.1 ml). The reaction mixture is then added to 300 ml of ice water, producing an oil that slowly crystallizes. The crystalline solid is collected, washed several times with water, and dried with petroleum ether, giving the 0-acetyl-p-tert-butyl-calix(4)arene (L) as white crystals.

To a three-necked round-bottom flask equipped with a condenser, stirrer, and addition funnel, are added 1.2 g (1.5 mmol) of 0-acetyl-p-tert-butyl-calix(4)arene in 70 ml of acetic anhydride. To this is added dropwise a solution of 3.5 g chromium(IV)oxide in a mixture of acetic anhydride (15 ml) and acetic acid (5 ml) at 20° C. with stirring, and the reaction is stirred at 140° C. for 8 h. After cooling, the reaction mixture is added to 600 ml of ice-water and allowed to stand for 12 h. The resultant yellow precipitate is collected and washed with water. Recrystallization from methanol yields the purified keto derivative LI (O-acetyl-p-tert-butyl-calix(4)arene, $R_4$=—C(=O)—) (Gormer et al., 1990). m.p. 305° C.

To the keto derivative (1 mmol) from the previous step, dissolved in absolute ethanol (10 mL), is added $NaBH_4$ (8 mmol) in small portions at room temperature under nitrogen atmosphere. After reduction of the keto-group is complete, as judged from the disappearance of the carbonyl band at 1670 $cm^{-1}$ observed by infrared spectroscopy, acetic acid (1 ml) is added dropwise and the resulting mixture is stirred for 1 h. The solvent is removed under high vacuum (<0.1 mm Hg), and the resultant solid is refluxed in methanol (5 ml) for 20 min. After removal of solvent, the residue is purified by silica chromatography, yielding purified hydroxymethylene-bridged, O-acetyl-p-tert-butyl product LII.

U. LIII. ($R_1$=—OH, $R_2$=$R_3$=$R_5$=H, $R_4$=—CH(Cl)—, n=4)

Derivative LII (Example T; 0.5 mmol) is refluxed in $SOCl_2$ (5 ml) under nitrogen atmosphere. After evolution of $SO_2$ has ceased, excess $SOCl_2$ is removed by distillation under high vacuum (<0.1 mm Hg). To the residue is added THF (5 ml), and distillation is repeated to remove residual $SOCl_2$, yielding chloro-derivative LIII.

V. LVI. ($R_1$=—OH, $R_2$=$R_3$=$R_5$=H, $R_4$=—CH($CO_2H$)—, n=4)

(a) A reaction mixture containing chloro-derivative LIII (1 mmol) and NaCN (1.1 mmol) in DMSO (10 ml) is heated at 80° C. under nitrogen for 6 h. The mixture is then poured in ice-water (50 ml), acidified with 3 N HCl, and the resultant precipitate is collected by filtration. The filtrate is added to a mixture of DMSO (25 ml) and conc. aqueous HCl (5 ml) and refluxed overnight. After dilution with water (100 ml) at room temperature, the resultant precipitate is collected by filtration and recrystallized from $CHCl_3$/methanol to afford LV.

(b) To remove the p-tert-butyl groups, the product from the previous step is added in small portions under nitrogen atmosphere to a hot (60° C.) toluene suspension (50 ml) of $AlCl_3$ (10 mmol). After stirring overnight, the mixture is cooled to 0° C., and 1N HCl (100 ml) is added dropwise. After the addition, the organic phase is separated and concentrated in vacuo. Recrystallization from $CHCl_3$/methanol affords purified LVI.

W. LVII. ($R_1$=—OAc, $R_2$=t-butyl, $R_3$0=$R_5$=H, $R_4$=—CH($CH_2CH=CH$)—, n=4)

Chloro-derivative LIII (Example U) is dissolved in a minimum amount of THF, and the mixture is added dropwise to a stirred, cold (−78° C.) solution of THF containing ($CH_2CH=CH_2$)$_2$CuLi (0.2M, 3 mmole). The suspension is then allowed to warm to room temperature. After overnight stirring, the suspension is extracted with a 3:1 mixture (5 ml) of saturated $NH_4Cl$ and saturated $NH_3$ solutions. The organic phase is dried over anhydrous $Na_2SO_4$, filtered, and concentrated in vacuo. The residue is purified by silica chromatography to provide the 0-acetyl-p-tert-butyl allyl derivative LVII.

If desired, removal of the acetyl and t-butyl groups is achieved as in part b of the following Example.

X. LVIII. ($R_1$=—OH, $R_2$=$R_3$=$R_5$=H, $R_4$=—CH($CH_2CO_2H$)—, n=4)

(a) Calixarene LVII (1 mmol) in $CH_2Cl_2$ (10 ml) is ozonized at −78° C. until the reaction mixture turns blue. Formic acid (2 ml) and then hydrogen peroxide (1 ml) are added, and the resultant mixture is allowed to warm to room temperature while being purged with nitrogen. The mixture is then refluxed overnight, after which the solvent is removed under vacuum, yielding LVIIa.

(b) Removal of the acetyl groups is achieved by refluxing the O-acetylated product (0.2 mmol) from the previous step in a mixture of methanol (4 ml) and 6N NaOH (1 ml) overnight. After removal of solvent under vacuum, the residue is diluted with water (10 ml), acidified to pH 2. The resultant precipitate is collected by filtration and recrystallized from $CHCl_3$/hexane provides. De-t-butylation is then effected according to step b of Example V, yielding purified LVIII.

Y. LXII. ($R_1$=—O($CH_2$)$_3SO_3Na$, $R_2$=H, lower alkyl, $R_3$=$R_5$=H, $R_4$=—CH—, Calix(4)arene LXII is prepared as described (Shinkai et al., 1989).

Calix(4)arene XXVI (1.54 mmol) is dissolved in THF (100 ml) at 50° C. under nitrogen atmosphere. After cooling, sodium hydride (1.20 g, 30 mmol; 60% dispersion in oil) is added and the mixture is stirred until evolution of hydrogen ceases (∼1 h). Propane-1,3-sulfone (2.26 g, 18.5 mmol) is then added dropwise and the mixture is stirred at room temperature for 24 h. Remaining NaH is decomposed by addition of methanol, after which the solvent is evaporated under reduced pressure, and the residue is dissolved in hot water (500 ml). Any insoluble material is removed by centrifugation. The product is then precipitated by the salting-out method with sodium acetate to give purified LXII (10% yield). m.p. >300° C.

Z. LXIV. ($R_1$=—O($CH_2$)$_3SO_3Na$, $R_2$=$SO_3Na$, $R_3$=$R_5$=H, $R_4$=—$CH_2$—, n=4)

To a mixture of DMSO (10 ml), p-sulfonyl-calix(4)arene (XV, FIG. 8; 1 mmol), and 6N NaOH (1 ml) is added propane-1,3-sulfone (9 mmol), and the resultant reaction mixture is heated at 60° C. overnight. After removal of solvents under vacuum (<0.1 mm Hg), the solid residue is diluted with a minimum amount of water and then added dropwise to 100 ml of ethanol with stirring. The resultant precipitate is collected by filtration, and the steps of dilution in a minimum of water and dropwise addition to 100 ml of ethanol are repeated once. The precipitate is collected by filtration and recrystallized from methanol/CH$_3$CN provides purified LXIV.

EXAMPLE 3

Preparation of Aryl-Bridged Macrocyclic Compound

A. VII. Mixed naphthyl/Phenyl Macrocycle

Chromotropic acid, disodium (10 g) in 55 ml of water was treated with 22 ml of 30 ml 37% HCl. To this solution, 1,2-benzenedimethanol (5 g) in 55 ml of acetic acid was added and this reaction was carried at reflex for 6 hours. After filtration of the resultant mixture, acetonitrile (500 ml) was added to precipitate the crude product and collected it by filtration. The crude compound was further purified by column chromatographic purification on LH-20 resin and elution with ethanol.

B. LXXV. Napthyl-Phenyl Macrocycle (n=2 napthyl+2 phenyl)

Mixed macrocycle LXXV is prepared using the strategy outlined by de Mendoza et al.

Chromotropic acid (III, FIG. 3A; 10 mmol) and 2,5-dihydroxymethyl-3-tert-butyl-phenol (LXXII; 1 mmol) is heated at 100° C. overnight in the presence of conc. HCl (5 ml). After removal of solvent under high vacuum (100° C., <0.1 mmHg), the residue is dissolved in a minimum amount of water and eluted through a column of Sephadex LH-20 in water. The isolated product (LXXIII; 0.6 mmol), which contains two chromotropic acid units and one phenol unit, is again heated at 100° C. overnight in the presence of conc. HCl (2 ml) and 2,5-dihydroxymethyl-3-tert-butyl-phenol (LXXII; 0.6 mmol). The product (LXXIV; 0.05 mmol), isolated using a Sephadex LH-20 column, is dried under vacuum and then heated at 80° C. for 6 h in conc. sulfuric acid (1 ml) under nitrogen atmosphere. After dilution with cold water (5 ml) and treatment with charcoal (100 mg), the resulting mixture is filtered, and most of the water in the filtrate is removed in vacuo (<0.1 mmHg). The residue is dissolved in hot, saturated aqueous NaCl. Upon cooling to 0° C., a precipitate forms. The precipitate is filtered, dissolved in a minimum of water, and eluted through a column of Amberlite IR-120 in water. The fractions containing pure product are combined and lyophilized, yielding purified LXXV (0.03 mmol).

EXAMPLE 4

Cytotoxicity in Proliferating Cells

A panel of human cell lines was used to check the toxicity of the drugs, including: KB (nasopharyngeal carcinoma), HeLaS$_3$ (cervical epithelial carcinoma), PLC (hepatocarcinoma), HepG$_2$ (human hepatocarcinoma) HepG2T$_{14}$ (hepatocarcinoma transfected with HBV), WI38 (normal human lung fibroblast), BT549 (breast cancer), SW480 (breast cancer), and A549 (lung cancer).

$5 \times 10^4$ cells were plated in each well of a 24 well multi-dish in 1 ml of RPMI-1640 containing 5% FCS and P/S. On the second day after plating, one of the fifty test compounds given in Table 3 was added to the cells, at concentrations between 1–100 $\mu$g/ml. Three days later, the medium was removed and the cells were stained with Commassie Blue in 40% methanol and 7% acetic acid. The results are discussed in Section II above.

EXAMPLE 5

Inhibition of HSV Activity: Cytopathic Effect

Vero cells were maintained in RPMI-1640 medium supplemented with 5% fetal calf serum, 100 Units of penicillin per ml and 100 $\mu$g of streptomycin per ml at 37° C. in a humidified incubator containing 7% CO$_2$. The HSV strains HSV-1 (Kos-1) and HSV-2 (333) were used.

$1 \times 10^5$ Vero cells were plated in each well of a 96 well microtitre plate in 0.2 ml RPMI-1640 medium containing 5% FCS and 0.1% methyl cellulose (15 cps). After overnight incubation, and cell doubling, the medium was aspirated and replaced with 100 .1 of the same medium containing 2% FCS, and 50.1 control or drug solution to a final drug concentration of 10 $\mu$g/ml and 50 $\mu$l virus, containing about 3 PFU/cell, i.e., 6 x 10$^5$ PFU/well, of HSV-1 or HSV-2.

The cells were cultured for 24 hours at 37° C. at which time cytopathic effects are clearly visible. In the absence of viral infection, the cells form an even monolayer of fibroblast cells. With viral infection, the cells form a suspension of round cells, followed by cell clumping, whose appearance is easily distinguishable from normal fibroblast cells. If no detectable cytopathic effect was produced, the test was repeated with 10 $\mu$g/ml. A parallel set of cells without virus inoculation were done as a control for cytotoxicity to Vero cells.

Table 1 above shows the structures of the compounds which were tested, and Table 3, column 2, the compounds which protected the cells from cytopathic effect (+).

EXAMPLE 6

Inhibition of HSV Activity: Plaque Reduction

Vero cells were maintained in RPMI-1640 medium supplemented with 5% fetal calf serum, as in Example 5. $4 \times 10^5$ Vero cells were plated in a 24-well plate, in 1 ml RPMI-1640 medium containing 5% FCS and 0.1% methyl cellulose (15 cps). After overnight incubation, and cell doubling, the medium was aspirated and replaced with 100 $\mu$l of the same medium containing 2% FCS, which contained 50 $\mu$l control or drug solution to a final drug concentration of 0.25, 2.5, 5, 10, or 20 $\mu$g/ml and 50 $\mu$l virus, containing about $1 \times 10^3$ PFU/ml, i.e., 50 PFU/well, of HSV-1 or HSV-2, as in Example 5.

After 2 hrs. at 37° absorption the virus and the drugs were removed and the cells were washed with PBS and 0.5 ml of 1% methylcellulose (4K cps) in RPMI-1640+2% FCS+penicillin/streptomycin (P/S) was added. Two days later, the media were removed. The cells were stained with 0.8% crystal violet in 50% ethanol. The plaques formed were counted and the percentage of inhibition was calculated by dividing by the plaques formed in control. Ed$_{50}$ values, indicating the concentration of drug needed to produce 50% inhibition of viral plaques, were calculated assuming a linear dose response for viral plaque inhibition. The calculated IC$_{50}$ values are given in Tables 3 and 4 above.

EXAMPLE 7

Inhibition of HSV Activity: Viral Yield Inhibition $1 \times 10^6$ HeLa S$_3$ were plated in 25 T flasks in 5 ml RPMI-1640+5% FCS+P/S. 24 hours later, the medium was aspirated and replaced with $6 \times 10^6$ PFU HSV-1 or HSV-2, and serial dilutions of selected KY compounds, at 10, 5, 2.5, 1.25, and 0.625 $\mu$g/ml drug. After growth at 37° C. for 24 hours in 2 ml of RPMI-1640 containing 2% FCS and P/S, the cells were frozen at −70° C. until the time for titration. The cells were freeze/thawed 3 times to release virus from the cells, and serially diluted 10 fold.

$1 \times 10^5$ Vero cells were plated in each well of 24 well multi-dish in 1 ml RPMI-1640+5% FCS+P/S+0.1% methylcellulose (15 cps). On the second day, after removal of the medium, the 10 fold serially diluted virus in 100 μl was added in duplicate. After 2 hours incubation at 37° C., the virus was removed and 0.5 ml methycellulose (4K cps) in RPMI-1640 and 2% FCS+P/S was added. Two days later, the medium was removed. The cells were stained in 0.8% crystal violet in 50% ethanol. The plaques formed were counted and the titer was calculated from the fold of dilutions.

The reduction in virus yield, as a function of KY compound concentration, is seen in FIGS. 29A and 29B for KY-1 and KY-2.

EXAMPLE 8

Activity Against Drug-Resistant Strains of HSV-1 and Hsv-2

The following strains of HSV-1 and HSV-2 virus were used: KOS, a wild type HSV-1 virus; KOS (PMEA) and KOS (PFA), both drug-resistant HSV-1 viruses having a DNA polymerase mutation; 333, a wild type HSV-2 HSV-2 virus, and 333 (DHPG), a drug-resistant HSV-2 virus having a thymidine kinase mutation.

Inhibition of viral yield was by KY-1, acyclovir (ACV), DHPG, PFA, and PMEA was examined in each of the five HSV strains substantially as described in Example 7. Briefly, Hela $S_3$ were plated in 25 T flasks in culture, and 24 hours later, the medium was aspirated and replaced with $6 \times 10^6$ PFU of the selected HSV strain, and serial dilutions of KY-1, ACV, DHGP, PFA, and PMEA. After growth at 37° C. for 24 hours in 2 ml of RPMI-1640 containing 2% FCS and penicillin and streptomycin (P/S), the cells were frozen at −70° C. until the time for titration. The cells were freeze/thawed 3 times to release virus from the cells, serially diluted 10 fold, and the serial dilutions were added to Vero cells in culture. After 2 hours incubation at 37° C. the virus was removed and 0.5 ml methycellulose (4K cps) in RPMI-1640 and 2% FCS+P/S was added. Two days later, the medium was removed. The cells were stained in 0.8% crystal violet in 50% ethanol. The plaques formed were counted and the titer was calculated from the fold of dilutions. From the drug dose response, the concentration of each drug required to effect a 90% inhibition of virus yield, the $IC_{90}$ concentration was determined. These values are shown in Table 5 above.

EXAMPLE 9

Inhibition of RSV Activity

Assays to assess the antiviral activity of KY- and Y-compounds in tissue culture were performed in 96-well flat-bottom tissue culture plates (Falcon 307), using conditions similar to those used in the cytotoxicity assays described above. In these assays, compound was tested in quadruplicate by serially diluting the compound in 2% FCS-MEM using serial two-fold dilutions (0.05 ml/well). A 0.05 ml volume of the appropriate virus containing approximately 100 median tissue culture infectious doses ($TCID_{50}$) was then added to all wells except those set aside as antiviral and tissue control wells. Next, approximately $3 \times 10^3$ HEp2 cells (0.1 ml) were added to each well. Control wells containing antiviral and no virus (antiviral control), containing virus but no antiviral (virus control), or containing medium without virus or antiviral (tissue control), were included in each test. The challenge virus was then back titrated. All assay plates were incubated at 35° C. for 5 to 7 days in a 5% $CO_2$ incubator. When virus control wells exhibited 70% to 100% CPE including syncytia, all wells were observed. The median efficacious concentration ($IC_{50}$) was calculated after determining the final concentration of antiviral in the last wells in each set of quadruplicate rows exhibiting <50% CPE compared to the CPE in virus control wells. The $Ed_{50}$ values calculated for each of the compounds tested are shown in Table 5.

EXAMPLE 10

Activity against HSV virus: Topical activity against in vivo ocular cultures of HSV-1

New Zealand white rabbits were acclimated for a minimum of two days prior to inoculation to allow the animals to accommodate to conditions in the vivarium facility. After the accommodation period, animals received a slit lamp ocular examination to exclude any animals with preexisting anterior segment ocular defects. Animals were bilaterally inoculated topically with an 80 μl drop of Minimal Essential Medium (MEM; Gibco) containing $10^5$ pfu/ml McKrae strain HSV-1; eyes were massaged for 30 seconds. Animals were replaced individually in cages.

On day 4 post inoculation (PI), animals were evaluated by slit lamp microscopy. Corneal epithelial, iris, and conjunctival disease were graded on an increasing scale of severity from 0+ to 4+. After evaluation, animals were divided into 4 groups of 5 animals with matched corneal, stromal and conjunctival involvement. Topical therapy was initiated immediately after animal grouping. Therapy groups included:

Group #1: 5 rabbits, Y-1 topical therapy (6.25 μg/50 μl) 5×/day for 4 days;

Group #2: 5 rabbits, Y-1 topical therapy (12.5 μg/50 μl) 5×/day for 4 days;

Group #3: 5 rabbits, Y-1 topical therapy (18.75 μg/50 μl) 5×/day for 4 days;

Group #4: 5 rabbits, placebo therapy (sterile water) 5×/day for 5 days.

The concentration of Y-1 for the ascending dose tolerance study were based upon the ED90 concentrations determined in the virus yield or CPE assays. Group 1 received topical eyedrop therapy containing 6.25 μg/50 μl [one-half of the ED90 concentration]; Group 2 received eyedrop therapy containing 12.5 μg/50 μl [the ED90 concentration]; Group 3 received eyedrop therapy containing 8.75 μg/50 μl [1.5 times the ED90 concentration]. All Y-1 doses were formulated to contain these concentrations in a volume of 50 μl (a standard eye drop).

Topical therapy with 0–19 μg Y-1 in 50 μl was initiated on day 4 post-inoculation (PI) and continued to day 7 PI. All animals received daily ocular slit lamp evaluations from day 3 through day 7 PI. The ocular HSV-1 induced disease severity was recorded daily.

Eyes of all animals were additionally sampled for the presence of infectious HSV-1 on days 0 (pre-inoculation), 3, 5, and 7 PI. Briefly, tear film was obtained by swabbing the lower and upper conjunctival sacs and retaining the swab in the nasal fornix for 10 seconds. The swabs were eluted individually in Hank's Buffered Saline (HBSS, Gibco Laboratories). Fifty microliter aliquots of the virus-HBSS eluate was adsorbed onto confluent HFF cell monolayers for 5 minutes. Monolayers were hydrated with Minimal Essential Medium (MEM; Gibco Laboratories), incubated at 37° C. and observed daily for two weeks to detect cytopathology consistent with HSV infection (HSV CPE). Cultures not exhibiting HSV CPE were blind passaged to confirm negativity.

On day 7 PI (sacrifice), the corneal epithelium was scraped from the eyes and HSV was recovered on HFF cell monolayers. Corneal epithelial co-cultures were evaluated daily by inverted light microscopy. Cultures not exhibiting HSV CPE were blind passaged to confirm negativity.

Clinical efficacy of the three Y-1 concentrations used in single-agent therapies were compared to placebo therapy. Virus recovery during and after topical therapy with the Y-1 formulations were compared to each other and to placebo therapy, as illustrated in FIGS. 33(A–D) and 34(A,B).

EXAMPLE 11

Inhibition of Influenza A Activity

The anti-influenza A activity of KY compounds was evaluated as described in Example 9, except that MDCK cells (kidney cell line) was used for infection in vitro by influenza virus (strain A/Taiwan).

EXAMPLE 12

Inhibition of HIV-Induced Cell Fusion

Human $CD_4^+$ indicator cells (VB) and chronically infected $H_9$ cells were maintained in RPMI-1640 medium supplemented with 5% fetal calf serum, 100 Units of penicillin per ml and 100 µg of streptomycin per ml at 37° C. in a humidified incubator containing 7% $CO_2$. The HIV strains that were used were HTLV-III$_B$ and RF-II strains obtained from the National Institutes of Health (Bethesda, MD).

For the fusion assay, serial dilutions between 1:2 and 1:2$^8$ of a selected KY compound, 1 mg/ml in PBS were made in a 96 well round bottom plate. The diluted KY compound was transferred to a 96 well flat-bottom plate. To each well was added 25 µg chronically infected $H_9$ cells (at $2\times10^6$, cells/ml), or cells chronically infected with RF-II strain HIV, followed by incubation at 37° C. for 45 minutes. To each well was then added 25 µl VB cells (about $5\times10^4$ cells), and the cells and virus isolates were cocultured for 18 hours in a humid 5% $CO_2$ atmosphere. The extent of syncytia formation was scored under phase microscopy, and the concentration which completely inhibited syncytia formation ($ED_{100}$) was recorded. The results are given in Table 7.

EXAMPLE 13

Effect of KY Topical Administration on Genital HSV Infection

A. Virus and Viral Inoculation

The MS strain of HSV-2 was utilized for the experimental animal infection. Female Hartley strain guinea pigs (Charles River Breeding Laboratories, Kingston, NY) weighing 250–300 g were inoculated intravaginally with $2.0\times10^5$ plaque-forming units of HSV-2 one hour after being swabbed for removal of vaginal secretions.

B. Treatment of Guinea Pigs

In the first study, groups of 10 guinea pigs were treated topically (0.1 ml intravaginally +0.1 ml on external genital skin) three times daily (approximately every eight hours) for seven days beginning 6 h or 48 h after inoculation with HSV-2. Groups of three uninfected animals were treated in a similar manner to assess any skin irritation.

In a second study, groups of 8–10 animals were treated three times daily with topical formulations of 2% or 6% KY1 or Y-1, with treatment beginning either 6 or 24 hours following viral inoculation, as indicated in Table 8B. Formulations of KY-1 or Y-1 were prepared by dissolving the compound in a 1.5% methyl cellulose solution such that final concentration of compound was 2% or 5% (wt/wt). Control animals were given either no treatment (N=10 animals) or treatment with placebo (1.5% methylcellulose solution).

C. Sample Collection and Virus Assays

To determine the effect of treatment on vaginal viral replication, swabs of vaginal secretions were obtained on days 1, 3, 5, 7 and 10 after HSV inoculation, placed in a tube containing 2.0 ml of media, vortexed and frozen at −70° C. until titrated for HSV-2. When all samples were collected, they were thawed, diluted serially and HSV-2 titers determined using rabbit kidney cells in a microtiter CPE assay.

D. Evaluation of Efficacy

To determine the effect of therapy on the development and spread of external genital lesions, lesion severity was scored on a 0–5+ scale through the primary infection period (19–21 days). Lesion score-day areas and virus titer-day areas under the curve, and peak lesion scores and peak virus titers between untreated and placebo-treated or placebo-treated and drug-treated animals were compared using the Mann-Whitney U range sum test. A p-value of 0.05 or less was considered significant. The results are discussed with reference to Tables 10 and 11 in Section IV above.

Animals were scored daily for 19 days following inoculation for presence of lesions and severity of lesions (on a 0–5+ point scale). Lesion scores were tabulated as area under the curve of daily lesion score vs. time (days) and peak lesion score observed. Data are presented in Table 11. A known antiviral agent, acyclovir (ACV) was administered in a 5% formulation to 8 animals as a positive control in the study.

EXAMPLE 14

Inhibition of HSV-1 Binding to Vero Cells

Vero cells were maintained in RPMI-1640 medium, as described in Example 5. After overnight incubation, and cell doubling, the medium was aspirated and replaced with 100 .1 of medium containing 2% FCS composed of 50.1 control or drug solution to a final drug concentration of 10#g/ml and 50 µl virus, containing about 3 PFU/cell, i.e., $6\times10^5$ PFU/well, of $H^3$-labeled HSV-1. At time intervals of 5, 30, 60, 120, and 240 minutes, cells were removed from the suspension, washed two times with PBS, and assayed for bound virus (cpm $^3H$). The results are given in FIG. 30, where the control virus binding is indicated by solid circles, and the drug-inhibited binding, by open rectangles.

EXAMPLE 15

Effect of Drug/Virus Exposure on HSV Inhibition

Vero cells were maintained in RPMI-1640 medium, as above. After overnight incubation, and cell doubling, the medium was aspirated and replaced with 100 µl of medium containing 2% FCS. In one group of wells, serial dilutions of KY-1 compound, between 0.625 and 10 µg/ml drug were added in 50 µl, together with 50 µl of HSV-1 virus suspension, $5\times10^6$ PFU per well. The cells were incubated for 2 hours at 37° C., then washed with PBS and assayed for number of virus plaques, as in Example 6.

In a second group of cells, serial dilutions of the drug were added to the cells, prior to the addition of the HSV-1 virus, and the cells were incubated for 2 hours at 37° C. in the presence of the virus. After washing the cells to remove free drug, virus suspension was added, $5\times10^6$ PFU per well. The cells were incubated for 2 hours at 37° C., then washed with PBS and assayed for number of virus plaques, as in Example 6.

In a third group of cells, 100 μl virus suspension was added to the cells, $5\times10^6$ PFU per well, and the cells were incubated for 2 hours at 37° C., then washed with PBS to remove unbound virus. Serial dilutions of KY-1 compound, between 0.625 and 10 μg/ml drug were added to the cells in 100 μl. The cells were incubated for 2 hours at 37° C. in the presence of the drug, then washed with PBS and assayed for number of virus plaques, as above.

The numbers of plaques observed in each of the above treatment methods, expressed as percent of untreated control, are plotted in FIG. 31. The solid circles indicate co-exposure of the cells to drug and virus; the solid squares, preincubation of the cells with drug before addition of virus; and the open squares, preincubation of the cells with virus before addition of drug.

EXAMPLE 16

Inactivation of HSV-1 by KY compounds

Purified HSV-1 was suspended in RPMI-1640 medium (Gibco Laboratories) containing 2% FCS, penicillin and streptomycin. To aliquots of the suspensions were added control, KY-1, or KY-217 solution, to a final drug concentration of 10 μg/ml, and a final virus particle concentration of $6\times10^6$ or $6\times10^5$ PFU/ml. The suspensions were incubated for 1 hour at 37° C., then diluted serially at 10 fold dilutions to final drug concentrations of 10, $10^0$, $10^{-1}$, $10^{-2}$, $10^{-3}$ and $10^{-4}$ μg/ml drug concentrations The serially diluted particles were then added to Vero cells for two hours, as in Example 6, and the cells examined for plaques 48 hours later. The number of plaques counted on each of two plates, for each virus and drug concentration, are given in Table 9.

EXAMPLE 17

Binding of KY Compounds to HSV Proteins

A. Binding of KY compound to HSV Proteins

HSV-1 and HSV-2 viral suspensions from above, each at a concentration of about $5\times10^7$ CFU/ml, were incubated for 2 hours at 37° C. with $5\times10^5$ cpm 14C-labeled KY-1 (50 μg/ml). Each viral suspension was divided into two aliquots and solubilized with 0.5% sodium dodecyl sulfate (SDS), with or without 1% mercaptoethanol. The four solubilized samples were fractionated on 8.5% polyacrylamide gel, and the gels developed by autoradiography, according to standard procedures. The autoradiographs of the four samples are seen in FIG. 32A, where the lanes are HSV-1, with (lane A) and without (lane B) mercaptoethanol, and HSV-2, with (lane D) and without (lane E) mercaptoethanol, with the marker proteins in lane C.

B. Identification of Binding Proteins

Figure 32B:
FIG. 32B shows SDS-PAGE autoradiograms of radiolabeled KY-1 compound bound to HSV-1 glycoproteins gD (lanes A and B), gB (lanes C and D), and gC (lanes E and F)

HSV-1 and HSV-2 virus suspensions were solubilized with SDS and fractionated on SDS-PAGE as above. Each sample was run in triplicate, corresponding to groups D, B, and C in FIG. 32B. The two gels in each group were analyzed by Western blotting as follows: The gels in groups D, B, and C were first reacted with mouse monoclonal antibody specific against HSV glycoprotein gD, gB, and dC, respectively. The antibodies were obtained from Dr. S. Chatterjee from the University of Alabama. The gels were then incubated with alkaline phosphatase-labeled goat antimouse antibody, to label the glycoprotein in each group. The glycoprotein with bound antibody was identified by reaction with $H_2O_2$ in the presence of nitroblue tetrazolium and bromochloroindolephosphate, according to standard methods. The results are shown in FIG. 32B.

EXAMPLE 18

Inhibition of HSV By Combined Drug Exposure

A. Inhibition of HSV-1

HSV-1 particles were obtained from infected HeLa cells, as described in Example $7\times10^5$ Vero cells were plated in each well of 24 well multi-dish in 1 ml RPMI-1640+5% FCS+P/S+0.1% methylcellulose (15 cps). On the second day, after removal of the medium, the 10 fold serially diluted virus in 100 μl was added in duplicate, plus (i) a selected concentration of GL-288 alone (up to 50 μg/ml), (ii) a selected concentration of acyclovir alone (up to 50 μg/ml); (iii) a selected concentration of acyclovir (up to 50 μg/ml) plus 25 μg/ml GL-288; or (iv) a selected concentration of acyclovir (up to 50 μg/ml) plus 50 μg/ml GL-288, to Vero cells in culture.

After 2 hours incubation at 37° C., the virus was removed and 0.5 ml methycellulose (4K cps) in RPMI-1640 and 2% FCS +P/S was added. Two days later, the medium was removed. The cells were stained in 0.8% crystal violet in 50% ethanol. The plaques formed were counted and the titer was calculated from the fold of dilutions.

The reduction in virus yield, as a function of compound concentration, is seen in FIG. 34A.

B. Inhibition of HSV-2

HSV-2 particles were obtained from infected HeLa cells, as described in Example 7. Vero cells were infected with serial dilutions of the virus particles plus GL-228 alone, acyclovir alone, or acyclovir plus GL-228 as described in Section A. After 2 hours incubation at 37° C., the virus was removed, and 0.5 ml methycellulose (4K cps) in RPMI-1640 and 2% FCS+P/S was added. Two days later, the medium was removed. The cells were stained in 0.8% crystal violet in 50% ethanol. The plaques formed were counted and the titer was calculated from the fold of dilutions.

The reduction in virus yield, as a function of compound concentration, is seen in FIG. 34B.

Although the invention has been described with reference to preferred compounds and method of virus inhibition employing the compounds, it will be appreciated that various modification and changes may be made without departing from the invention.

It is claimed:

1. A method of inhibiting infection of a mammalian cell by herpes simplex virus HSV-1 or HSV-2 comprising
    administering to the site of infection a therapeutically effective dose of a calix(n)arene compound which is derivatized, at its ring positions meta to the bridge attachments to the ring, with polar substituents having a terminal carboxylate, phosphonate, or sulfonate group.

2. The method of claim 1, wherein the number of subunits in the compound (n) is 4–10.

3. The method of claim 1, wherein the calix(n)arene compound is partially oxidized.

4. The method of claim 1, which has the general structure:

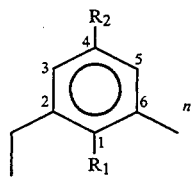

wherein (a) n=4, 6, or 8;
(b) $R_2$ is a polar substitutent with a terminal carboxylate, phosphate, sulfonate, or sulfinate group, and
(c) $R_1$ is OH or =O.

5. The method of claim 4, wherein $R_2$ has the form: $(CH_2)_m R_2'$, where m=1–3, and $R_2'$ is a sulfonate group.

6. The method of claim 5, wherein the sulfonate group includes a sulfonate ester or amide of a lower alkyl group.

7. The method of claim 4, wherein $R_2$ has the form: $(CH_2)_m—R_2'$, where m=0–3, and $R_2'$ is a carboxylate group.

8. The method of claim 7, wherein the carboxylate group is a carboxylate ester or amide of a lower alkyl group.

9. The method of claim 4, wherein $R_2$ has the form: $(CH_2)_m—R_2'$, where m=0–3, and $R_2$ is a phosphonate group.

10. The method of claim 9, wherein the phosphonate group is a phosphonate ester or amide of a lower alkyl group.

11. The method of claim 1, wherein the compound is administered orally.

12. The method of claim 1, wherein the compound is administered intravenously.

13. The method of claim 1, wherein the compound is administered.

14. The method of claim 1, for use in oral or parenteral administration, which further administering to the subject, protamine sulfate in an amount effective to inhibit anti-coagulant effects of calix(n)arene compound.

15. The method of claim 1, which further includes administering to the subject, an antiviral nucleoside analog compound selected from the group consisting of pyrophosphate analogs, trifluorothymidine, IUDR, AraA, acyclonucleoside phosphonates, and nucleoside phosphonomethyl ethers.

16. The method of claim 15, wherein the nucleoside analog is acyclovir.

* * * * *

UNITED STATES PATENT AND TRADEMARK OFFICE
CERTIFICATE OF CORRECTION

PATENT NO. : 5,441,983
DATED : August 15, 1995
INVENTOR(S) : Hwang et al.

It is certified that error appears in the above-indentified patent and that said Letters Patent is hereby corrected as shown below:

In column 52, in claim 13, insert --topically-- after "administered".

Signed and Sealed this

Nineteenth Day of May, 1998

Attest:

BRUCE LEHMAN

*Attesting Officer*     *Commissioner of Patents and Trademarks*